(12) United States Patent
Proud

(10) Patent No.: US 9,392,939 B2
(45) Date of Patent: *Jul. 19, 2016

(54) METHODS USING A MONITORING DEVICE TO MONITOR INDIVIDUAL ACTIVITIES, BEHAVIORS OR HABIT INFORMATION AND COMMUNICATE WITH A DATABASE WITH CORRESPONDING INDIVIDUAL BASE INFORMATION FOR COMPARISON

(71) Applicant: Hello Inc., San Francisco, CA (US)

(72) Inventor: James Proud, San Francisco, CA (US)

(73) Assignee: Hello Inc., San Francisco, CA (US)

( * ) Notice: Subject to any disclaimer, the term of this patent is extended or adjusted under 35 U.S.C. 154(b) by 79 days.

This patent is subject to a terminal disclaimer.

(21) Appl. No.: 13/960,407

(22) Filed: Aug. 6, 2013

(65) Prior Publication Data

US 2014/0247144 A1    Sep. 4, 2014

Related U.S. Application Data

(63) Continuation-in-part of application No. 13/923,909, filed on Jun. 21, 2013, and a continuation-in-part of application No. 13/923,637, filed on Jun. 21, 2013, now Pat. No. 8,810,430, and a continuation-in-part of (Continued)

(51) Int. Cl.
*G08C 19/16* (2006.01)
*A61B 5/00* (2006.01)
(Continued)

(52) U.S. Cl.
CPC ............. *A61B 5/0015* (2013.01); *A61B 5/0022* (2013.01); *A61B 5/0024* (2013.01);
(Continued)

(58) Field of Classification Search
CPC ... A61B 5/024; A61B 5/1455; G06F 19/3418
See application file for complete search history.

(56) References Cited

U.S. PATENT DOCUMENTS 3,127,363 A    3/1964 Nitzsche et al.
3,715,334 A    2/1973 Karstedt
(Continued)

FOREIGN PATENT DOCUMENTS

DE    3839900 A1    5/1990
EP    0183553 A2    6/1986
(Continued)

OTHER PUBLICATIONS

Davida, G.I., et al., "On enabling secure applications through off-line biometric identification", Proceedings of the IEEE Symposium on Security and Privacy (May 1998).

(Continued)

*Primary Examiner* — Omeed Alizada
(74) *Attorney, Agent, or Firm* — Paul Davis; Beyer Law Group LLP

(57) ABSTRACT

A method is provided for obtaining monitored information about an individual and provide the individual with feedback. A monitoring device with one or more sensors is used to measure or detect individual information selected from of at least one of, an individual's activities, behaviors and habit information, and an individual's health. The monitoring device has ID circuitry with an ID storage that contains a unique individual ID, a communication system which reads and transmits the unique individual ID from the ID storage, a power source and a pathway system. The monitoring device communicates with a telemetry system. The telemetry system has a database that includes base individual information selected from at least one of, individual physiological information, information that is indicative of the individual's activities, data indicative of one or more contextual parameters of the individual and information regarding a degree to which an individual has followed a routine.

26 Claims, 29 Drawing Sheets

Related U.S. Application Data application No. 13/923,614, filed on Jun. 21, 2013, now Pat. No. 8,850,421, and a continuation-in-part of application No. 13/923,809, filed on Jun. 21, 2013, and a continuation-in-part of application No. 13/923,750, filed on Jun. 21, 2013, and a continuation-in-part of application No. 13/923,583, filed on Jun. 21, 2013, now abandoned, and a continuation-in-part of application No. 13/923,560, filed on Jun. 21, 2013, now Pat. No. 8,803,366, and a continuation-in-part of application No. 13/923,543, filed on Jun. 21, 2013, and a continuation-in-part of application No. 13/923,937, filed on Jun. 21, 2013.

(60) Provisional application No. 61/772,265, filed on Mar. 4, 2013, provisional application No. 61/823,502, filed on May 15, 2013, provisional application No. 61/812,083, filed on Apr. 15, 2013.

(51) Int. Cl.
| | | |
|---|---|---|
| *H02J 7/02* | (2016.01) | |
| *H02J 17/00* | (2006.01) | |
| *A61B 5/11* | (2006.01) | |
| *H04W 4/00* | (2009.01) | |
| *H02J 7/00* | (2006.01) | |
| *A61B 5/0205* | (2006.01) | |
| *H04W 4/02* | (2009.01) | |

(52) U.S. Cl.
CPC .............. *A61B5/1118* (2013.01); *H02J 7/025* (2013.01); *H02J 17/00* (2013.01); *H04W 4/005* (2013.01); *A61B 5/02055* (2013.01); *A61B 5/6831* (2013.01); *A61B 2560/0214* (2013.01); *A61B 2562/08* (2013.01); *H02J 2007/0096* (2013.01); *H04W 4/02* (2013.01)

(56) References Cited

U.S. PATENT DOCUMENTS

| | | | |
|---|---|---|---|
| 3,775,452 | A | 11/1973 | Karstedt |
| 3,813,364 | A | 5/1974 | Zuba et al. |
| 3,814,730 | A | 6/1974 | Karstedt |
| 4,394,317 | A | 7/1983 | McAfee et al. |
| 4,603,152 | A | 7/1986 | Laurin et al. |
| 4,780,556 | A | 10/1988 | Hata et al. |
| 5,057,151 | A | 10/1991 | Schuster et al. |
| 5,319,363 | A | 6/1994 | Welch et al. |
| 5,348,008 | A | 9/1994 | Bornn et al. |
| 5,564,429 | A | 10/1996 | Bornn et al. |
| 5,735,887 | A | 4/1998 | Barreras, Sr. et al. |
| 5,910,544 | A | 6/1999 | Ozawa et al. |
| 5,971,941 | A | 10/1999 | Simons et al. |
| 6,038,315 | A | 3/2000 | Strait et al. |
| 6,120,467 | A | 9/2000 | Schallhorn |
| 6,200,289 | B1 | 3/2001 | Hochman et al. |
| 6,221,012 | B1 | 4/2001 | Maschke et al. |
| 6,323,846 | B1 | 11/2001 | Westerman et al. |
| 6,416,471 | B1 | 7/2002 | Kumar et al. |
| 6,440,067 | B1 | 8/2002 | DeLuca et al. |
| 6,454,708 | B1 | 9/2002 | Ferguson et al. |
| 6,570,557 | B1 | 5/2003 | Westerman et al. |
| 6,580,356 | B1 | 6/2003 | Alt et al. |
| 6,661,372 | B1 | 12/2003 | Girerd et al. |
| 6,677,932 | B1 | 1/2004 | Westerman |
| 6,893,396 | B2 * | 5/2005 | Schulze et al. ................. 600/300 |
| 7,113,932 | B2 | 9/2006 | Tayebnejad et al. |
| 7,248,894 | B2 | 7/2007 | Fujieda et al. |
| 7,314,451 | B2 * | 1/2008 | Halperin et al. .............. 600/534 |
| 7,502,643 | B2 | 3/2009 | Farringdon et al. |
| 7,614,008 | B2 | 11/2009 | Ording |
| 7,616,110 | B2 | 11/2009 | Crump et al. |
| 7,633,076 | B2 | 12/2009 | Huppi et al. |
| 7,653,883 | B2 | 1/2010 | Hotelling et al. |
| 7,657,849 | B2 | 2/2010 | Chaudhri et al. |
| 7,663,607 | B2 | 2/2010 | Hotelling et al. |
| 7,720,855 | B2 | 5/2010 | Brown |
| 7,733,224 | B2 | 6/2010 | Tran |
| 7,844,914 | B2 | 11/2010 | Andre et al. |
| 7,957,762 | B2 | 6/2011 | Herz et al. |
| 7,959,567 | B2 | 6/2011 | Stivoric et al. |
| 8,006,002 | B2 | 8/2011 | Kalayjian et al. |
| 8,028,905 | B2 | 10/2011 | Holberg |
| 8,033,996 | B2 | 10/2011 | Behar |
| 8,044,363 | B2 | 10/2011 | Ales et al. |
| 8,126,729 | B2 | 2/2012 | Dicks et al. |
| 8,126,735 | B2 | 2/2012 | Dicks et al. |
| 8,157,731 | B2 | 4/2012 | Teller et al. |
| 8,180,591 | B2 * | 5/2012 | Yuen et al. ................. 702/160 |
| 8,204,786 | B2 | 6/2012 | LeBoeuf et al. |
| 8,239,784 | B2 | 8/2012 | Hotelling et al. |
| 8,251,903 | B2 | 8/2012 | LeBoeuf et al. |
| 8,279,180 | B2 | 10/2012 | Hotelling et al. |
| 8,328,718 | B2 | 12/2012 | Tran |
| 8,352,211 | B2 | 1/2013 | Vock et al. |
| 8,369,936 | B2 | 2/2013 | Farringdon et al. |
| 8,378,811 | B2 | 2/2013 | Crump et al. |
| 8,381,135 | B2 | 2/2013 | Hotelling et al. |
| 8,389,627 | B2 | 3/2013 | Rubinsztajn et al. |
| 8,390,463 | B2 | 3/2013 | Munthe-Kaas et al. |
| 8,398,546 | B2 | 3/2013 | Pacione et al. |
| 8,479,122 | B2 | 7/2013 | Hotelling et al. |
| 8,587,426 | B2 | 11/2013 | Bloem |
| 8,663,106 | B2 | 3/2014 | Stivoric et al. |
| 2002/0015024 | A1 | 2/2002 | Westerman et al. |
| 2002/0019586 | A1 * | 2/2002 | Teller et al. ................. 600/300 |
| 2002/0109600 | A1 | 8/2002 | Mault et al. |
| 2002/0178126 | A1 | 11/2002 | Beck et al. |
| 2003/0023467 | A1 | 1/2003 | Moldovan |
| 2003/0121033 | A1 | 6/2003 | Peev et al. |
| 2003/0143113 | A2 | 7/2003 | Yuzhakov et al. |
| 2004/0044799 | A1 | 3/2004 | Sivaraman et al. |
| 2005/0113650 | A1 | 5/2005 | Pacione et al. |
| 2005/0137480 | A1 | 6/2005 | Alt et al. |
| 2005/0190059 | A1 | 9/2005 | Wehrenberg |
| 2005/0245839 | A1 | 11/2005 | Stivoric et al. |
| 2006/0017692 | A1 | 1/2006 | Wehrenberg et al. |
| 2006/0026536 | A1 | 2/2006 | Hotelling et al. |
| 2006/0030891 | A1 | 2/2006 | Saltzstein et al. |
| 2006/0033724 | A1 | 2/2006 | Chaudhri et al. |
| 2006/0064030 | A1 | 3/2006 | Cosentino et al. |
| 2006/0066449 | A1 | 3/2006 | Johnson |
| 2006/0089592 | A1 | 4/2006 | Kadhiresan et al. |
| 2006/0098772 | A1 | 5/2006 | Reho et al. |
| 2006/0136270 | A1 | 6/2006 | Morgan et al. |
| 2006/0197753 | A1 | 9/2006 | Hotelling |
| 2006/0264778 | A1 | 11/2006 | Lim et al. |
| 2007/0149862 | A1 | 6/2007 | Pipke |
| 2007/0167753 | A1 | 7/2007 | Van Wyk et al. |
| 2007/0174633 | A1 | 7/2007 | Draper et al. |
| 2008/0012701 | A1 | 1/2008 | Kass et al. |
| 2008/0076969 | A1 | 3/2008 | Kraft et al. |
| 2008/0146890 | A1 | 6/2008 | LeBoeuf et al. |
| 2009/0023428 | A1 | 1/2009 | Behzad et al. |
| 2009/0088820 | A1 | 4/2009 | Mao et al. |
| 2009/0112247 | A1 | 4/2009 | Freeman et al. |
| 2009/0119760 | A1 | 5/2009 | Hung et al. |
| 2009/0182208 | A1 | 7/2009 | Cho et al. |
| 2009/0234206 | A1 | 9/2009 | Gaspard et al. |
| 2009/0240120 | A1 | 9/2009 | Mensinger et al. |
| 2009/0255122 | A1 | 10/2009 | Azrielant |
| 2009/0318773 | A1 | 12/2009 | Jung et al. |
| 2010/0141042 | A1 | 6/2010 | Kesler et al. |
| 2010/0234695 | A1 | 9/2010 | Morris |
| 2010/0277003 | A1 | 11/2010 | Von Novak et al. |
| 2011/0055132 | A1 | 3/2011 | Mahdian et al. |
| 2011/0068935 | A1 | 3/2011 | Riley et al. |
| 2011/0179450 | A1 | 7/2011 | Kim et al. |
| 2012/0035487 | A1 | 2/2012 | Werner et al. |
| 2012/0133079 | A1 | 5/2012 | Sykes et al. |
| 2012/0149996 | A1 | 6/2012 | Stivoric et al. |
| 2012/0170305 | A1 | 7/2012 | Rudek et al. |

(56) References Cited

U.S. PATENT DOCUMENTS

| | | |
|---|---|---|
| 2012/0170521 A1 | 7/2012 | Vogedes et al. |
| 2012/0184876 A1 | 7/2012 | Freeman et al. |
| 2012/0194341 A1 | 8/2012 | Peichel et al. |
| 2012/0196832 A1 | 8/2012 | Luria |
| 2012/0225719 A1 | 9/2012 | Nowozin et al. |
| 2012/0226639 A1 | 9/2012 | Burdick et al. |
| 2012/0242501 A1 | 9/2012 | Tran et al. |
| 2012/0253485 A1 | 10/2012 | Weast et al. |
| 2012/0290327 A1 | 11/2012 | Hanlon et al. |
| 2012/0290950 A1 | 11/2012 | Rapaport et al. |
| 2012/0302920 A1 | 11/2012 | Bridger et al. |
| 2012/0330109 A1 | 12/2012 | Tran |
| 2013/0030711 A1 | 1/2013 | Korhonen |
| 2013/0035785 A1 | 2/2013 | MacVittie et al. |
| 2013/0154851 A1 | 6/2013 | Gaskill et al. |
| 2013/0172691 A1 | 7/2013 | Tran |
| 2013/0175732 A1 | 7/2013 | Lust et al. |
| 2013/0255681 A1 | 10/2013 | Batch et al. |
| 2013/0267794 A1 | 10/2013 | Fernstrom et al. |
| 2013/0326790 A1 | 12/2013 | Cauwels et al. |
| 2014/0019468 A1 | 1/2014 | Federoff et al. |
| 2014/0129942 A1 | 5/2014 | Rathod |

FOREIGN PATENT DOCUMENTS

| | | | |
|---|---|---|---|
| EP | 0271423 | A1 | 6/1988 |
| EP | 0369255 | A2 | 5/1990 |
| EP | 371004 | A1 | 5/1990 |
| EP | 0477681 | A2 | 4/1992 |
| EP | 0567253 | A1 | 10/1993 |
| EP | 0640663 | A2 | 3/1995 |
| EP | 0654497 | A1 | 5/1995 |
| EP | 1094091 | A1 | 4/2001 |
| EP | 1113042 | A2 | 7/2001 |
| EP | 1133936 | A1 | 9/2001 |
| EP | 1172414 | A2 | 1/2002 |
| EP | 1217042 | A1 | 6/2002 |
| EP | 1367534 | A2 | 12/2003 |
| EP | 1371004 | A2 | 12/2003 |
| EP | 1555297 | A1 | 7/2005 |
| EP | 1595676 | A1 | 11/2005 |
| EP | 1785454 | A1 | 5/2007 |
| EP | 1792944 | A1 | 6/2007 |
| EP | 1883798 | A1 | 2/2008 |
| EP | 2052352 | A1 | 4/2009 |
| EP | 2063555 | A1 | 5/2009 |
| EP | 2428774 | A1 | 3/2012 |
| EP | 2582116 | A2 | 4/2013 |
| EP | 2614945 | A2 | 7/2013 |
| GB | 1278798 | A | 6/1972 |
| GB | 1381933 | A | 1/1975 |
| GB | 2460890 | A | 12/2009 |
| WO | WO-8704449 | A1 | 7/1987 |
| WO | WO-9500992 | A1 | 1/1995 |
| WO | WO-9956922 | A1 | 11/1999 |
| WO | WO-02063555 | A2 | 8/2002 |
| WO | WO-2006127726 | A1 | 11/2006 |
| WO | WO-2008050951 | A1 | 5/2008 |
| WO | WO-2012/170305 | A1 | 12/2012 |
| WO | WO-2013076676 | A1 | 5/2013 |
| WO | WO-2013081447 | A1 | 6/2013 |

OTHER PUBLICATIONS

Juels, A., et al., "A Fuzzy Vault Scheme", Proceedings of the 2002 IEEE Symposium on Information Theory (Jun. 2002).

Juels, A., et al., "A fuzzy commitment scheme", Proc. 5th ACM Conference on Comp. and Commun. Security, pp. 28-36 (1999).

Yang, S., et al., "Secure fuzzy vault fingerprint verification system", Asilomar Conf. on Signals, Systems and Comp., vol. 1, pp. 577-581 (Nov. 2004).

Uludag, U., et al., "Fuzzy fingerprint vault", Proc. Workshop: Biometrics: Challenges arising from theory to practice, pp. 13-16 (Aug. 2004).

* cited by examiner

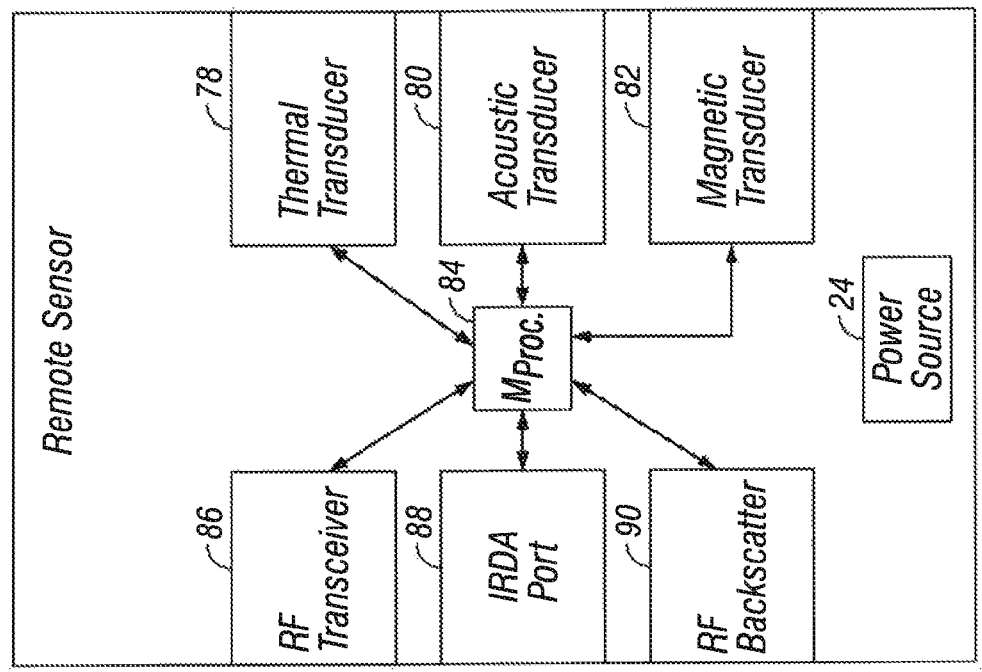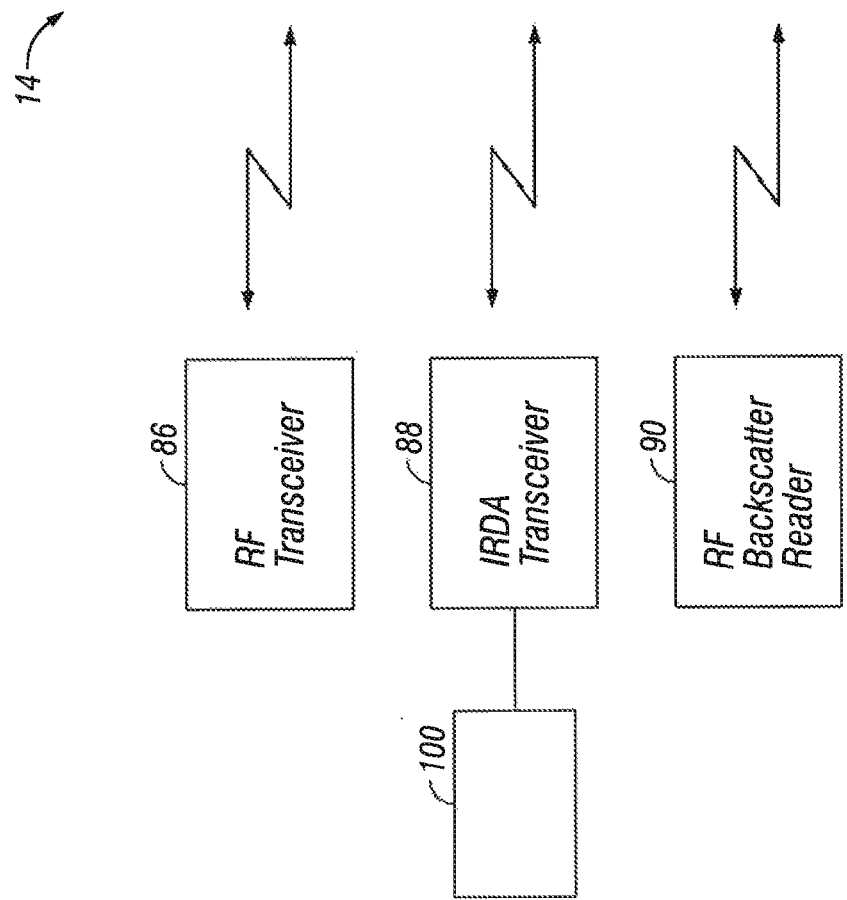
FIG. 10

ACTIVITY NAME: RUNNING

ACTIVITY DESCRIPTION: RUNNING IN MILLENIUM PARK

DATE: 5-01-07 ~306

TIME START: 2:15 pm ~308  TIME END: 3:30 PM ~310

ITEMS TO BE TRACKED: RUNNING SHOES / HEADPHONES ~312

SENSORS: RUNNING SHOES / HEART RATE MONITOR ~314

SENSOR PARAMETERS: STRIDE LENGTH = 3 FT. / HEART RATE BASELINE = 1/2 SEC. ~316

SERVICES: WEATHER ~320

FIG. 16

| ACTIVITY | ACTIVITY ID | SENSOR/ DEVICE NAME | SENSOR/ DEVICE IP ADDRESS | DATA CONFIG |
|---|---|---|---|---|
| RUNNING | 111 | SHOES 1<br>HEART | 1.23.342<br>1.23.341 | HEART RATE BASELINE 1/2s<br>OPTIMAL SAMPLING 1s<br>BASELINE ALGORITHM<br>OPTIMAL ALGORITHM<br>SHOES:<br>SAMPLING RATE;<br>BASELINE:<br>OPTIMAL SAMPLING: |
| SKATING | 112 | SKATES 1<br>JACKET | 1.23.341<br>1.23.339 | |
| WORK OUT | 113 | STAIR CLIMBER<br>TREAD MILL | 1.23.338<br>1.23.337 | HEART RATE UTILIZATION<br>CALORIES |
| COOKING/ DINNER | 116 | REFRIGERATOR<br>CABINET 2<br>CABINET 3 | 1.23.340<br>1.23.341<br>1.23.342 | CALORIES<br>FAT GRAMS<br>% UTILIZED |
| WATCH TV | 115 | TV<br>CABLE BOX | 1.23.344<br>1.23.346 | ON/OFF<br>CHANNEL |

FIG. 17B

METHODS USING A MONITORING DEVICE TO MONITOR INDIVIDUAL ACTIVITIES, BEHAVIORS OR HABIT INFORMATION AND COMMUNICATE WITH A DATABASE WITH CORRESPONDING INDIVIDUAL BASE INFORMATION FOR COMPARISON

CROSS-REFERENCE TO RELATED APPLICATIONS

This application is a continuation in part of U.S. Ser. No. 13/923,909, U.S. Ser. No. 13/923,637, U.S. Ser. No. 13/923,614, U.S. Ser. No. 13/923,809, U.S. Ser. No. 13/923,750, U.S. Ser. No. 13/923,583, U.S. Ser. No. 13/923,560, U.S. Ser. No. 13/923,543, and U.S. Ser. No. 13/923,937, all filed Jun. 21, 2013 and all of which claim the benefit of U.S. 61/772,265, U.S. 61/812,083 and 61/823,502. All of the above-identified applications are fully incorporated herein by reference.

BACKGROUND

1. Field of the Invention

The present invention is directed to methods for monitoring an individual's activates, behaviors or habits, and more particularly to methods that monitor an individual's activities, behaviors or habits and do a comparison of the monitored information with corresponding individual base information.

2. Description of the Related Art

A large number of the top health problems are either caused in whole or in part by an unhealthy lifestyle. More and more people lead fast-paced, achievement-oriented lifestyles that often result in poor eating habits, high stress levels, and lack of exercise, poor sleep habits and the inability to find the time to center the mind and relax. Recognizing this fact, people are becoming increasingly interested in establishing a healthier lifestyle.

Traditional medicine, embodied in the form of an HMO or similar organizations, does not have the time, the training, or the reimbursement mechanism to address the needs of those individuals interested in a healthier lifestyle. There have been several attempts to meet the needs of these individuals, including a perfusion of fitness programs and exercise equipment, dietary plans, self-help books, alternative therapies, and most recently, a plethora of health information web sites on the Internet. Each of these attempts is targeted to empower the individual to take charge and get healthy. Each of these attempts, however, addresses only part of the needs of individuals seeking a healthier lifestyle and ignores many of the real barriers that most individuals face when trying to adopt a healthier lifestyle. These barriers include the fact that the individual is often left to himself or herself to find motivation, to implement a plan for achieving a healthier lifestyle, to monitor progress, and to brainstorm solutions when problems arise; the fact that existing programs are directed to only certain aspects of a healthier lifestyle, and rarely come as a complete package; and the fact that recommendations are often not targeted to the unique characteristics of the individual or his life circumstances.

Individual monitoring has been accomplished by electronic monitoring and analysis. Vital signs derived from physiological waveforms a monitored and alarms generated if predetermined limits were exceeded by the vital signs. Monitoring equipment has become more complex as more physiological data is collected and more in-depth analysis of the data is required, such as calculation of vital signs and trends which required memory and processing capability.

With the introduction of monitoring units, attempts have been made to provide a measure of remote monitoring by transmitting analog waveforms of physiological data from the bedside unit to equipment at a central station such as a nurse's station. Subsequently remote monitoring efforts include analog waveforms plus digital representations for display. Both the bedside and remote monitoring activity act to give alarms upon sensing an abnormal condition and to store data and analyze data to obtain vital signs and trends. But these systems are basically one-way systems reporting physiological data from the user. There is no communication with the user as a part of an interactive integrated system.

Telemetry systems can be implemented to acquire and transmit data from a remote source. Some telemetry systems provide information about a user's activities.

It is becoming commonplace to use wireless packet data service networks for effectuating data sessions with. In some implementations, unique identifications (ID) need to be assigned to the devices in order to facilitate certain aspects of service provisioning, e.g., security, validation and authentication, et cetera. In such scenarios, it becomes imperative that no two devices have the same indicium (i.e., collision). Further, provisioning of such indicia should be flexible so as to maintain the entire pool of indicia to a manageable level while allowing for their widespread use in multiple service environments.

Medical telemetry systems may comprise an alarm adapted to identify high risk users and/or users requiring special assistance. Some medical procedures and diagnostic examinations require the removal of any telemetry system components attached directly to a user. One problem with conventional medical telemetry systems is that the process of removing telemetry system components for purposes of performing a medical procedure or diagnostic examination can generate a false alarm. False alarms unnecessarily tax hospital resources and interfere with the working environment.

There is a need for improved methods that monitor an individual's activities, behaviors or habits. There is a further need for methods that monitor an individual's activities, behaviors or habits and do a comparison of the monitored information with corresponding individual base information.

SUMMARY OF THE INVENTION

An object of the present invention is to provide improved methods that monitor an individual's activities, behaviors or habits.

Another object of the present invention is to provide methods that monitor an individual's activities, behaviors or habits and perform a comparison of the monitored information with corresponding individual base information.

A further object of the present invention is to provide methods that monitor an individual's activities, behaviors or habits and perform a comparison of the monitored information with corresponding individual base information and provide feedback.

Yet another object of the present invention is to provide methods that monitor an individual's activities, behaviors or habits and perform a comparison of the monitored information with corresponding goals set by an individual.

These and other objects of the present invention are achieved in a method for obtaining monitored information about an individual and provide the individual with feedback. A monitoring device with one or more sensors is used to measure or detect individual information selected from of at least one of, an individual's activities, behaviors and habit information, and an individual's health. The monitoring device has ID circuitry with an ID storage that contains a unique individual ID, a communication system which reads and transmits the unique individual ID from the ID storage, a power source and a pathway system. The monitoring device communicates with a telemetry system. The telemetry system has a database that includes base individual information selected from at least one of, individual physiological information, information that is indicative of the individual's activities, data indicative of one or more contextual parameters of the individual and information regarding a degree to which an individual has followed a routine.

In another embodiment of the present invention, a method is provided for obtaining monitored information about an individual and provides the individual with feedback. A monitoring device with one or more sensors is used to measure or detect individual information selected from of at least one of, an individual's activities, behaviors and habit information, and an individual's health. The monitoring device has ID circuitry with an ID storage that contains a unique individual ID, a communication system which reads and transmits the unique individual ID from the ID storage, a power source and a pathway system. The monitoring device communicates with a telemetry system. The telemetry system has a database that includes individual goals selected from at least one of, individual physiological information, information that is indicative of the individual's activities, data indicative of one or more contextual parameters of the individual and information regarding a degree to which an individual has followed a routine.

BRIEF DESCRIPTION OF THE DRAWINGS

FIG. 10 is a block diagram of a remote sensor shown in communication with two different external communication devices.

FIG. 16 illustrates one embodiment of an activity manager in one embodiment of the present invention.

DETAILED DESCRIPTION

Figure 1A:
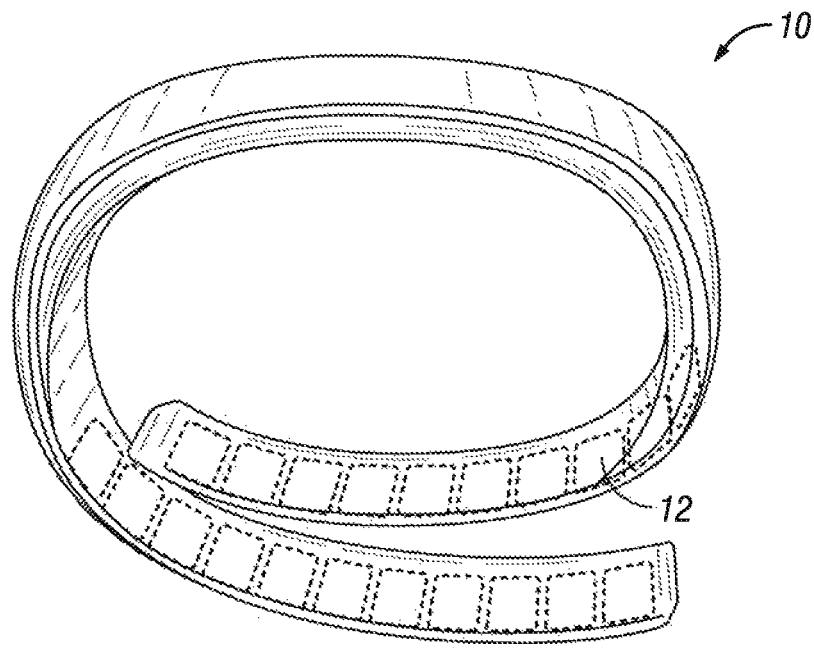
FIGS. 1(*a*) and 1(*b*) illustrate one embodiment of a wearable device of the present invention, where one size fits all.

As used herein, the term engine refers to software, firmware, hardware, or other component that can be used to effectuate a purpose. The engine will typically include software instructions that are stored in non-volatile memory (also referred to as secondary memory). When the software instructions are executed, at least a subset of the software instructions can be loaded into memory (also referred to as primary memory) by a processor. The processor then executes the software instructions in memory. The processor may be a shared processor, a dedicated processor, or a combination of shared or dedicated processors. A typical program will include calls to hardware components (such as I/O devices), which typically requires the execution of drivers. The drivers may or may not be considered part of the engine, but the distinction is not critical.

As used herein, the term database is used broadly to include any known or convenient means for storing data, whether centralized or distributed, relational or otherwise.

As used herein a mobile device includes, but is not limited to, a cell phone, such as Apple's iPhone®, other portable electronic devices, such as Apple's iPod Touches®, Apple's iPads®, and mobile devices based on Google's Android® operating system, and any other portable electronic device that includes software, firmware, hardware, or a combination thereof that is capable of at least receiving the signal, decoding if needed, exchanging information with a transaction server to verify the buyer and/or seller's account information, conducting the transaction, and generating a receipt. Typical components of mobile device may include but are not limited to persistent memories like flash ROM, random access memory like SRAM, a camera, a battery, LCD driver, a display, a cellular antenna, a speaker, a BLUETOOTH® circuit, and WIFI circuitry, where the persistent memory may contain programs, applications, and/or an operating system for the mobile device.

As used herein, the terms "social network" and "SNET" comprise a grouping or social structure of devices and/or individuals, as well as connections, links and interdependencies between such devices and/or individuals. Members or actors (including devices) within or affiliated with a SNET may be referred to herein as "nodes", "social devices", "SNET members", "SNET devices", "user devices" and/or "modules". In addition, the terms "SNET circle", "SNET group" and "SNET sub-circle" generally denote a social network that comprises social devices and, as contextually appropriate, human SNET members and personal area networks ("PANs").

A used herein, the term "wearable device" is anything that can be worn by an individual and that has a back side that in some embodiments contacts a user's skin and a face side. Examples of wearable device include but are not limited to a cap, arm band, wristband, garment, and the like.

As used herein, the term "computer" is a general purpose device that can be programmed to carry out a finite set of arithmetic or logical operations. Since a sequence of operations can be readily changed, the computer can solve more than one kind of problem. A computer can include of at least one processing element, typically a central processing unit (CPU) and some form of memory. The processing element carries out arithmetic and logic operations, and a sequencing and control unit that can change the order of operations based on stored information. Peripheral devices allow information to be retrieved from an external source, and the result of operations saved and retrieved.

As used herein, the term "Internet" is a global system of interconnected computer networks that use the standard Internet protocol suite (TCP/IP) to serve billions of users worldwide. It is a network of networks that consists of millions of private, public, academic, business, and government networks, of local to global scope, that are linked by a broad array of electronic, wireless and optical networking technologies. The Internet carries an extensive range of information resources and services, such as the inter-linked hypertext documents of the World Wide Web (WWW) and the infrastructure to support email. The communications infrastructure of the Internet consists of its hardware components and a system of software layers that control various aspects of the architecture.

As used herein, the term "extranet" is a computer network that allows controlled access from the outside. An extranet can be an extension of an organization's intranet that is extended to users outside the organization that can be partners, vendors, and suppliers, in isolation from all other Internet users. An extranet can be an intranet mapped onto the public Internet or some other transmission system not accessible to the general public, but managed by more than one company's administrator(s). Examples of extranet-style networks include but are not limited to:

LANs or WANs belonging to multiple organizations and interconnected and accessed using remote dial-up LANs or WANs belonging to multiple organizations and interconnected and accessed using dedicated lines Virtual private network (VPN) that is comprised of LANs or WANs belonging to multiple organizations, and that extends usage to remote users using special "tunneling" software that creates a secure, usually encrypted network connection over public lines, sometimes via an ISP.

As used herein, the term "Intranet" is a network that is owned by a single organization that controls its security policies and network management. Examples of intranets include but are not limited to:

A LAN

A Wide-area network (WAN) that is comprised of a LAN that extends usage to remote employees with dial-up access A WAN that is comprised of interconnected LANs using dedicated communication lines A Virtual private network (VPN) that is comprised of a LAN or WAN that extends usage to remote employees or networks using special "tunneling" software that creates a secure, usually encrypted connection over public lines, sometimes via an Internet Service Provider (ISP).

For purposes of the present invention, the Internet, extranets and intranets collectively are referred to as ("Network Systems").

As used herein, the term "user" includes but is not limited to a person, under a physician's care, interested in maintaining health, interested in maintaining a healthy lifestyle and/or physiologic balance, interested in monitoring lifestyle conditions, including but not limited to, the way a person goes about daily living including but not limited to, habits, exercise, diet, medical conditions and treatments, career, financial means, emotional status, and the like.

As used herein, the term "user monitoring" includes: (i) Cardiac monitoring, which generally refers to continuous electrocardiography with assessment of the user's condition relative to their cardiac rhythm. A small monitor worn by an ambulatory user for this purpose is known as a Holter monitor. Cardiac monitoring can also involve cardiac output monitoring via an invasive Swan-Ganz catheter (ii) Hemodynamic monitoring, which monitors the blood pressure and blood flow within the circulatory system. Blood pressure can be measured either invasively through an inserted blood pressure transducer assembly, or noninvasively with an inflatable blood pressure cuff. (iii) Respiratory monitoring, such as: pulse oximetry which involves measurement of the saturated percentage of oxygen in the blood, referred to as SpO2, and measured by an infrared finger cuff, capnography, which involves CO2 measurements, referred to as EtCO2 or end-tidal carbon dioxide concentration. The respiratory rate monitored as such is called AWRR or airway respiratory rate). (iv) Respiratory rate monitoring through a thoracic transducer belt, an ECG channel or via capnography, (v) Neurological monitoring, such as of intracranial pressure. Special user monitors can incorporate the monitoring of brain waves electroencephalography, gas anesthetic concentrations, bispectral index (BIS), and the like, (vi) Blood glucose monitoring using glucose sensors. (vii) Childbirth monitoring with sensors that monitor various aspects of childbirth. (viii) Body temperature monitoring which in one embodiment is through an adhesive pad containing a thermoelectric transducer. (ix) Stress monitoring that can utilize sensors to provide warnings when stress levels signs are rising before a human can notice it and provide alerts and suggestions. (x) Epilepsy monitoring. (xi) Toxicity monitoring, (xii) general lifestyle parameters and the like.

Additionally the present invention can be used to detect differences for a variety of blood tests, including but not limited to tests for the following: sodium, potassium, chloride, urea, creatinine, calcium, albumin, fasting glucose, amylase, carcinoembryonic antigen, glycosylated hemoglobin, hemoglobin, erythrocytes hemoglobin and the like.

In various embodiments, the present invention provides systems and methods for monitoring and reporting human physiological information, life activities data of the individual, generate data indicative of one or more contextual parameters of the individual, monitor the degree to which an individual has followed a routine and the like, along with providing feedback to the individual.

In certain embodiments, the suggested routine may include a plurality of categories, including but not limited to, nutrition, activity level, mind centering, sleep, daily activities, exercise and the like.

In general, according to the present invention, data relating to the physiological state, the lifestyle and certain contextual parameters of an individual is collected and transmitted, either subsequently or in real-time, to a site, preferably remote from the individual, where it is stored for later manipulation and presentation to a recipient, preferably over an electronic network such as the Internet. Contextual parameters as used herein means parameters relating to the environment, surroundings and location of the individual, including, but not limited to, air quality, sound quality, ambient temperature, global positioning and the like.

Figure 1B:
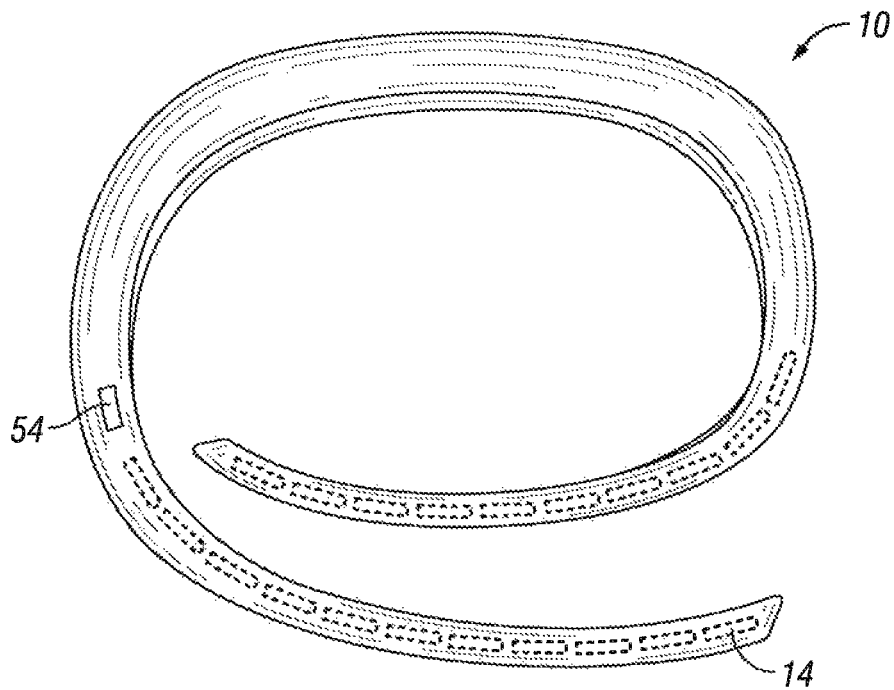

In various embodiments, the present invention provides a user monitoring device 10, including but not limited to, a wearable device, where one size fits all, Telemetry device 10 can be a sensor enabled item 10, including but not limited to a wearable device, gym bag, wallet, file, shoes, skis, and the like that has its own unique ID. As illustrated in FIGS. 1(a) and 1(b), in one embodiment of the present invention, the user monitoring device 10 include a plurality of magnets 12, with adjacent magnets having opposite polarity, with a length suitable to be worn by all people. In one embodiment, the length of the user monitoring device 10 can be 10-12 inches. The magnets 12 are positioned along an interior of the user monitoring device 10 to be provided for good conformation to a user's wrist.

One or more sensors 14 are coupled to the user monitoring device 10. The sensors are measuring devices. As a non-limiting example, the measuring device or sensors 14 can include RTSS devices to detect a user's activities, motions, physical parameters, and the like, including but not limited to, a heart rate monitor, a body temperature probe, a conventional pedometer, an accelerometer and the like.

Alternatively, multifunctional sensors 14 which can perform all the aforementioned functions of RTSS may be attached or embedded in user monitoring device 10. In one embodiment, each sensor can be in communication and or connect electronically and/or RF to a telemetry module 16. A variety of different sensors 14 can be utilized, including but not limited to, an accelerometer based sensor, and pressure based sensors, voltage resistance sensor, a radio frequency sensor, and the like, as recited above.

As a non-limiting example, an accelerometer, well known to those skilled in the art, detects acceleration and thus user activity. The accelerometer provides a voltage output that is proportional to the detected acceleration. Accordingly, the accelerometer senses vibration. This voltage output provides an acceleration spectrum over time; and information about loft time can be ascertained by performing calculations on that spectrum. A microprocessor subsystem, such as disclosed in U.S. Pat. No. 8,352,211, incorporated herein by reference, stores the spectrum into memory and processes the spectrum information to determine activity. Other examples of suitable accelerometer sensors are disclosed in EP 2428774 A1, incorporated herein by reference. Suitable pressure sensors are disclosed in EP 1883798 B1, incorporated herein by reference. A suitable voltage resistance sensor is disclosed in EP 1883798 B1, incorporated herein by reference. A suitable radio frequency sensor is disclosed in EP 2052352 B1, incorporated herein by reference.

Figure 2:
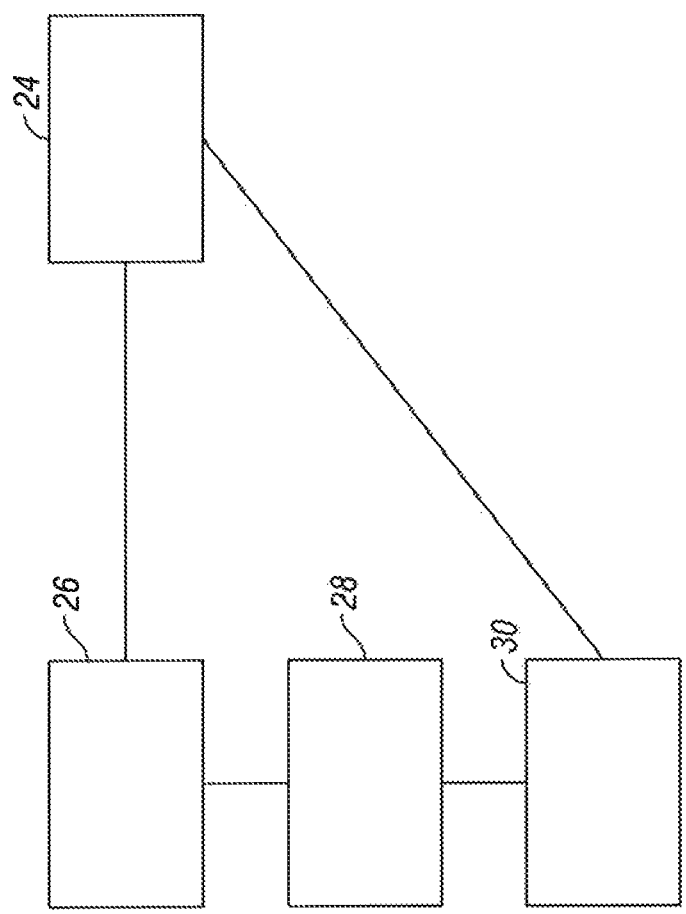
FIG. 2 illustrates one embodiment of electronics that can be included in the wearable device.

Referring to FIG. 2, in various embodiments, the user monitoring device 10, also known as the user monitoring device, can include a power source 24, such a battery that can be rechargeable. The battery 24 can be put into a sleep state when not actively used in order to preserve power. A wake up feature allows the battery 24 and other electronics of the user monitoring device 10 to "sleep" during non-use or and is initiated into the "wake up" mode by certain predestinated events.

Figure 3:
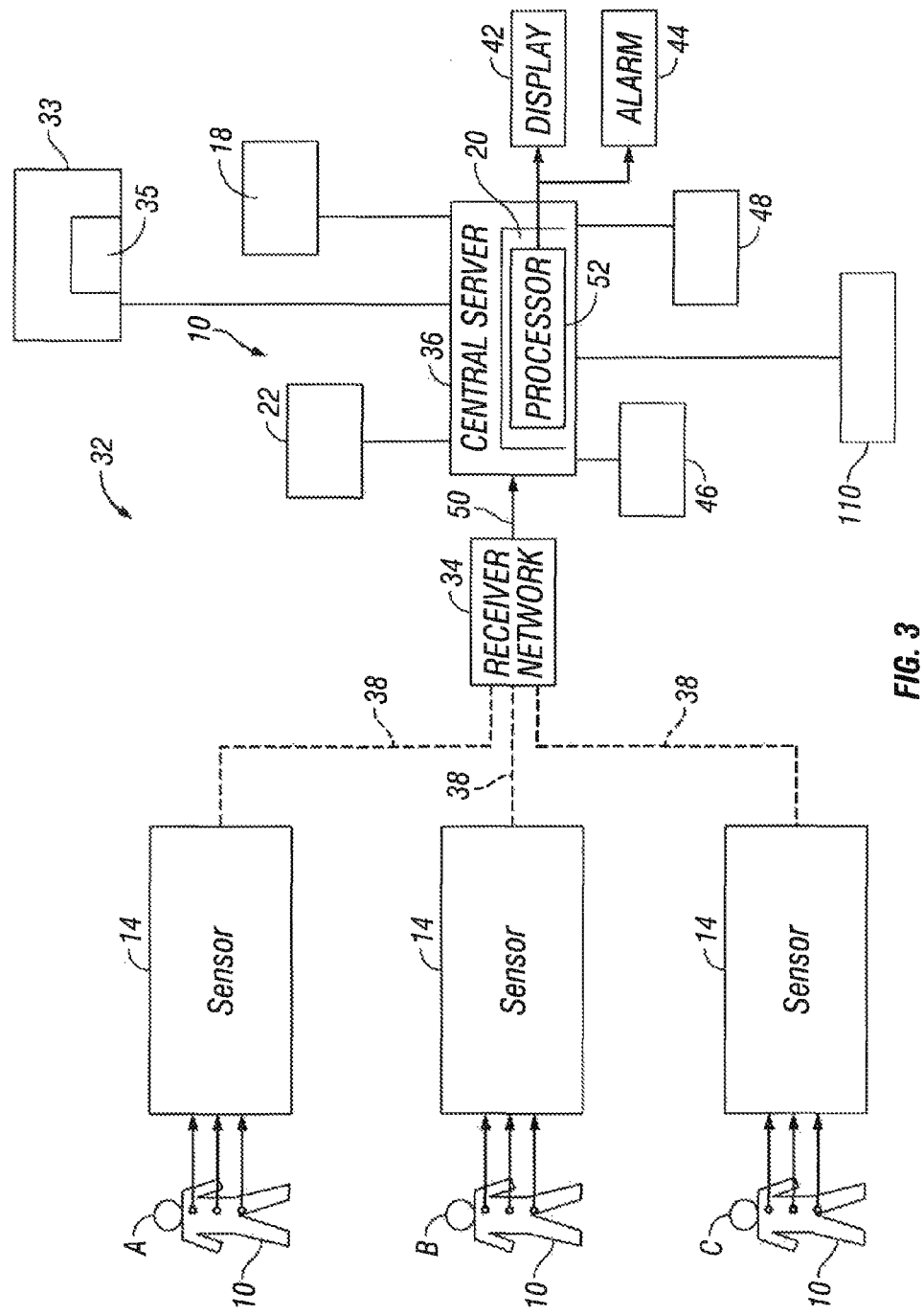
FIG. 3 illustrates one embodiment of a telemetry system of the present invention.

In one embodiment, as illustrated in FIG. 3, a telemetry system server 16 is coupled to a database 18. Each user monitoring device 10 is assigned its own unique identification, ID.

The data transmitted by the user monitoring device 10 sensors 14 and its ID may be coded by appending a seed to digital data bits. As illustrated in FIG. 3 central processor unit 20 (CPU) validates or rejects received upon detection of the seed string appended to the digital data bits. In the alternative, the digital data bits may be coded and decoded by applying a scrambling algorithm utilizing the seed. A programming device 22 may be configured to transmit data to a sensor 14, also known as a user monitoring device, utilizing a variety of alternative transmission means, including, for example, RF, IR, optical, and the like, or a magnetic loop/induction system.

In one embodiment, sensors 14 are configured to be shipped to users in a non-programmable mode with all programming already performed at the factory. A random seed may be communicated to the programming device 22 can a variety of different mechanisms, including but not limited to, via scanning a bar code, manual input, magnetic strip, random number generation, and the like.

Referring again to FIG. 2, in one embodiment, the user monitoring device 10 includes a control unit 26 that puts the user monitoring device 10 in a low power state. A monitoring system 28 can be included that remains active. The monitoring system 28 wakes up the electronics 30 in the user monitoring device 10 from a low power state. The control unit 26 can be notified of awaking of the other components by the monitoring system 28. The control unit 26 can set a status bit on the monitoring system 28 only when the battery 24 needs to be in a full power state. The control unit 26 then forces a power cycle.

Referring to FIG. 3, one embodiment of a telemetry system 32 is illustrated. The telemetry system 32 is in the communication with the sensors 14 and or user monitoring device 14 and ID of the user monitoring device 10 and can include one or more receivers 34, a central server 36 with the CPU 20. The telemetry system 32 can optionally include a display 42 and an alarm 44. The telemetry system 32 receives information from sensors 14 and or the monitoring device of a user's habits, activities, and the like, and then processes this information. Monitoring device 10 with its unique ID and sensors 14 is assigned to a specific user in order to track and/or monitor that user. For illustrative purposes assume that three users A, B AND C are being tracked and monitored by the telemetry system 32. It should, however, be appreciated that the telemetry system 32 may be implemented to track and/or monitor a much larger number of users.

In one embodiment of the present invention, radio frequency (RF) devices that are sensors 14 and/or chips may serve as the identifying devices. Each source, sensor 14, ID and the like can carry a fixed radio frequency chip encoded with identifying data which may be correlated to the individual participants, parts or objects.

Telemetry system 32 of the present invention may include a Real-Time Location System (RTLS) 46 and Real-Time Sensing System (RTSS) 48 with RF technology. The RF technology may include active and/or passive RFID sensors 14 and an RF wireless array system as a receiver 34. The RF technology in the RTLS 46 and RTSS 48 may include UWB technology (e.g., IEEE 802.15), WLAN technology (e.g., IEEE 802.11), SAW RFID positioning system technology, GPS technology, and the like.

The sensors 14 may communicate directly with each other and/or relay telemetry data directly to base receiving RF device(s) or base receivers 34. The base receivers 34 may forward the telemetry data to a base computer either through a direct link or through a Network System. Alternatively the telemetry data may be forwarded to end user devices, including but not limited to, laptops, mobile devices and the like, either directly or through a Network System. The comprehensive telemetry system 32 using RF technologies such as UWB, ZigBee, Wi-Fi, GPS data system can be utilized as described above.

The readers/antennae may be interconnected using a LAN, such as Ethernet to provide a Network System communication infrastructure for the computers and servers. Active and passive RFID sensors 14 may be employed. The active sensors 14 (RFID) may have a two-way communication function, which allows the base computer system to dynamically manage the sensors 14; vary update rates; send self-identification and telemetry data.

The active sensors 14 may employ dual-radio architecture. In one embodiment, active sensors 14 transmit radio pulses, which are used to determine precise two-dimensional or three-dimensional location and a conventional bi-directional radio, which is used as a control and telemetry channel with a sensor update rate.

The user monitoring device 10 gathers telemetry data, communicates that data to a base station, BLUETOOTH® enabled device, or smart phone and the like. From the base station, the user monitoring device 10 can receive firmware updates or via a BLUETOOTH® enabled device. The user monitoring device 10 can receive updates wirelessly. The base station can receive firmware updates from Network Systems, take telemetry data from the user monitoring device 10 and transfer it to Network Systems. Telemetry data received from the base station is analyzed by servers and presented to an end user. Any third party device can receive data from the user monitoring device 10 wirelessly and deliver information to the servers for processing.

In one embodiment, the user monitoring device 10 uses an accelerometer, gyroscope, GPS sensor, a BLUETOOTH® chip, and a heart rate monitor.

As a non-limiting example, for heart monitoring, the accelerometer, sensor 14, determines when to sample the sensors 14 and to improve the accuracy of the heart rate monitor. The gyroscope detects movement and orientation and the GPS sensor is used to determine location of the user. A BLUETOOTH® chip allows the device to connect wirelessly to other third party devices.

As a non-limiting example, a heart rate monitor 14 detects the user's heart rate in order to accurately determine the user's activity level, behavioral patterns and the like.

An Artificial Intelligence (AI) or Machine Learning-grade algorithms is used to identify the user's activities, behaviors, behaviors and perform analysis. Examples of AI algorithms include Classifiers, Expert systems, case based reasoning, Bayesian Network Systems, and Behavior based AI, Neural networks, Fuzzy systems, Evolutionary computation, and hybrid intelligent systems. A brief description of these algorithms is provided in Wikipedia and stated below.

Classifiers are functions that can be tuned according to examples. A wide range of classifiers are available, each with its strengths and weaknesses. The most widely used classifiers are neural networks, support vector machines, k-nearest neighbor algorithms, Gaussian mixture models, naive Bayes classifiers, and decision trees. Expert systems apply reasoning capabilities to reach a conclusion. An expert system can process large amounts of known information and provide conclusions based on them.

A case-based reasoning system stores a set of problems and answers in an organized data structure called cases. A case based reasoning system upon being presented with a problem finds a case in its knowledge base that is most closely related to the new problem and presents its solutions as an output with suitable modifications. A behavior based AI is a modular method of building AI systems by hand. Neural networks are trainable systems with very strong pattern recognition capabilities.

Fuzzy systems provide techniques for reasoning under uncertainty and have been widely used in modern industrial and consumer product control systems. An Evolutionary Computation applies biologically inspired concepts such as populations, mutation and survival of the fittest to generate increasingly better solutions to the problem. These methods most notably divide into evolutionary algorithms (e.g., genetic algorithms) and swarm intelligence (e.g., ant algorithms). Hybrid intelligent systems are any combinations of the above. It is understood that any other algorithm, AI or otherwise, may also be used. Examples of suitable algorithms that can be used with the embodiments of the present invention are disclosed in, EP 1371004 A4, EP 1367534 A2, US 20120226639 and US 20120225719, all incorporated fully herein by reference.

In various embodiments, the user monitoring device 10 has additional features. In one embodiment, the user monitoring device 10 changes color, via infrared LEDs, to accurately match the wearer's skin tone. This creates a seamless and more personal integration of technology into the user's daily life. In this embodiment, there is skin contact with the user monitoring device 10.

In another embodiment, the user monitoring device 10 remotely reminds and can be used to administer medications. As a non-limiting example, the user monitoring device 10 can inject adrenalin. In one embodiment, the user monitoring device 10 has sleep pattern recognition based on movement and heart rate.

In various embodiments, the user monitoring device 10 uses algorithms to determine activity type, behavioral patterns and user habits based on collected data.

In one embodiment, the user monitoring device 10 uses the accelerometer information to improve the heart rate monitor. As a non-limiting example, the user monitoring device 10 detects movement and speed. Addition of this data improves the accuracy of the heart rate monitor and corrects for any miscalculations in vibration, noise and skin color.

In one embodiment, velocity readouts and accelerometer data are used to measure when to sample heart rate. For example, if the user monitoring device 10 registers zero velocity readout, the user is probably at rest or engaged in a passive activity. Thus, the user monitoring device 10 knows not to sample heart rate. This results in conversation of time, energy and data storage.

User activity, performance and action can be based on the acceleration and angular velocity of the user monitoring device 10. In one embodiment, the user monitoring device 10 has a feature where the user monitoring device 10 authorizes third party interaction based on hand gesture, on previous interactions or patterns of behavior. As a non-limiting example, if one purchases a coke every day for the last two weeks, the user monitoring device 10 can "orders" the person another one based on the prior history.

In one embodiment, the user monitoring device 10 features near-by user monitoring device 10 recognition that provides for other user monitoring device 10 devices to be recognized within a particular vicinity and are able to share and transfer data between them. The user monitoring device 10's data analysis and feedback can be based on current or previous sensor output. The user monitoring device 10 can alert the user when to charge the user monitoring device 10 and when it is the most convenient for the user.

In various embodiments, the feedback can be provided in graphical form, be contained in one or more web pages, transmitted to the monitoring device 10, displayed or communicated by audio mechanisms and the like.

In one embodiment, the user monitoring device 10 provides feedback via color change. An outer shell of the user monitoring device 10 can use visual feedback, including but not limited to pigment or color changes to indicate changes in user behavior or to prompt changes in user behavior. In one embodiment, the user monitoring device 10 is flexible in shape. As a non-limiting example, if the user puts the user monitoring device 10 over their hand it can expand or contract, morphing to change size and shape.

In one embodiment, the user monitoring device 10 can have a sync feature for multiple bands at the same time.

In one embodiment, the user monitoring device 10 has data transfer to an external device that can be included or not included in system 32. Patient monitoring device 10 could be a data leaching device. For example, the user can relay information to someone else's device (intermediary device) to access Network Systems connected device.

In one embodiment, the user monitoring device 10 can disable the recording of one or more sensors 14 based on location, acceleration (or lack thereof) and the like.

In one embodiment, the user monitoring device 10 detects different types of transportation and activity based on sensor data. In one embodiment, user monitoring device 10 can unlock doors or cars. The user can turn it on and off. As a non-limiting example, it can be turned off by having a capacitor switch on top and bottom and is placed in a way that one couldn't accidentally turn it off. As a non-limiting example, turning it off can be done by rotating the user monitoring device 10 once.

In one embodiment, the user monitoring device 10 recognizes the wearer based on biometric information, previous data, movement pattern, and the like. In one embodiment, the user monitoring device 10 detects a new user based on an inability to match to user/usage patterns.

As non-limiting examples, a variety of different sensors 14 can be used such as, an altimeter, blood oxygen recognition, heart rate from wrist via sonar, Doppler, based on sound wave and movement, based on pressure, and the like. A pressure sensor 14 can be placed on a circulatory vessel such as a vein to detect pulse.

With the user monitoring device 10 of the present invention, mechanical actions of the user can be triggered, recognized and evaluated.

As a non-limiting example, with multiple users and wearable devices 10, a separate user monitoring device 10 ID is assigned to each of the users A, B AND C, and thereafter the assigned transmitter/monitor 14 generates user activity data and/or user tracking data. For purposes of this disclosure, monitoring data is defined to include data acquired during the process of monitoring or evaluating a predefined characteristic. The user activity data tracks data from the sensors 14 is transferred to the receivers 34 via the wireless connections 38 represented by a dashed line.

A network of receivers 34 transfers the user activity and/or tracking data to system server 16 via connection 50. System server 16 includes a processor 52 configured to process the user data in a known manner. For example, the processor 52 may convert raw user data acquired by the sensors 14 into more conveniently readable data.

As a non-limiting example, the display 42 can be implemented to graphically convey user information from system server 16 in a conveniently readable manner. As a non-limiting example, the user may be a cardiac user with user monitoring data graphically conveyed as a conventional ECG plot comprising a sequence of P-waves, a QRS complexes and a T-waves. As another example, user tracking data may be graphically conveyed as an icon superimposed onto a map to indicate the user's relative location. Alarm 44 may be included in this embodiment.

In some embodiments, system 32 ID circuitry delivers a unique ID to the wearable device from database 18. BLUETOOTH® chips can be coupled with other wearable devices 10 in the area. This data is then stored, as more fully explained in the following paragraph. The unique ID can be utilized for a variety of different applications including but not limited to payments, social networking and the like.

The ID circuitry of system 32 can include a number of system/components: unique ID storage, communication system, which reads and transmits the unique ID from the unique ID storage, battery 24 or power system that provides power to enable communication with the user monitoring device 10, a pathway system to route signals to through the circuitry, a cluster that crunches information, and a control system, to orchestrate the communication between different systems. All of these systems can be implemented in hardware, software or a combination thereof. Continuing with the telemetry system 32, sensors 14 and sensing devices are disposed on wearable devices 10 worn by users. Data, such as movement, location, speed, acceleration, and the like, can be acquired, captured and provided to system 32.

System 32 and an associated Network System can include an identification reference, including user activity, performance and reference information for each individual sensor 14 and location.

The user activity, performance metrics, data and the like captured by system 32 can be recorded into standard relational databases SQL server, and/or other formats and can be exported in real-time.

In various embodiments, the user monitoring device 10 and/or system 32 are fully sealed and have inductively charges. All communication is done wirelessly.

In one embodiment, there are no electrical contacts, physical contacts or connections with the user monitoring device 10. The user monitoring device 10 is seamless. The telemetry system 32 can include a microprocessor with CPU 20, memory, interface electronics and conditioning electronics 33 configured to receive a signal from the sensors 14. In one embodiment, all or a portion of the conditioning electronics 33 are at the user monitoring device 10.

In one embodiment, the CPU 20 includes a processor 52, which can be a microprocessor, read only memory used to store instructions that the processor may fetch in executing its program, a random access memory (RAM) used by the processor 52 to store information and a master dock. The microprocessor is controlled by the master clock that provides a master timing signal used to sequence the microprocessor 52 through its internal states in its execution of each processed instruction. In one embodiment, the microprocessor 52, and especially the CPU 20, is a low power device, such as CMOS, as is the necessary logic used to implement the processor design. The telemetry system 32 can store information about the user's activity in memory.

This memory may be external to the CPU 20 but can reside in the RAM. The memory may be nonvolatile such as battery backed RAM or electrically erasable programmable read only memory (EEPROM). Signals from the sensors 14 can be in communication with conditioning electronics 33 that with a filter 35, with scale and can determine the presence of certain conditions. This conditioning essentially cleans the signal up for processing by CPU 20 and in some cases preprocesses the information. These signals are then passed to interface electronics, which converts the analog voltage or currents to binary ones and zeroes understood by the CPU 20. The telemetry system 32 can also provide for intelligence in the signal processing, such as achieved by the CPU 20 in evaluating historical data.

In one embodiment, the actions of the user wearing the user monitoring device 10 with the unique ID can be used for different activities and can have different classifications at system 32.

The classification can be in response to the user's location, where the user spends it time, with which the user spends its time, determination of working relationships, family relationships, social relationships, and the like. These last few determinations can be based on the time of day, the types of interactions, comparisons of the amount of time with others, the time of day, a frequency of contact with others, the type of contact with others, the location and type of place where the user is at, and the like. These results are stored in database 18.

In one embodiment, the user wearing the user monitoring device 10 can access this information from any place where data is presented to the user, including but not limited to mobile devices, the WEB, applications program identifiers, and the like.

As a non-limiting example, the user monitoring device 10 communicates with a base station at system 32. The user monitoring device 10 can intelligently switch between data transfer and charging based on sensor readout. The user monitoring device 10 can represent data based on connected devices.

In one embodiment, the user monitoring device 10 has the capability of providing recommendations, popularity of locations or activities based on acquired data from the user.

In one embodiment, the user monitoring device 10 has the capability of introducing the user to other people or users based on their data and the user's data.

In one embodiment, the user monitoring device 10 can determine emotion of the user.

In one embodiment, the user monitoring device 10 uses incremental data transfer via BLUETOOTH® and the like. The user monitoring device 10 can transmit data through the inductive coupling for wireless charging. The user is also able to change the frequency of data transmission.

The user monitoring device 10 can engage in intelligent switching between incremental and full syncing of data based on available communication routes. As a non-limiting example, this can be via cellular Network Systems, WiFi, BLUETOOTH® and the like. In one embodiment, the user monitoring device 10 has data storage. As a non-limiting example, storage of telemetry data on user monitoring device 10 can be amounts up to about 16 mg.

In one embodiment, data transferred if it's in a selected proximity of a base station of system 32 or in proximity of an associated connected Network System. In one embodiment, the user monitoring device 10 has a dynamic change of data capture frequency. The user monitoring device 10 can be programmed to instantly change how often it samples any sensor 14 based upon the sensor data. Intelligent data sampling is based on sensor readout.

The user monitoring device 10 can receive firmware updates via a base station 110 of system 32. In one embodiment, the user monitoring device 10 presents analyzed data and feedback on a website. In one embodiment, the user monitoring device 10's software is based on unique human movement. The user monitoring device 10 is able to identify its wearer based on the unique patterns of movement, location check-ins and daily habits of the user.

In one embodiment, the app can be used on a mobile device, including but not limited to a smart phone and the like.

In one embodiment, a breakdown of recounting data that has been collecting is presented for analysis of that data. Observation or recommendations can be presented based on historical information and live information. The importance of the data can be based on past user behavior.

In one embodiment, the user monitoring device 10 has artificial intelligence. A wearable device processor 54 implements logic resources that exist on user monitoring device 10.

In one embodiment, user monitoring device 10 engages in the routing of user information to third parties based on predefined rules, based on system 32 analysis.

In one embodiment, user monitoring device 10 includes one or more processors 54 that implement intelligent algorithmic processing and transfer of information to third parties. Feedback can be provided to the end user that is based on visual, tactile, gesture information and the like.

Figure 4:
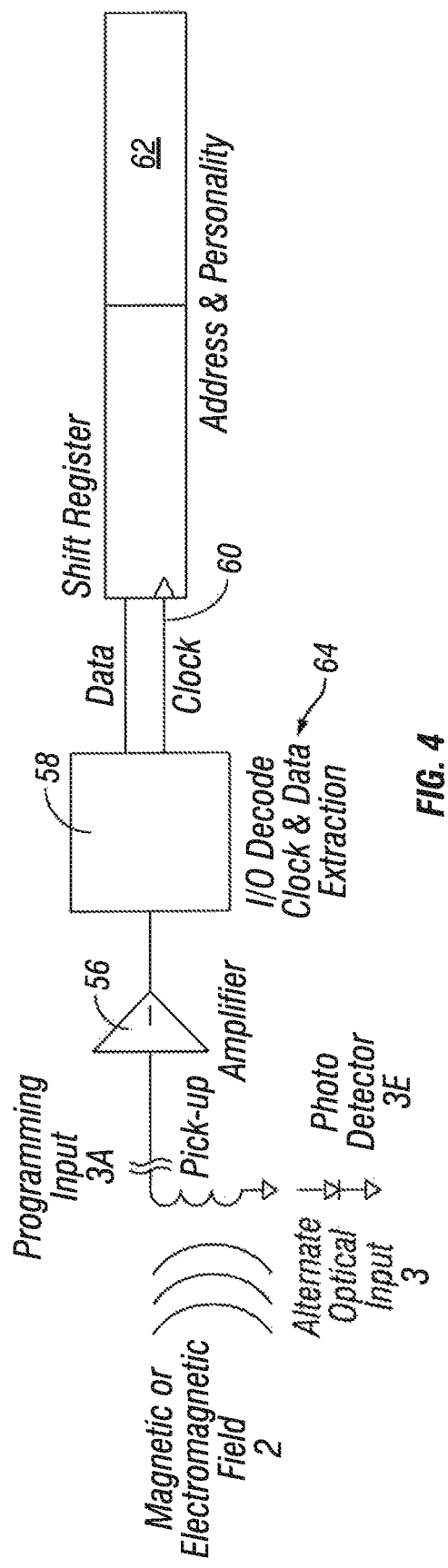
FIG. 4 is a diagram of the programming input schematic of the secure sensor/transmitter array of FIG. 7.

The ID can be sent from the user monitoring device 10 in a variety of different transmit modes, which may be provided as part of the firmware or software of an ID or sensor transmitter 14, and which may be utilized selectively during the operation of said sensor transmitter 14, may include "burst" transmit modes, wherein a burst of data information is transmitted, or "parcel" transmit modes, wherein timed data packets of data, which may, as desired, comprise partial data strings, are transmitted, and, if desired, repeated during time intervals. Further, the sensors 14 may have programmed therein diagnostic routines or other test modes which assist during manufacture and use, providing the operator with operational status and verification information on said sensor/transmitter 14, as needed. Referring to FIG. 4, system 32 includes data base 18 which contains the desired transmitter, sensor, 14 personality data, as well as, the address/device ID bits for each user monitoring device 10.

In one embodiment, the initial programming of the user monitoring device 10 for the ID, as well as optionally other personal information of the user, is done securely, as unauthorized future alteration of same thereafter can be utilized as a means of violating system integrity.

In one embodiment, an inductive field coil is used for programming the sensors 14 and ID of user monitoring device 10.

As illustrated in FIG. 4, the user monitoring device 10 can include a sensor 14 with an output that be received by an amplifier 56 and decoded by an I/O decoder 58 to determine 1/0 logic levels, as well as, both clock and data information 60. Many such methods are commonly available including ratio encoding, Manchester encoding, Non-Return to Zero (NRZ) encoding, or the like; alternatively, a UART type approach can be used. Once so converted, clock and data signals containing the information bits are passed to a memory 62. Any of these connections provides a logical link from the system's database 18 to the sensor 14, ID of the user monitoring device 10, as shown in FIG. 5.

Figure 5:
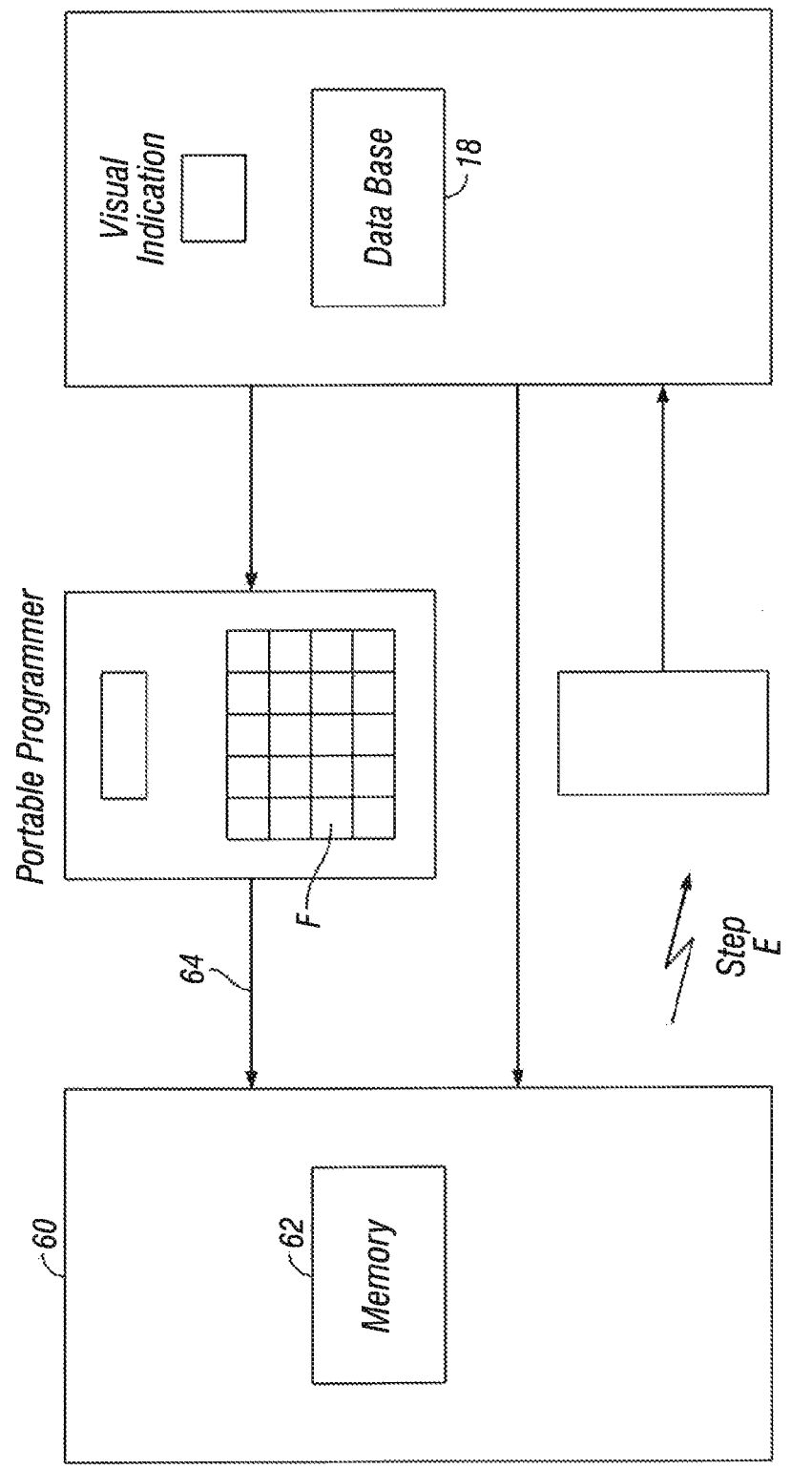
FIG. 5 is a block diagram of the system of programming the sensor/transmitter(s) comprising the secure sensor/transmitter array of FIG. 7.

In one embodiment, illustrated in FIG. 5, the system 32 chooses the necessary programmable sensor functions and stores them into database 18. In one embodiment, in order to insure that an unauthorized user cannot connect into and program user monitoring device 10 the following procedure may be used.

In one embodiment, the database 18 includes base individual information selected from at least one of, individual physiological information, information that is indicative of the individual's activities, data indicative of one or more contextual parameters of the individual and information regarding a degree to which an individual has followed a routine.

In one embodiment, the database 18 includes individual goals selected from at least one of, individual physiological information, information that is indicative of the individual's activities, data indicative of one or more contextual parameters of the individual and information regarding a degree to which an individual has followed a routine.

Both the sensor 14 and receiver 34 contain an identical, repeatable pseudo randomization algorithm in ROM or in ASIC logic.

Figure 6:
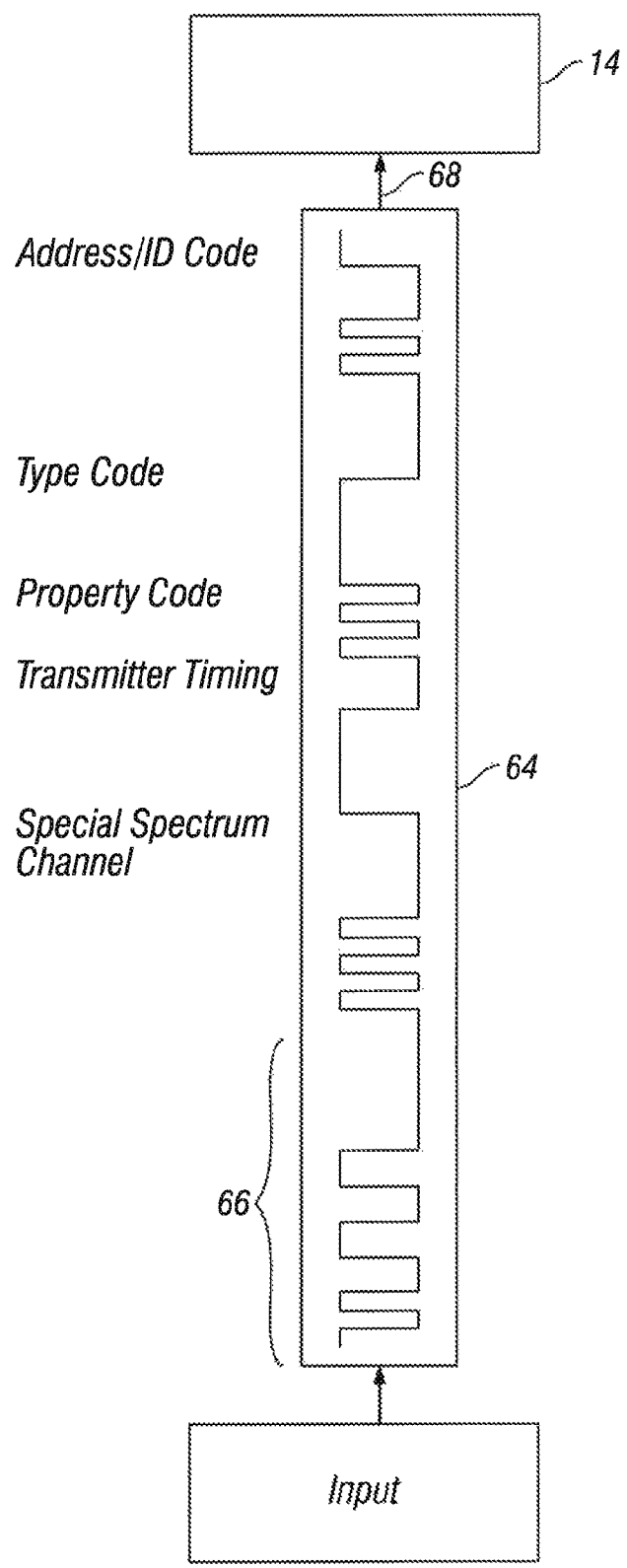
FIG. 6 is a block diagram of the jam command and security/randomization bits of the secure sensor/transmitter array of FIG. 7.

Referring to FIG. 6, the algorithm is applied to outgoing programming data 64 from system 32 and produces a number of security/randomization bits 66 that can be appended to the outgoing programming message or message 68 and sent to a sensor 14.

Figure 7:
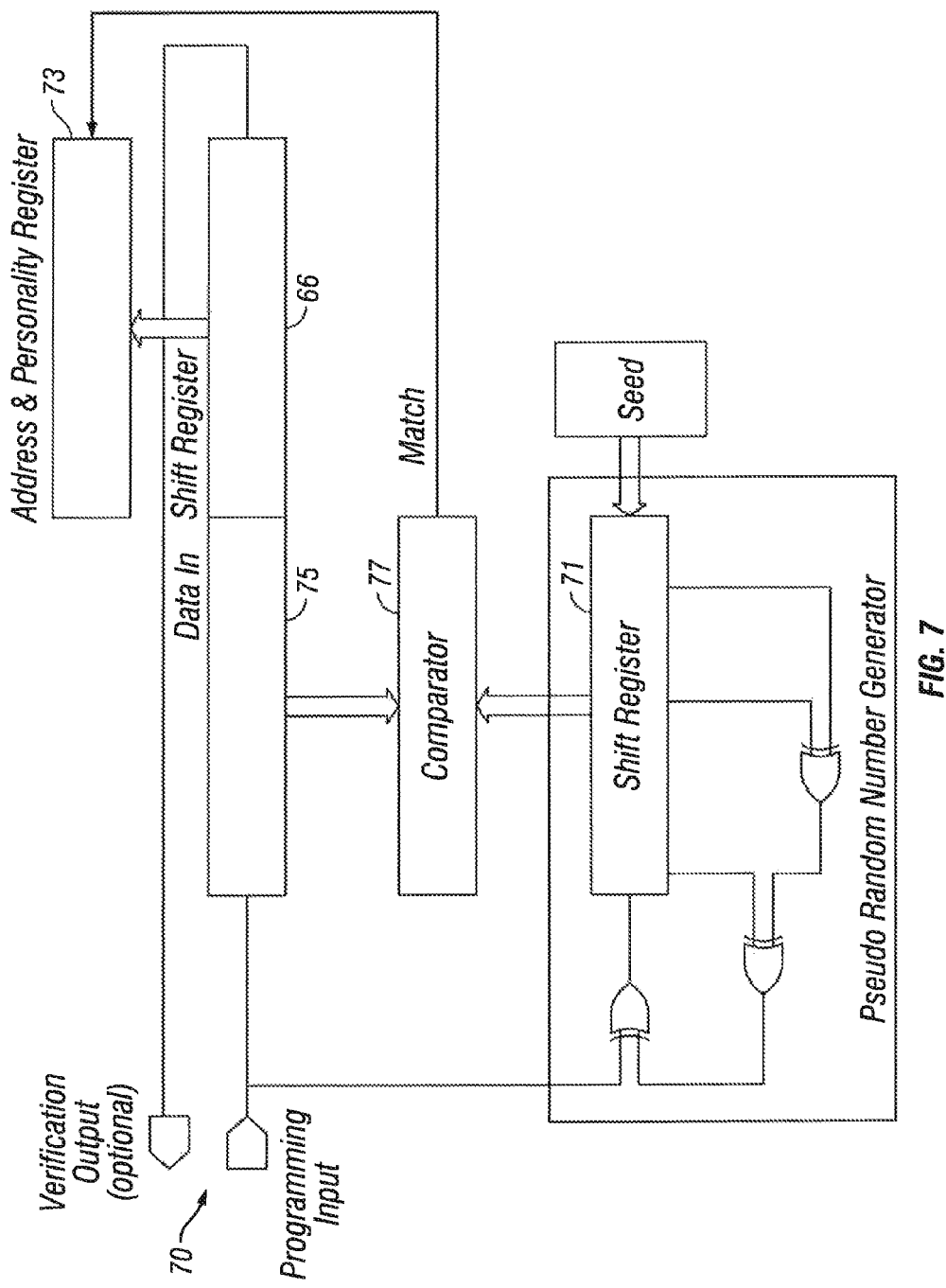
FIG. 7 is a logic circuit diagram of the sensor/transmitter programming input schematic in one embodiment of the present invention.

Referring to FIG. 7 the sensor 14 likewise applies this pseudo randomization algorithm as the security/randomization bits 66 to the outgoing programming data, now forming the incoming programming data 70 to sensor 14 and produces a several bit result in the shift register 71. The scrambling algorithm is devised such that a small difference in the programming bit stream causes a great difference in the pseudo randomization result. As a non-limiting example, the present invention can use a 16 bit polynomial to produce this pseudo randomization.

Optionally, in one embodiment, before a sensor 14 accepts this programming, stored in an address and personality register 73, both the pseudo random code, stored in data in a shift register 75 from system 32 and a sensor 14, in a shift register 71 must match via a comparator ID, 77, indicating unauthorized acceptance use. In addition to insuring authorized access, this process also insures that the data itself is correct. The longer the polynomial sequence used, the greater the security.

In one embodiment, spread spectrum or other RF transmission is used and can include programming to determine that the frequency or spread spectrum code is unique to the area. If a spread spectrum code, system code, or frequency channel is found to be occupied at a future time of use. Re-programming of the user monitoring device 10 is then done with a new, unused spread spectrum code or system code or frequency channel can be selected, or, in the alternative, CPU 20.

As illustrated in FIG. 5, step "E" would include, for example, the step of the sensor 14, inputting the programming message and saving a seed in memory 62; with the sensor 14 utilizing the seed to code digital data bits transmitted.

Figure 8:
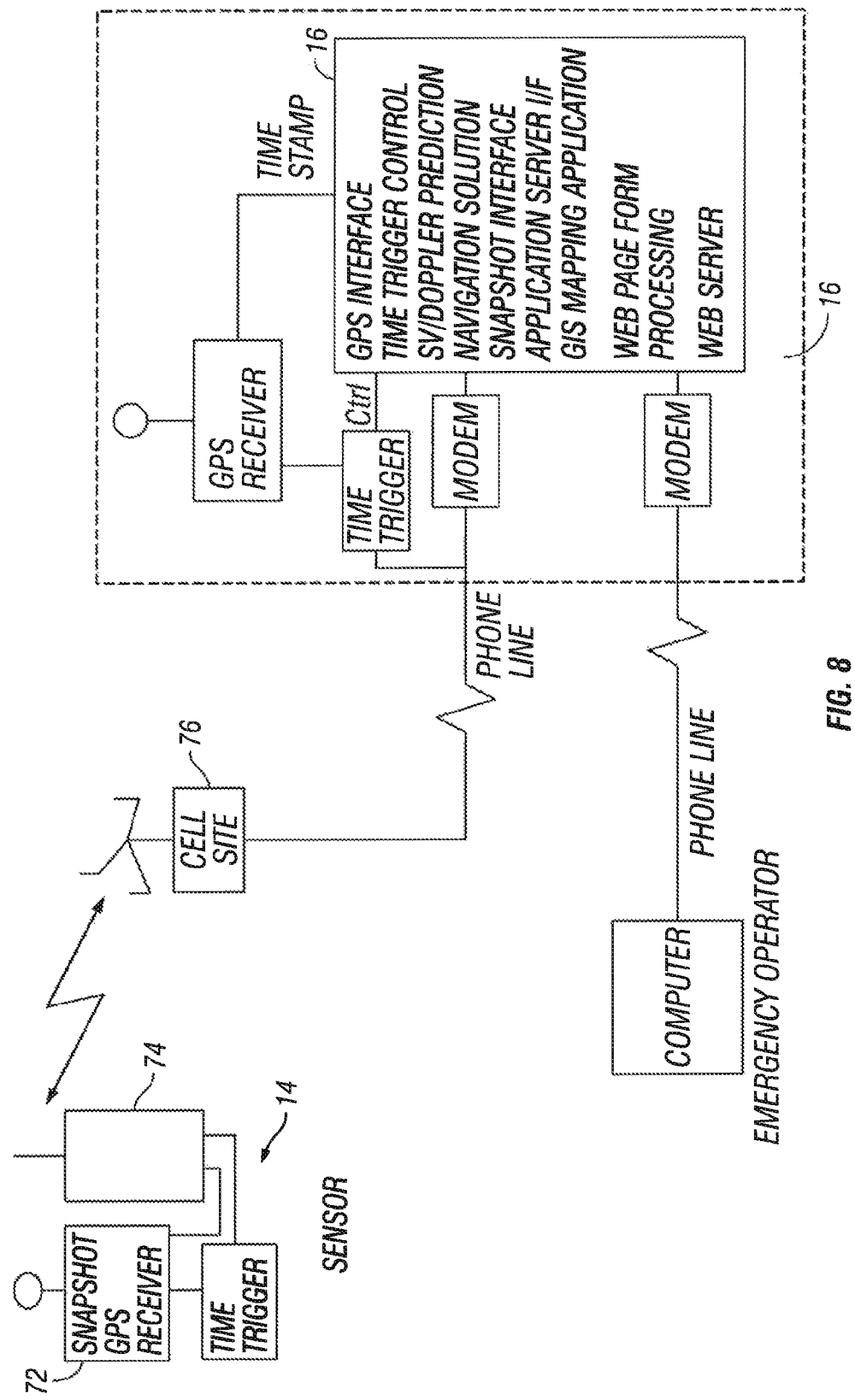
FIG. 8 is a block diagram of an embodiment of a computer implemented system for determining the location of a remote sensor utilizing the methods of the present invention.

As illustrated in FIG. 8, the location of a user monitoring device 10 with the ID and sensors 14 can be determined. As a non-limiting example, in one embodiment the user monitoring device 10 includes a sensor 14 that can provide a position signal having positioning data (e.g., raw GPD data or pseudo ranges) and the ID is transmitted from the user monitoring device 10 to system server 16. Server 16 receives the position signal and analyzes the signal to generate information representing the location of the user monitoring device 10. Server 16 transmits this location information to a client computer where the location of the user monitoring device 10, allowing a user to identify the location of the remote sensor 14.

In one embodiment, the position signal transmitted by the remote sensor 14 can also include an emergency code. For example, in the event of an emergency, such as a medical emergency or otherwise, a user may press a "panic button" that can be on the user monitoring device 10 or by use of a user's mobile device. Pressing the panic button may cause mobile device 74 to transmit an emergency signal to a cell site 76 where the emergency signal is relayed to server 16. In response, server 16 can transmit Doppler information regarding in-view satellites, a fix command and a time trigger signal to the user monitoring device 10.

When the location of the user monitoring device 10 has been determined, software running on server 16 configures server 16 such that a call or other signal is sent to a local emergency operator in the vicinity of remote sensor 14. When the call or signal is received at the emergency operator station, the location of remote sensor 14 is transmitted and displayed. In some cases, where separate panic buttons are available for identifying medical, police, fire or other types of emergencies, the nature of the emergency is also displayed for the emergency operator. Based on this information, the emergency operator can initiate an emergency response by providing the location of remote sensor 14 to the required emergency service (police, fire department, ambulance service, etc.). In other embodiments, instead of or in addition to a position report for the remote sensor 14, the emergency operator may also be provided with information which identifies an emergency response vehicle in close proximity to remote sensor 14.

Figure 9:
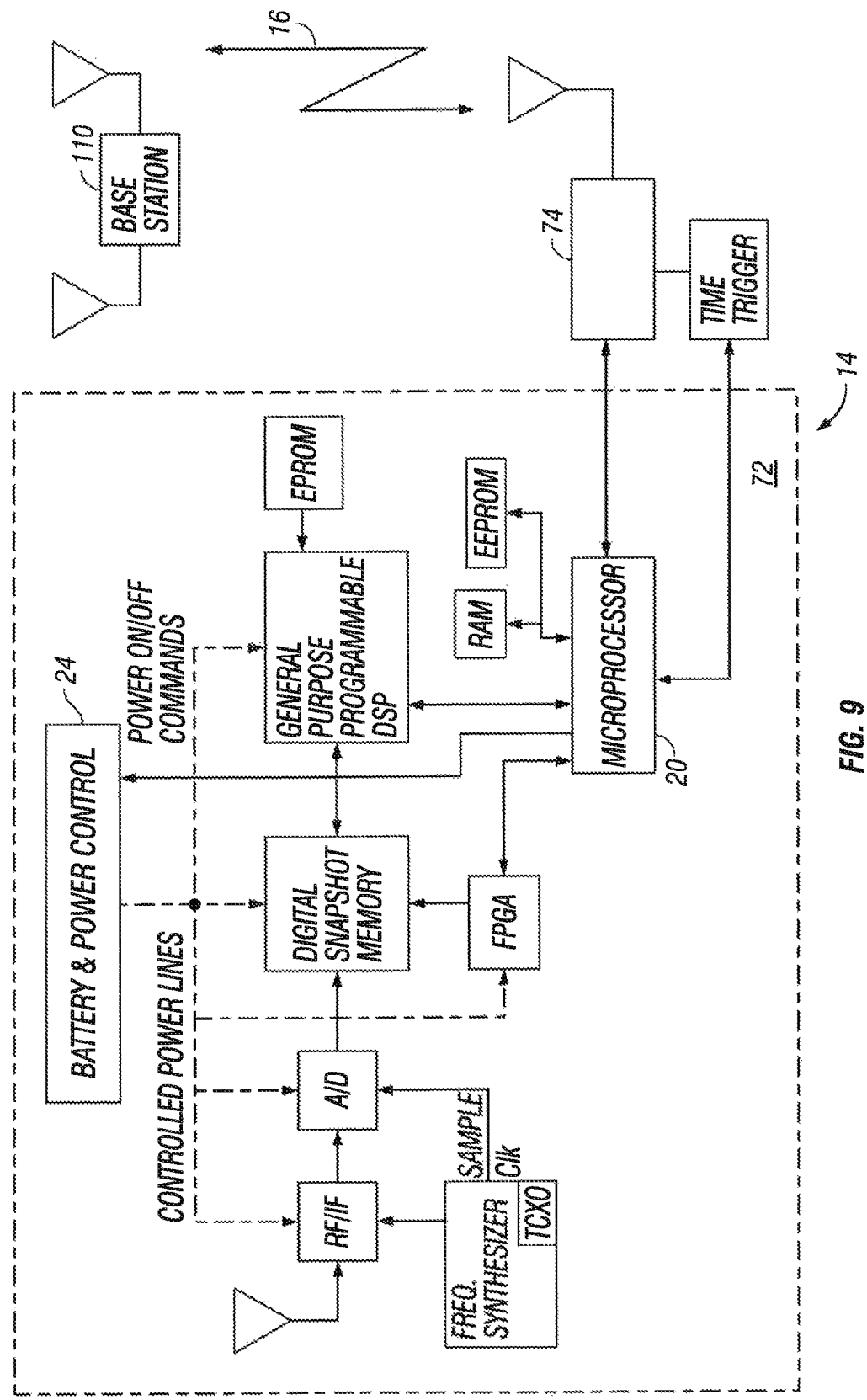
FIG. 9 is a block diagram illustrating one embodiment of a SNAPSHOT GPS receiver for use according to the present invention.

As illustrated in FIG. 9, a sensor 14 of the user monitoring device 10 can include a SNAPSHOT GPS receiver 72. As described above, sensor 14 uses information transmitted from separately located base station 110, mobile devices, computers, and other devices, to assist in determining the position of the remote sensor 14, as more fully disclosed in U.S. Pat. No. 6,661,372, incorporated herein by reference.

As non-limiting examples, and as illustrated in FIG. 10, the sensors 14 can be a thermal transducer 78, an acoustic transducer 80, and a magnetic transducer 82. It will be appreciated that the present invention is not limited The transducers 78, 80, and 82 in the user monitoring device 10 can communicate with a microprocessor 84 also located in the user monitoring device 10. The user monitoring device 10 can communicate with other devices via an RF transceiver 86, an IRDA transceiver 88, and/or an RF backscatter transceiver 90. Each of the components in the user monitoring device 10 receives power as necessary from the battery 24, which may include the rechargeable battery.

The acoustic transducer 80 may include a microphone, a low-pass filter, a gain amplifier, and a threshold comparator. The acoustic transducer 80 may include an omnidirectional microphone, although any other suitable acoustic transducer device would suffice. The microphone may be a surface mount MEMS device that has a frequency range of 100 Hz to 10 kHz. A single MCP602 operational amplifier is used on the acoustic sensor to amplify and low-pass filter the acoustic signal from the microphone. Another operational amplifier is used to generate a voltage reference used for single biasing and detection. The microphone output is biased to the midway point between the circuit supply voltage and ground to allow for both positive and negative signal swings. The biased signal is filtered with a second order low-pass Butterworth filter to remove upper frequency noise. It is then amplified with an adjustable gain that is controlled by a digital resistor potentiometer. This digital resistor operates on an I2C bus and is controlled by the microprocessor 84. Lastly, the amplified acoustic signal is threshold detected against a static voltage to detect sufficiently large acoustic signals. The digital output of the threshold detector is connected to the microprocessor 84 for processing.

The magnetic transducer 82 can include a magnetic sensor integrated circuit, a differential instrumentation amplifier, a low-pass filter, two gain amplifiers, and a threshold detector. The magnetic transducer 82 may include an NVE AA002-02 GMR (giant magneto resistive) field sensor, although any suitable magnetic sensor would suffice. This sensor has a saturation field of 15 Oe, a linear range of 0 to 10.5 Oe, and a sensitivity of 3 mV/V/Oe. Two MCP602 CMOS operational amplifiers are used on the magnetic sensor to amplify and low-pass filter the analog output signal. An INA122UA instrumentation amplifier is used as a difference amplifier for the differential output from the magnetic sensor. The magnetic sensor IC can be based on Spintronics technology. Its output includes a differential voltage pair proportional to the detected magnetic field. The differential voltage pair is amplified and converted to a single voltage by the instrumentation amplifier. The AC-coupled signal is then amplified and filtered with a low-pass filter to remove upper frequency noise and boost the low-voltage signal output. The signal is amplified a second time by an adjustable gain controlled by a digital resistor similar to the acoustic sensor. Lastly, the amplified magnetic signal is threshold detected against a static voltage, to detect sufficiently large changes in magnetic fields. The digital output of the threshold detector can be connected to the microprocessor 84 for processing.

A DS1803E-010 digitally controlled 10 kOhm variable resistor can be used in both the acoustic and magnetic sensor circuits. It is used to adjust the gain of one gain stage in each circuit. The digital resistor is controlled through an I2C interface. A LMV393IPWR comparator is also used in both the magnetic and acoustic sensor circuits for determining when a sufficiently strong sensor signal has been detected. It compares the analog sensor signal against the voltage reference and its output is tied to the microprocessor 84 for data collection.

The thermal transducer 78 may include a Burr Brown TMP 100NA/250 12-bit digital temperature sensor, although any suitable thermal sensor would suffice. The digital temperature sensor has an operating range of −55 to +120 degree C., an accuracy of 0.5 degree C. and a maximum resolution of 0.0625 degree C.

Even though it is a 12-bit sensor, suitable results are achieved with only 9-bit conversions with only the 8 most significant bits used. The sensor has an I2C interface and is normally kept in sleep mode for low power operation. When directed by the microprocessor 84, the thermal transducer can perform a 9-bit temperature conversion in 75 milliseconds.

The RF transceiver 86 may include an RF Monolithic DR3000 transceiver, although any suitable transceiver or separate transmitter and receiver 34 would suffice. This transceiver 86 allows for both digital transmission and reception. The transceiver 86 can have an operating frequency of 916.5 MHz and is capable of baud rates between 2.4 kbps and 19.2 kbps. It can use OOK modulation and has an output power of 0.75 mW. It also can use digital inputs and outputs for direct connection with the microprocessor 84. The transceiver 86 can use an antenna 92 (FIG. 11) that may include a 17 mil thick plain steel electric guitar G-string cut to a length of 8.18 cm. It is used in a monopole over ground configuration and can require a matching circuit of one inductor and one capacitor. Alternatively, Frequency Shift Keying (FSK), Quadrature Phase Shift Keying (QPSK), or any other suitable modulation scheme may be utilized.

The IRDA transceiver 88 may include a Sharp GP2W0110YPS infrared transceiver, although any suitable IRDA compliant infrared transceiver would suffice. This transceiver 88 can be IRDA v1.2 compliant and in one embodiment has an operating range of 0.7 meters. In one embodiment, it is capable of 115.2 kbps data speeds.

The RF backscatter transmission device 90 may include circuitry available from Alien Technology (of Morgan Hill, Calif.) for receiving and transmitting signals via RF backscatter. Battery 24 may be a 3.6 volt ½ AA lithium battery with a capacity of 1.2 amp hours. The battery 24 can be a power source 24 that can include a Texas Instruments TPS76930DBVT voltage regulator to regulate the output signal to 3 volts and with a maximum current of 100 mA. The voltage regulator can include a LDO.

The RF backscatter transceiver 86 in the user monitoring device 10 communicates with an RF backscatter reader 94 such as a class 3 reader from Alien Technology. The reader 94 transmits data to the backscatter transceiver 90 of the user monitoring device 10 by broadcasting encoded RF pulses and receives data back from the transceiver 86 by continually broadcasting RF energy to the sensor 10 and monitoring the modulated RF reflections from the sensor 10.

The RF backscatter transceiver 90 can include a printed circuit board (PCB) patch antenna for RF reception, and RF modulation, a Schotky diode detector circuit, a comparator circuit for signal decoding, and a logic circuit for wake-up. The logic circuit monitors the incoming data, and when an appropriate wake-up pattern is detected, it triggers the microprocessor 84 so that data reception can begin. In one embodiment, the reader 94 has an operating frequency between 2402 MHz and 2480 MHz, and uses frequency hopping in this band to reduce noise interference. A modulation method used by the reader 94 can be On-Off Keying (OOK). In one embodiment, the transmission power is 1 watt. The operation of the reader 94 may be controlled by an external computer (not shown) as directed by Labview software via a RS-232 serial link.

The RF transceiver 86 can communicate with an external RF transceiver 96 such as a DR3000 transceiver from Radio Monolithics, Inc. In one embodiment, it operates at 916.5 MHz, uses OOK modulation, has a communication range of 100 meters line of sight, and a baud rate of 19.2 kbps. The active RF antenna 92 can be a quarter-wavelength monopole made from a guitar G-string and appropriate matching circuitry. Two control lines from the microprocessor 84 can be used to select the mode of operation, choosing from transmit, receive, and sleep. The active RF receiver 34 consumes the most power in receive mode compared to the other two communication links.

FIG. 6 shows the relative positioning and shape of the active RF antenna 92 and the RF backscatter antenna 98.

The IRDA transceiver 88 of the user monitoring device 10 can communicate with an external IRDA transceiver 100 that may be identical to the IRDA transceiver 88. Alternatively, the IRDA transceiver 100 can be one such as is provided in most personal digital assistants (PDA) as well as many other consumer devices. The IRDA communication link follows the standard IRDA signal and coding protocol and is modeled after a standard UART interface. In one embodiment, the IRDA transceiver 88 is capable of data speeds less than 115.2 kbps, and may only have a range of 0.7 meters for transmission. One advantage of the IRDA communication link is that it does not require any of the RF spectrums for operation, but it typically does require line-of-sight communication.

When any one of the transceivers 86, 88 and 90 on the user monitoring device 10 detect the beginning of valid data on their respective communication link, all other transceivers are disabled, thereby preventing the corruption of incoming data with the noise or partial data packets on the other communication links. However, if the data on the active transceiver proves to be erroneous, the other transceivers will be re-enabled if appropriate to allow normal operation to continue. If the data received by the active transceiver is valid, however, the other transceivers will remain disabled for several hundred milliseconds longer in the high probability that the next data packet will be transmitted on the same communication link. If, after this extended delay, no additional packets are received, then the other transceivers will be re-enabled as appropriate.

In one embodiment, the active RF protocol has no wake-up or synchronization packets, and the packets sent to and from the sensor are identical. In one embodiment, the format of an active RF packet is shown in FIG. 16. It can include a preamble to reset and spin-up the state machine of the RF receiver 34 and to properly bias the receiver's 34 data slicer/threshold detector for optimum noise rejection and signal regeneration, two framing bits to indicate the beginning and end of the data bytes, and the data bytes themselves.

Figure 12:
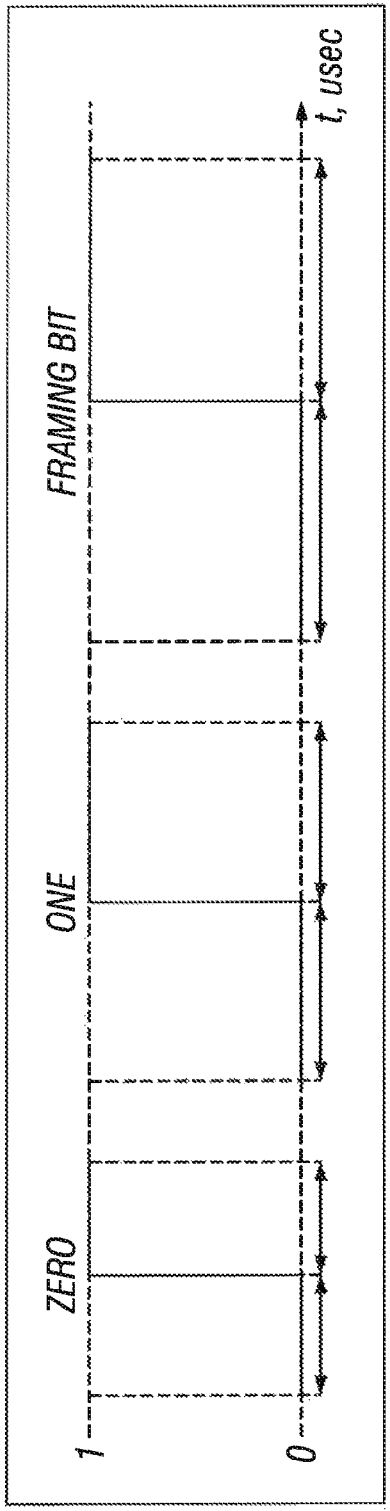
FIG. 12 is a diagram of the encoding scheme for the symbols in the active RF protocol.

Furthermore, the encoding scheme for the three symbols is shown in FIG. 12. The entire packet is DC balanced to maintain an optimal level on the data slicer/threshold detector and the receiver 34. Data is sent most significant bit first.

Figure 13:
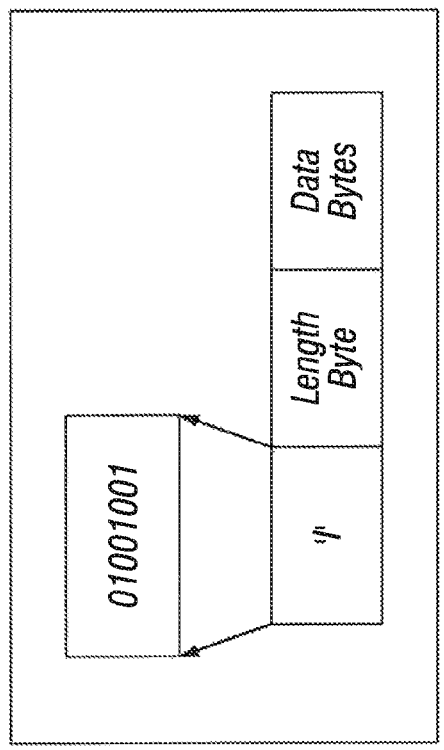
FIG. 13 is a diagram of the packet structure in the IRDA protocol.
Figure 14:
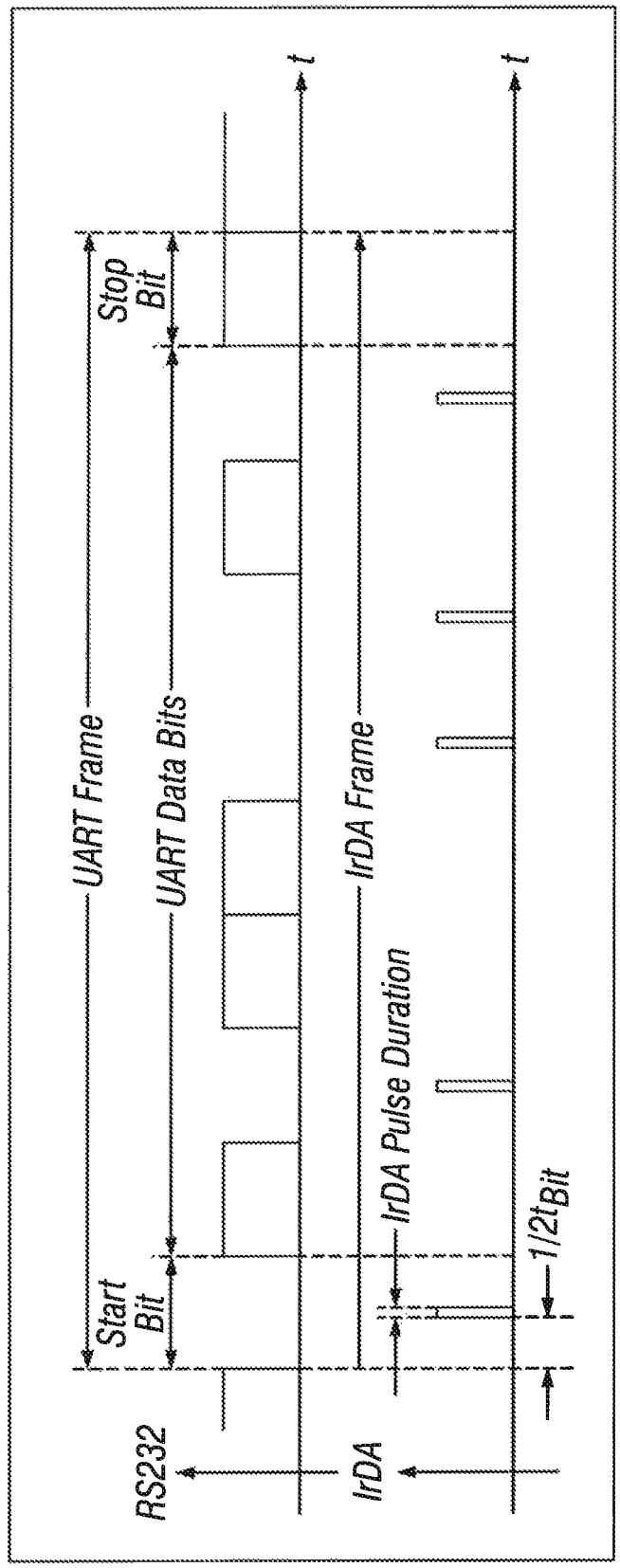
FIG. 14 is a diagram of the encoding scheme in the IRDA protocol.

The IRDA communication link can follow the standard IRDA protocol for bit encoding and UART protocol for byte transmission. Packets transmitted on the IRDA link can contain no preamble or framing bits, but they do have a header that contains two bytes. The first byte is an ASCII "I" which denotes the beginning of a valid IRDA packet. The second byte equals the number of preceding bytes in the packet. This value is used by the receiver 34 to determine when the entire packet has been received and processing of information can begin. The packet structure is shown in FIG. 13 and the IRDA/UART encoding scheme is shown in FIG. 14.

The data bytes contained in a packet transmitted to the sensor 10 through any of the communication links conform to a packet format. The CMD section of a packet is a single byte that identifies the type of packet being sent. The CMD byte appears above the beginning and end of the packet and the two must be identical. The reason for including the redundant byte is to further eliminate the chance of a packet's CMD identifier being corrupted at the receiver 34, even if the CHECKSUM is correct.

The PAYLOAD contains all of the data that must be sent to, or returned from, the sensor. The PAYLOAD is broken down into individual bytes with the overall number of bytes and their content dependent on the type of packet being sent.

The CHECKSUM is a 16-bit CRC that is performed on all bytes in the data packet excluding the end CMD byte in packets generated by the external device. The CHECKSUM is sent the most significant byte first.

The transceivers 86, 88 and 90 may be required to communicate over a greater distance than do the components described herein. Upgrading these components to be suitable for longer distance transmission is considered to be within the spirit of this invention. The type of transducer is not limited to the specific transducer types described herein. In addition, the logic described herein for arbitrating between which communication device to use to communicate with the outside world and which sensor data to provide at what time is but one possible approach to arbitration logic within such a remote sensor 10.

Figure 15:
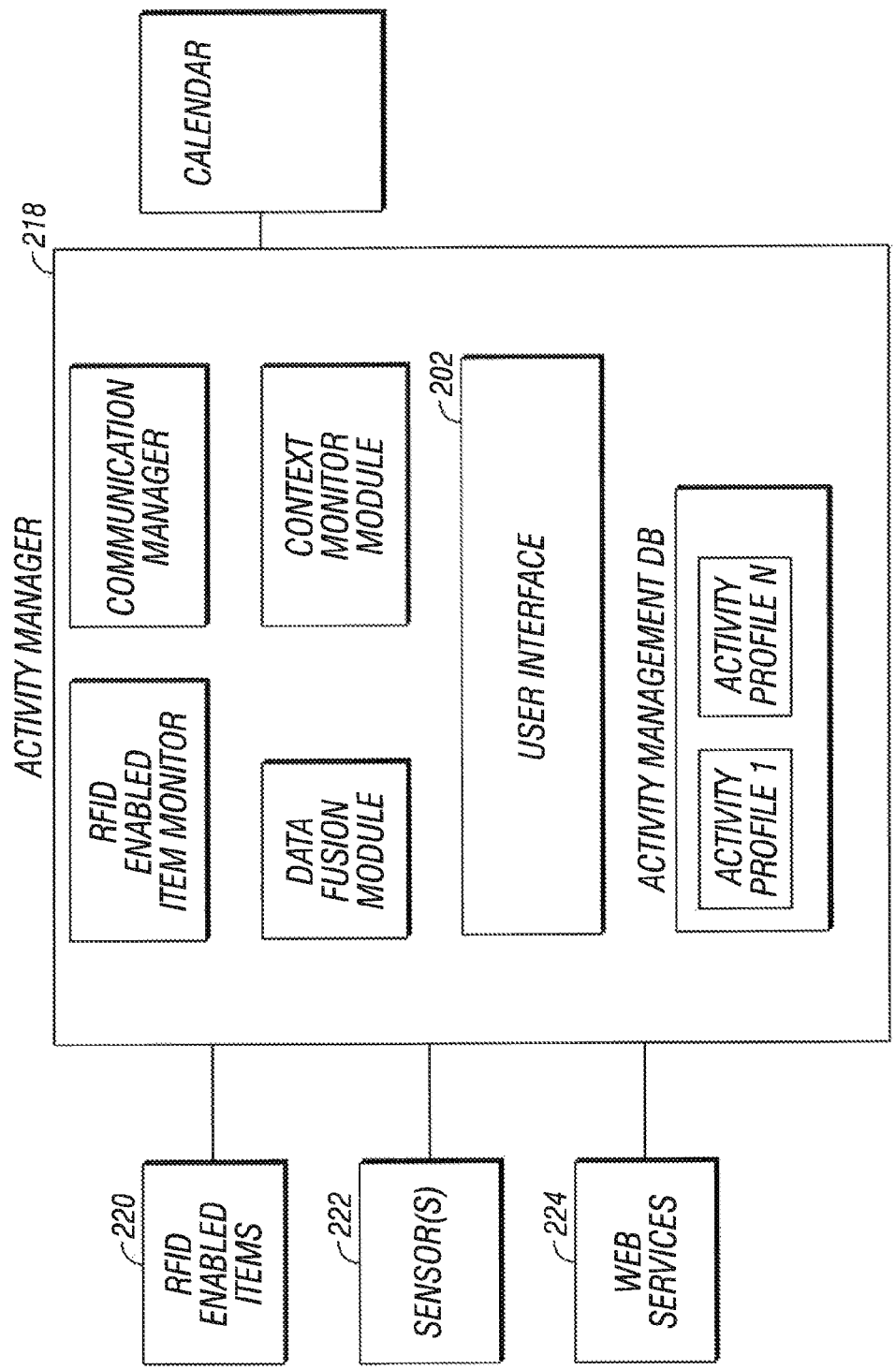
FIG. 15 illustrates one embodiment of an activity manager that is included in the monitoring device, the telemetry system or as a standalone device.

In one embodiment, illustrated in FIG. 15, an activity manager 218 is provided that is used for managing lifestyle activities of the user. Activity manager 218 can be a standalone device, or as part of the telemetry system 32 or monitoring device 10. The dynamic activity manager 218 can associate one or more contexts such as time, location, and the like to an activity entered by a user. The dynamic activity manager 218 also manages an activity and any device or item associated with the activity.

In one embodiment, the activity manager 218 communicates with the monitoring device 10 and provides information analysis of the individual information received from the monitoring device, the individual information selected from at least one of, individual physiological information, information that is indicative of the individual's activities, data indicative of one or more contextual parameters of the individual and monitoring a degree to which an individual has followed a routine. The routine includes at least one of individual, nutrition, activity level, mind centering, sleep, daily activities, exercise and the like.

In one embodiment, one or more of sensors 14 can be a lifestyle sensor. For example, the sensor 14 can be a physiological sensor such as a heart rate sensor, body temperature sensor, caloric sensor, or the like. Another example of a sensor is a pedometer. It should be noted that any sensor or device capable of taking measurements is applicable to the present invention. These sensors can be embedded, for example, in clothing and/or shoes or can be stand-alone items. One specific example of these types of sensors is a sensor that is embedded in running shoes. As a user walks or runs, the sensor 14 monitors various functions such as speed, stride length, body functions (heart rate, temperatures, hydration, and the like), and the like.

This information can then be relayed back to the dynamic activity manager 218 if desired. A web service 124 can be any type of service subscribed to by the user over the Internet. For example, a user can be subscribed to a weather service that is used by the dynamic activity manager 218 when monitoring an activity such as running. The dynamic activity manager 218, identifier enable items, including but not limited to RFID enabled items 220, sensors 14, and Network System 224 are discussed in greater detail below.

The dynamic activity manager 218 provides management for managing user lifestyle activities and is preferably included as part of the telemetry system 32. In one embodiment, the activity manager 218 is in communication to a user interface 202, which can be at the monitoring device 10, for allowing a user to enter information associated with an activity that the user wants managed and/or monitored. As a non-limiting example, FIG. 17 shows one example of the user interface 202 being displayed on the monitoring device 14. It will be appreciated the sensors can generate this information and communicate it with telemetry system. It should be noted that some fields can be automatically populated based on user activity entry, activity history, rules, or the like.

In one embodiment, a name entry field 302 can be used that allows the user to enter the name of an existing activity or the field 302 can be a drop down box including existing activities. In another embodiment, the monitoring device 10 or the telemetry system 32 can perform this activity and function.

FIG. 16 show that a user has entered the activity of "running". Therefore, the user is configuring the activity manager 218 to manage and monitor a running activity. The user interface 202 can also include an activity description field 304, which allows a user to enter a description of the activity. A date entry field 306 is also included on the user interface 202. The date field 306 allows a user to enter the date or dates when the activity is to occur. A time start field 308 and an end time field 310 are also provided in the user interface 202. The start time field 308 indicates when the activity begins and the end time field 310 indicates when the activity ends.

A user may also want the activity manager 218 to track specific items associated with the activity. For example, with respect to the running activity, a user may want to have her running shoes and headphones tracked to ensure that she has these items when she begins the activity. This information can be entered in the items to be tracked field 312. The tracking process is discussed in further detail below. The user may also want to use specific sensors 14 during the activity such as sensors 14 in the running shoes and a heart rate monitor. The sensor IDs or names can be added into the sensor field 314. A user can also configure the sensor parameters that she wants used during the activity. Alternatively, the sensor parameters can be transparent to a user. For example, the parameters can be pre-populated based on success of data collection of prior activity history. This information is entered in a sensor parameter field 316. In addition to having items tracked and sensors 14 monitored during the activity, the user may want to associate a web service with the activity.

For example, a user may want to associate a weather service with the running activity so that the activity manager 218 can automatically and dynamically adjust settings on the sensors 14; determine to track different items; and the like. For example, the activity manager 218 can monitor the web service to determine if the weather is sunny, cloudy, raining, or the like. If the weather is sunny, the activity manager may determine that a first pair of running shoes, sun glasses, and the like need to be tracked. On the other hand, if the weather is raining, the activity manager 218 can determine not to track sunglasses and to track a second pair of running shoes. It should be noted that the term "tracked" as used throughout this discussion refers to use of the ID of the monitoring device.

Alternatively, a user can setup rules that allow a web service to perform a function based on contexts. For example, if the weather is rainy, a user can have a rule setup that has a web service make a reservation at an indoor track. FIG. 16 also shows a web sensor rule(s) entry field 320. The web service field 320 allows a user to enter various rules associated with Network Systems. For example, a user can setup a web service via the web service rules field 320 to reserve a running track if the temperature outside is less than 60° F. or if it is raining.

It should also be noted that the user interface of FIG. 16 is only one example of a user interface applicable to the present invention. One or more fields may be added or deleted. For example, the user interface 218 can also provide a mechanism to a user for reviewing all entered activities, deleting activities, and the like. It should also be noted that the user interface 202 can also reside on an information processing system coupled to the monitoring device 14. For example, the activity manager 218 can have software loaded on a personal computer that allows the user to enter the above information or to interact with the activity manger 218. The activity manager 218 can then sync with database 18 to update its data. In yet another embodiment, a user can enter information directly at an identifier enabled item 220 or a sensor 14. For example, a sensor 14 can include a user interface with a calendar. Any information entered here can then be synced with the activity manager 216. Any configuration parameters such as a heart rate baseline, stride length, and the like are then communicated to the activity manager 218.

Referring again to FIG. 15, the information received from a user, for example, via the user interface 202 can also be provided to a calendar 204 residing within the monitoring device 14. Alternatively, information from the calendar 204 can also be extracted by the activity manager 218. For example, if the activity manager 218 determines that a user has entered a new activity in the calendar 204, the activity manager 218 can prompt the user to determine if the user wants the activity manager 218 to monitor and manage that activity. Although shown residing outside of the activity manager 218, the activity manager 218 can include an internal calendar for monitoring lifestyle activities. In other words, the monitoring device 14 can include a calendar and the activity manager 218 can also include an internal calendar used in conjunction with the wireless device calendar 204.

Figure 17A:
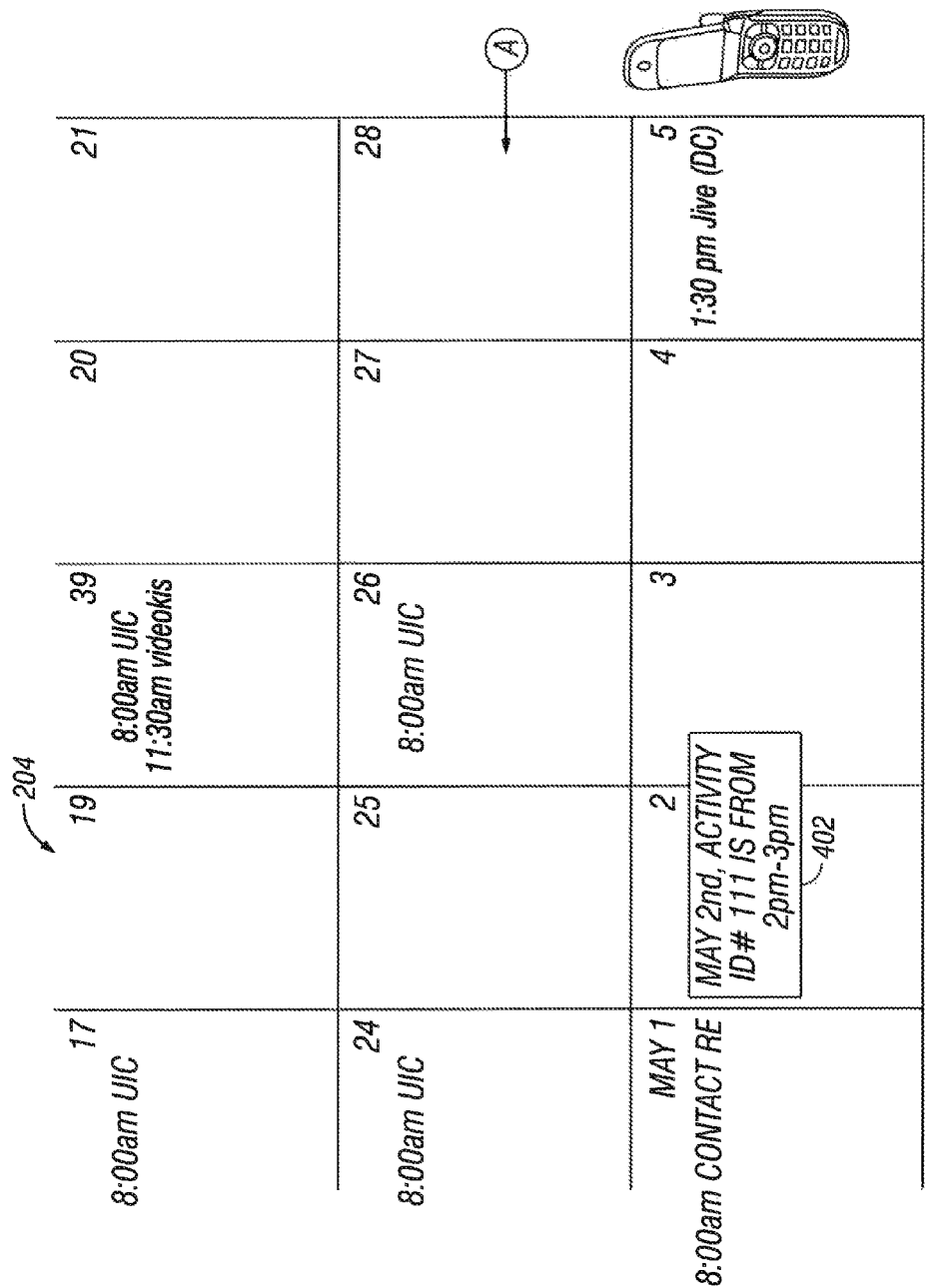
FIGS. 17(*a*) and (*b*) illustrate an exemplary user interface for an activity management application according to an embodiment of the present invention.
Figure 18:
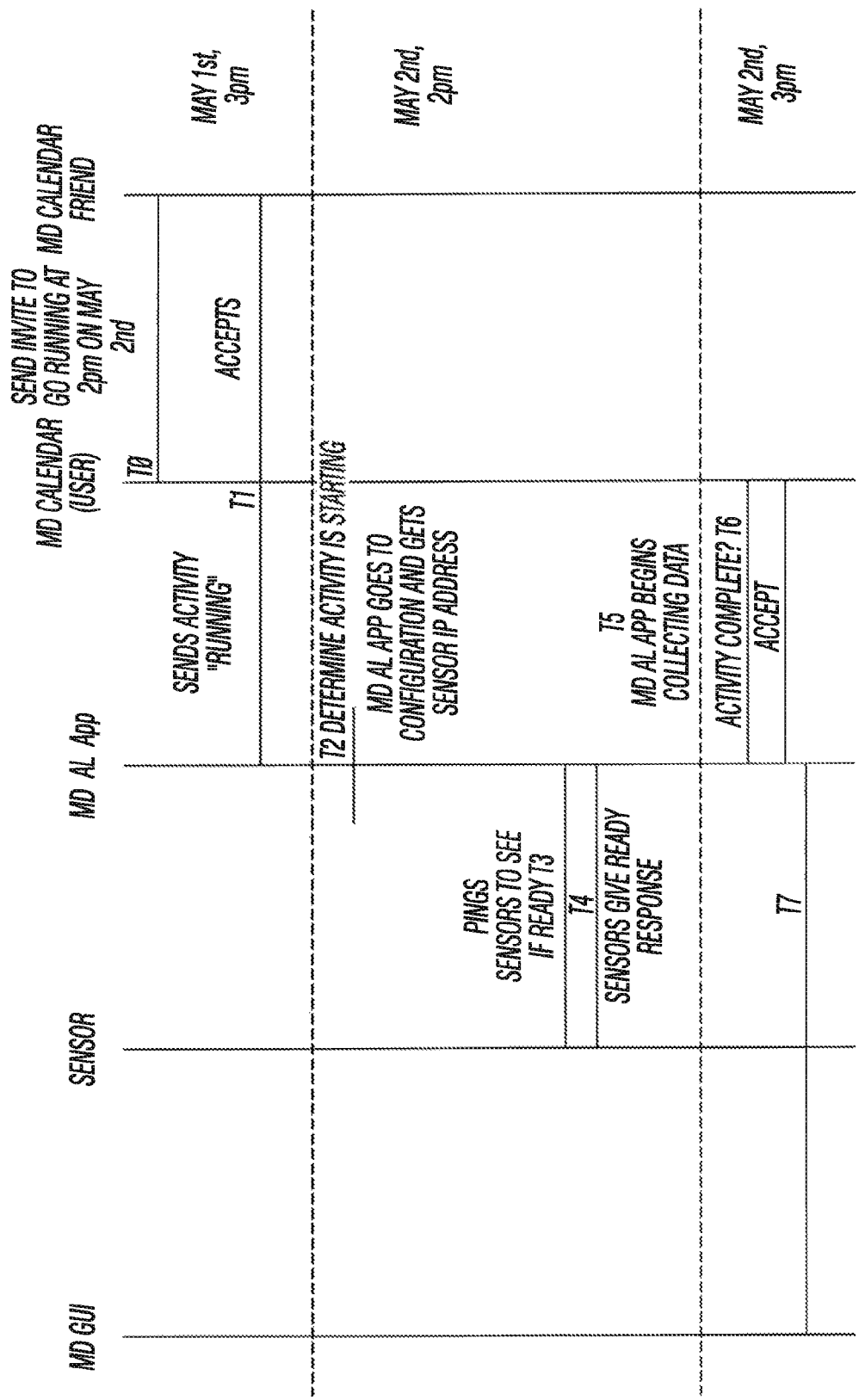
FIG. 18 is a timing diagram illustrating one example of monitoring an activity based on one or more contexts according to an embodiment of the present invention.

Based upon the received activity information, the activity manager 218 creates activity profiles 210, 212 that are stored in an activity management database 208. FIGS. 17(a) and (b) shows an example of an activity profile 210 for a variety of activities. Although FIGS. 17(a) and (b) show a single table that includes multiple activities, each activity can be stored within a separate activity profile. FIG. 18 also shows a calendar 204 comprising calendar events associated with an activity. The activity profile 210 includes various information associated with an activity such as a name 404 of an activity, an activity ID 406, a sensor or device name 408 associated with the activity, an identifier/device IP address 410 if available, data configuration 412 for the sensor/device and the like.

Also, FIGS. 17(a) and (b) show Network Systems 414 and web service rules 416 associated with a web service. For example, a web service A is associated with the "running" activity. A web service rule is associated with the web service A that indicates that if the temperature outside is less than 60° F. then reserve an indoor track. As can be seen, the activity profile associates a sensor/device context with activity. The sensor/device context indicates what sensors 14/devices or associated with the activity and their current configurations.

In the example of FIG. 18, the information within the activity profile 210 is independent of a time context or location context associated with an activity. In one embodiment, the calendar 204 associates a time context with and activity and an optional location context. For example, FIG. 18 shows a calendar event 402 set for May 2nd with a "running" activity from 2 p.m. to 3 p.m. The calendar 204 can also show the location of the activity such as "Millennium Park". Therefore, the "running" activity has a time context and a location context associated with it. The information within the activity profile 210 can be used by the activity manager 218 regardless of the time and location contexts.

For example, if the user has defined a "running" activity on two different days at two different times and at two different locations, the activity manager 218 can still refer to the "running" activity profile and use the information included therein for the two instances of the "running" activity. Therefore, the activity manger 218 monitors both the calendar 402 and the activity management database 208. However, the activity profiles 210 can also include time and location contexts as well. In this example, a separate activity profile is stored in the activity management database for each instance of an activity.

Returning now to FIG. 16, the activity manager 218 also includes a context monitoring module 210. In one embodiment, the content monitoring module 210 allows the activity manager to determine whether an activity is about to start, has started, or has ended and either monitor for identifier enabled items 220 and/or initialize sensors 14 associated with the activity. For example, the context monitoring module 210 monitors context such as time, location, device, and the like. The context monitoring module 210 can monitor the calendar 204, GPS, or information entered by the user to determine the current and/or location of the wireless device. The activity manager 218 can compare activity profiles and/or calendar events with the determined time and/or location to determine whether an activity is starting, ending, or the like.

In one embodiment, the dynamic activity manager 218 is communicatively coupled to a GPS module 246 and a display 244. The GPS module can be used by the dynamic activity manager 218 to determine the location of the monitoring device 14. The display 244 can be used for, among other things, to display data/information, visual alerts to a user.

As discussed above, the activity manager 218 manages and monitors identifier, enabled items 220, sensors 14, and Network Systems 224 associated with a user activity. identifier enabled items 220 can be any item that is coupled to an identifier or other communication tag. The activity manager 218 monitors identifier enabled items 220 via an identifier enabled item monitor 206, herein referred to as the "identifier monitor" 206. The identifier monitor 206, in one embodiment, can be an identifier transceiver embedded with monitoring software or can be a separate monitoring software module coupled to an identifier transceiver.

The identifier monitor 206 can be configured by the user to automatically start monitoring for items associated with an activity or to continuously monitor for identifier enabled items 220. For example, when the activity manager determines, based on a time context and/or a location context associated with an activity, that it is time for an activity to start, the activity manager 218 can begin monitoring for associated identifier enabled items 220. For example, if the activity manager 218 determines that the running activity is about to begin, the identifier monitor analyzes the activity profile 210 to determine what items are needed for the activity. The identifier monitor 206 then determines if items such as running shoes and heart beat monitor are present. In other words, the identifier monitor 206 determines if an identifier signal from the running shoes and the heartbeat monitor has been detected. The activity manager 218 can then visually, audibly, and/or tactilely notify the user of the presence or non-presence of the items 220.

Based on the activity profiles 210, calendar 204, and/or an internal clock the activity manager 218 can determine that the user has not left for work, to go running, or whatever the activity may be. For example, a user can have a calendar entry or an activity defined for "leave for work", which begins at 8:00 a.m. Therefore, if the time is 7:30 a.m. the activity manager 218 can determine that the user has not left for work. In another example, a user can have an activity defined for "running". The activity manager 218 can detect that the user has left the house, entered his/her car or the like either by passing an identifier sensor at a door or via GPS and analyzes the activity profiles 210 accordingly.

The activity manager 218, based on activity profiles and/or calendar events determines that the user is going straight from work to her running activity. Therefore, the activity manager 218 monitors for the items associated with the running activity. The activity manager 218 then notifies the user if these items have been protected.

In addition to monitoring for associated identifier enabled items 220 when an activity is to begin, the activity manager 218 manages sensors 14 associated with the activity. For example, when an activity is about to begin, the activity manager 218 analyzes the activity profile 210 associated with the activity and identifies the sensors 14 associated with the activity. If the sensor 14 has not been initialized, the activity manager 218 initializes the sensor 14 using the configuration parameters in the activity profile 210. For example, the sensors 14 and the monitoring device 14 can communicate via a communication manager 212 within the activity manager 218. The sensors 14 and the monitoring device 14 can communicate using a wireless connection such as BLUETOOTH®, Zigbee, or the like. In one embodiment, the dynamic activity manager also includes a data fusion module 214 for performing data fusion with respect to health and fitness information monitored by the sensors 14.

FIG. 18 shows a timing diagram for one example of initializing a sensor 14 based on the activity manager 218 detecting the start of an activity. In the example of FIG. 18, a user has a "running" activity defined on the user's monitoring device 14 and wants to invite a friend to the activity. At time T0 the activity manager 218 sends an invite associated with the "running" activity to another wireless device. The invite includes the time context, e.g., May 2nd at 2 p.m., and can include an optional location context. At time T1 the invitee wireless device sends an acceptance message to user's monitoring device 14. At time T2, the activity manager 218 determines that the time is 2:00 p.m. and queries the activity management database 208 to identify the sensors 14 associated with the "running" activity. The activity manager 218 also obtains the IP address of the sensor(s) 14. The IP address is used by the communication manager 212 to communicate with the sensor 14. In one example, the sensors 14 associated with the running activity are a sensor within running shoes that measures average speed, distance traveled, and the like. Another sensor can be a hear rate monitor worn in the wrist or an audio headset of the user.

At time T3 the activity manager 218 pings the sensors 14 to determine if they have been initialized. If the sensors 14 have not been initialized the activity manager 218 identifies that configurations parameters of the sensor from the activity profile 210 and initializes the sensors 14 accordingly. The sensors 14, at time T4, send a ready response to the activity manager 218. At time T5 the activity manager 218 begins collecting data from the sensors 14. The activity manager 218, at time T6, determines that the activity has completed. At time T7, the activity manager 218 displays collected data from the sensors 14 to the user via the user interface 202.

In another embodiment, a user can configure the activity manager 218 to only collect specific data from a sensor 14 or not all data. Also, the activity manager 218 does not have to communicate with a sensor 14 during an activity. For example, a user may have forgotten the monitoring device 10 at her house. The application manager 218 determines that an activity is starting, but sensors 14 are not in the vicinity. When sensors 14 come back into range with the monitoring device 14, e.g., the user comes home from running, the activity manager 218 queries the sensor 14 for the data collected during the activity. In one example, the sensors 14 collect data continuously and in another example the sensor 14 only collects data during scheduled activities. For example, a user's watch may have a biometric sensor that collects data throughout the day. However, the user may only be concerned with plotting data during athletic activities such as bicycling. Therefore, the activity manager 218 can query the sensor 14 for data only collected during a bicycling activity. In the above embodiments, the sensors include memory for storing data.

As illustrated in FIG. 15, the activity manager 218 can also monitor and manage Network Systems 224 associated with an activity. For example, a user can define rules associated with Network Systems 124 that are to be applied to the activity manager 218 with respect to an activity. One example is where a user subscribes to a weather service. The user can define a rule that states if the weather is rainy during the time period associated with an activity, then delay any monitoring or managing for that activity for 1 hour. Another rule can state to delay any managing or monitoring until a user prompt is received. The activity manager 218 can query the web service 124 at the start or prior to an activity starting to obtain the required information.

The activity manager 218 can also make dynamic decisions for when to monitor and/or manage an activity. For example, a user has an activity defined for "pick up dry-cleaning" at 3:00 p.m. However, at 12:00 p.m. the user runs errands and is approaching the dry cleaners. The activity manager 218 can detect the location of the user via GPS and determines that the user is near the dry cleaners. The activity manager then determines that the user needs to pick up the dry cleaning and prompts the user to pick up the dry cleaning even though the time is prior to the 3:00 p.m. scheduled pickup time.

Figure 19:
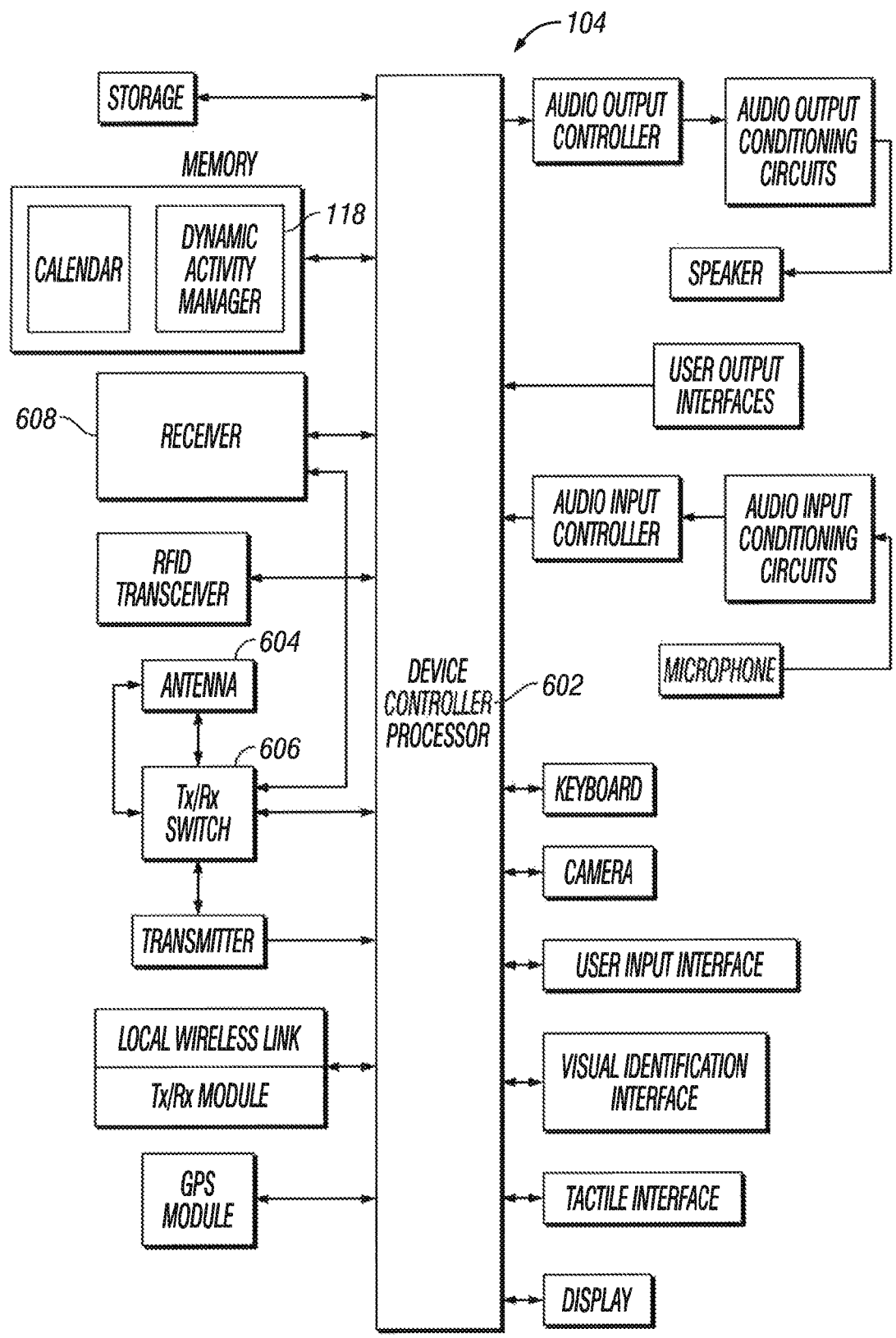
FIG. 19 is a block diagram illustrating one embodiment of a monitoring device of the present invention.

FIG. 19 is a block diagram illustrating a detailed view of the wireless device 104 according to an embodiment of the present invention. The wireless device 104 operates under the control of a device controller/processor 602, that controls the sending and receiving of wireless communication signals. In receive mode, the device controller 602 electrically couples an antenna 604 through a transmit/receive switch 606 to a receiver 608. The receiver 608 decodes the received signals and provides those decoded signals to the device controller 602.

Figure 20:
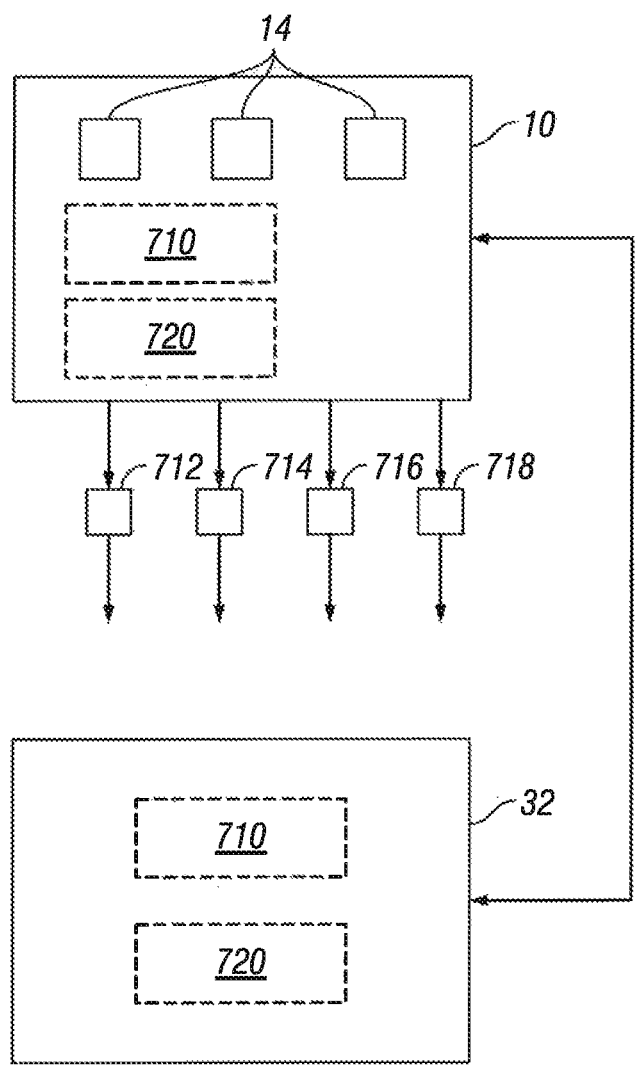
FIG. 20 illustrates an embodiment of the present invention that includes a feedback system or subsystem.

Referring now to FIG. 20, monitoring device 10 and/or telemetry system 32 can include a feedback system or subsystem 710 coupled to processor 20 and/or 34 to communicate feedback data back to the monitoring device 10. In one embodiment, the feedback system or subsystem 710 can generate and communicate closed-loop control data ("CCD") 712 to monitoring device 10. For example, closed-loop control data 712 can provide feedback to the monitoring device user or patient. It will be appreciated that feedback system or system 710 can be included in monitoring device, telemetry system 32 or be a standalone system or subsystem.

In another embodiment, feedback system or subsystem 710 can generate and communicate signals 714 for video/audio data communication to the monitoring device user or patient.

In another embodiment feedback system or subsystem 710 can generate and communicate monitoring device user or patient control data ("PCD") 716 to the monitoring device user or patient. In another embodiment, feedback system or subsystem 710 generates and communicates sensing control data ("SCD") 718 to a feedback system 720 associated with the monitoring device 10 for providing feedback to the monitoring device user or patient. Signals and data 712 through 718 can be converted into signals for executing feedback information, visual, audio and the like, to the monitoring device user or patient.

An example of feedback system or subsystem 710 includes, but is not limited to, a feedback engine installed as software and/or firmware on any type at the telemetry system 32. In one embodiment, the feedback system or subsystem 710 is at monitoring device 10 and receives feedback signals from telemetry system.

Figure 21:
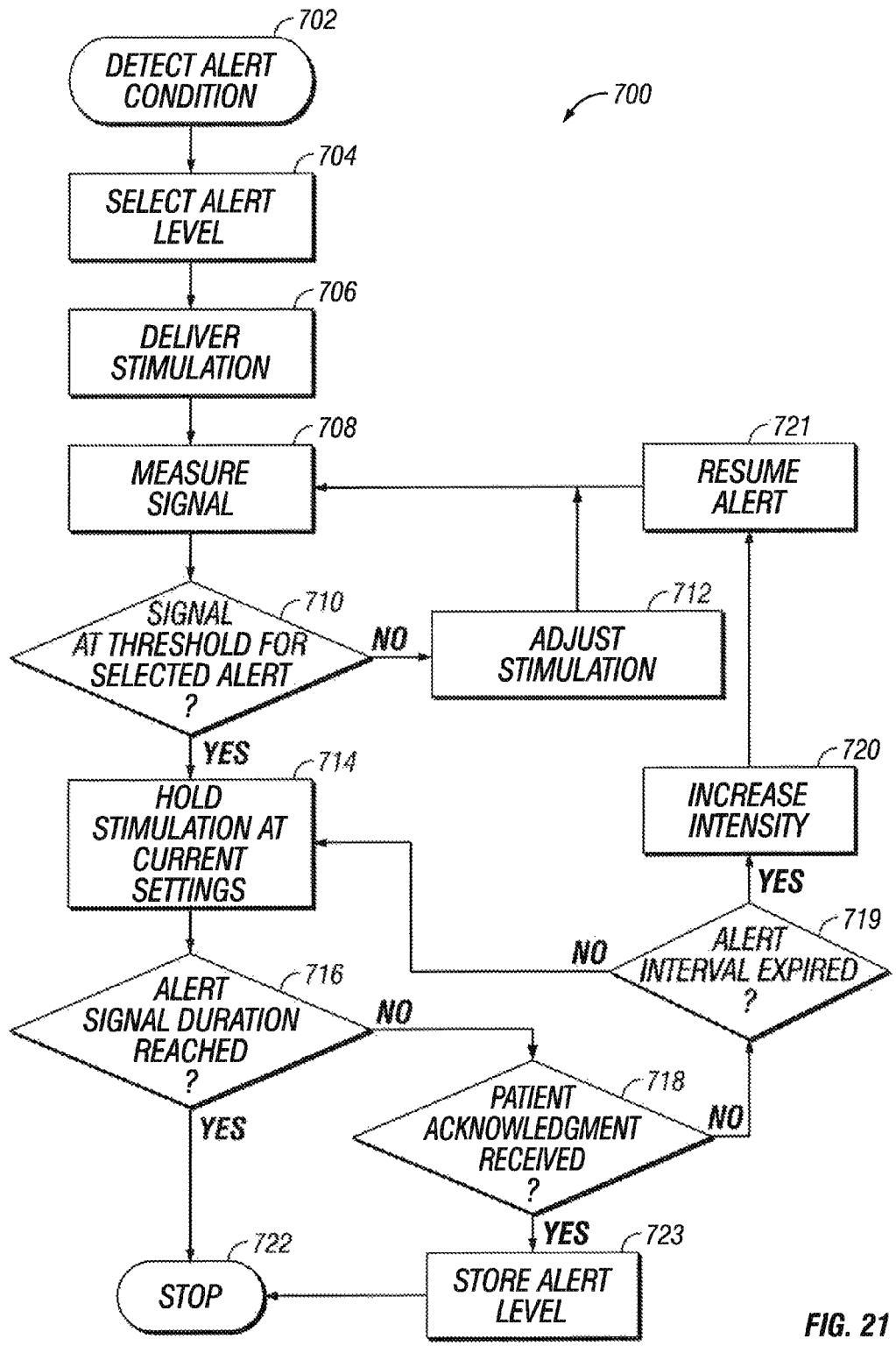
FIG. 21 is a flow chart illustrating one embodiment of proving feedback and/or alerts to a user or patient.

FIG. 21 is a flow chart 700 illustrating one embodiment of proving feedback and/or alerts to a user through or without monitoring device 10. Flow chart 700 and other flow charts presented herein are intended to illustrate the functional operation of the device feedback system or subsystem 710 and should not be construed as reflective of a specific form of software or hardware necessary to practice the methods described. It is believed that the particular form of software will be determined primarily by the particular system architecture employed in the device and by the particular detection and electrical stimulation delivery methodologies employed by the device.

At block 702, user or patient feedback is detected. Examples of feedback include but are not limited to lifestyle parameters, medical conditions, lifestyle events, exercise parameters, battery 24 life of the monitoring device 10, battery 24 replacement required, lead or sensor 14 function, pending therapy delivery, and the like. The type of feedback and alert conditions detected can vary.

At block 704, a feedback or alert is selected that is associated with a detected feedback or alert condition. Selection of a feedback or alert signal may involve the selection of any of the above listed parameters listed above relative to user or patient, used to control the feedback or alert signal. At block 706 the feedback or alert signal is delivered according to settings selected at block 704.

At block 708, a sensor 14 signal is measured at telemetry system 32 or monitoring device 10, analyzed and compared to a threshold level corresponding to the selected alert level at block 710. An alert threshold level may be predefined or tailored to a given monitoring device user or patient. If the measured sensor 14 response does not correspond to an expected threshold signal level or characteristic pattern of the selected feedback or alert signal, the feedback or alert signal is adjusted at block 712 in a closed-loop feedback method until the sensor signal measured at block 708 falls within a desired range of an expected threshold level, as determined at block 710. Once the desired feedback or alert signal level is reached, the feedback or alert signal stimulation parameters are maintained at the current settings at block 714 to maintain the sensor signal measurement within a desired range of the threshold. Maintaining the feedback or alert signal response within a desired threshold range promotes the reliability of the feedback or alert signal in informing the monitoring device user or patient of a detected parameter described above.

Determining that the sensor signal corresponds to a selected feedback or alert threshold at block 710 may involve detecting a magnitude of the a sensor signal amplitude or frequency, and/or recognizing an intended alert pattern (e.g. short-long burst sequences, strong-weak burst sequences, or the like) based on a morphology of the sensor signal. As such, measuring the sensor signal at block 708 may involve measuring signal magnitude as well as frequency characteristics during the feedback or alert signal delivery.

Additionally or alternatively, frequency characteristics of the sensor signal may be determined to detect sensor 10 signals. The frequency power band of the sensor may be analyzed for correspondence to frequency, amplitude and the like. Additionally, a sensor waveform may be evaluated for correspondence to a frequency or amplitude. A combination of the amplitude and frequency of the sensor signal may also be measured to determine a monitoring device user or patient medical or lifestyle condition.

The feedback or alert signal may be terminated if a predetermined maximum alert duration has expired, as determined at block 716. If a maximum feedback or alert signal duration is not reached, the feedback or alert signal may continue to be held at the current stimulation signal settings at block 714 until the alert expires. Alternatively, the process may return to block 708 to continue monitoring the sensor signal throughout the duration of the alert delivery in order to make further adjustments at block 712 as needed to maintain a desired strength and pattern of the monitoring device user or patient feedback or alert signal. If the feedback or alert signal maximum duration is reached, the signal may be immediately terminated at block 722.

In some embodiments, if a monitoring device user or patient acknowledgement signal is received prior to the maximum signal duration expiring, as determined at decision block 718, the feedback or alert signal is terminated at block 722. A monitoring device user or patient acknowledgment may be in a variety of forms.

In one specific embodiment, if monitoring device user or patient acknowledgement is not received or detected at block 718, the intensity of the feedback or alert signal may be increased at block 720, steadily or in step-wise, pre-determined intervals within a feedback or alert signal maximum duration. It will be appreciated that monitoring device user or patient acknowledgement is not required. The intensity may be increased at block 720 according to a predefined pattern by increasing pulse amplitude (up to some maximum), increasing pulse width, increasing pulse frequency or other adjustment that causes a relatively stronger contraction, i.e., greater recruitment of the muscle being stimulated. Adjusting the intensity of the feedback or alert signal at block 720 may also be performed using sensor signal feedback control by returning to block 708 to compare measured sensor signal characteristics to a next higher feedback or alert signal threshold level. In other words, the sensor signal is compared to a different, increased intensity, threshold than an initial threshold in order to control the feedback or alert signal to elicit a stronger response as compared to the initial feedback or alert signal settings. Thus for a given alert condition, multiple alert intensity levels may be stored in the telemetry system 32 memory along with multiple expected sensor signal responses or thresholds for each intensity level. The sensor signal is used in a closed-loop feedback method to adjust feedback or alert signal control parameters to achieve a feedback or alert signal with the desired intensity at each level.

The feedback or alert signal may be delivered continuously, with continuous or stepwise increasing intensity according to a predefined pattern, until either a maximum alert duration is reached or a monitoring device user or patient acknowledgment is received. In other embodiments, a feedback or alert signal may be delivered intermittently until monitoring device user or patient acknowledgement or expiration of a maximum feedback or alert signal duration, whichever occurs earlier. When delivered intermittently, the feedback or alert signal is delivered at an initial intensity for a predefined alert interval. The feedback or alert signal is held at the current settings at block 714 until the alert interval has expired as determined at block 719. If the alert interval expires, the intensity is increased at block 720 and the feedback or alert signal is resumed for another feedback or alert signal interval at block 721. A pause between differing feedback and alert signal intensities may be applied. As a non-limiting example, the feedback or alert signal may be delivered for a 30 second interval at an initial intensity. This process may continue until a maximum alert duration is reached as determined at block 716, or monitoring device user or patient acknowledgement is received at block 718.

As non-limiting examples, a maximum alert duration may be set at 5 minutes, 10 minutes, 30 minutes, one hour or more and may be set differently for different alert conditions, e.g. according to the seriousness of a particular alert condition. Alert intervals applied during the maximum alert duration may be set differently for different alert conditions and different alert intervals may be applied during a given maximum alert duration. For example, the alert intervals may increase in length as feedback or alert signal intensity is increased.

The same is true relative to the amplitude and duration of the alert signal.

If a maximum alert duration is not reached the alert is terminated at block 722 and optionally repeated at a later time. As described above, a maximum alert duration may correspond to a continuously delivered feedback or alert signal, which may be increased in intensity according to a predefined pattern, or an intermittently delivered feedback or alert signal that includes successive intervals of increasing intensity of the feedback or alert signal with intervening pauses of no feedback or alert signal.

In some embodiments, initial feedback or alert signal settings may be "learned" over time, based on a monitoring device user or patient's response to prior alerting attempts. When a monitoring device user or patient acknowledgement is received at block 718, the feedback or alert signal control parameters are stored at block 723. These alert settings may be used as the initial feedback or alert signal settings the next time the same alert condition is detected (or another condition using the same feedback or alert signal). These stored settings can also be used for further analysis. In one embodiment, the user or patient can provide input relative to the feedback or alert signal. This input can be used to adjust the thresholds for the alerts. In this way, if a previous alert was generated and no monitoring device user or patient acknowledgement occurred until a particular sensor signal amplitude or frequency measurement was reached, the next time the alert is generated, the alert is delivered using a lower setting at which a monitoring device user or patient acknowledgement occurred to improve responsiveness of the monitoring device user or patient to feedback or alert signals.

Adjustment of user or patient parameters at block 712, as the result of an input provided by the user or patient can be provided for maintaining a feedback or alert signal within a targeted threshold level.

The monitoring device 10 and/or the telemetry system 32 can include a feedback loop. User and patient profiles can be stored in database 18, which can include a non-volatile memory. A user or patient can input information 64 about the desired circumstances or parameters relative to a parameter that is measured by a sensor 14. The processor 20 and/or 34 can include a variety of different user and patient profiles relating to information obtained from sensors 14. The processor 20 and/or 34 can customize by either scaling or modifying the user or patient profile based on additional user or patient input information.

Furthermore, feedback or alert signals corresponding to different alert conditions may be distinguished by the monitoring device user or patient by delivering the feedback or alert signals to different body locations. When feedback or alert signals are delivered to different body locations, multiple sensors may be required in the telemetry system 32 system such that a sensor signal responsive to alert stimulation at each body location is available. Depending on the number of body locations and relative distance there between, one or more sensors may be implanted in order to provide at least one sensor in operative relation to each of the targeted alert stimulation sites.

Figure 22:
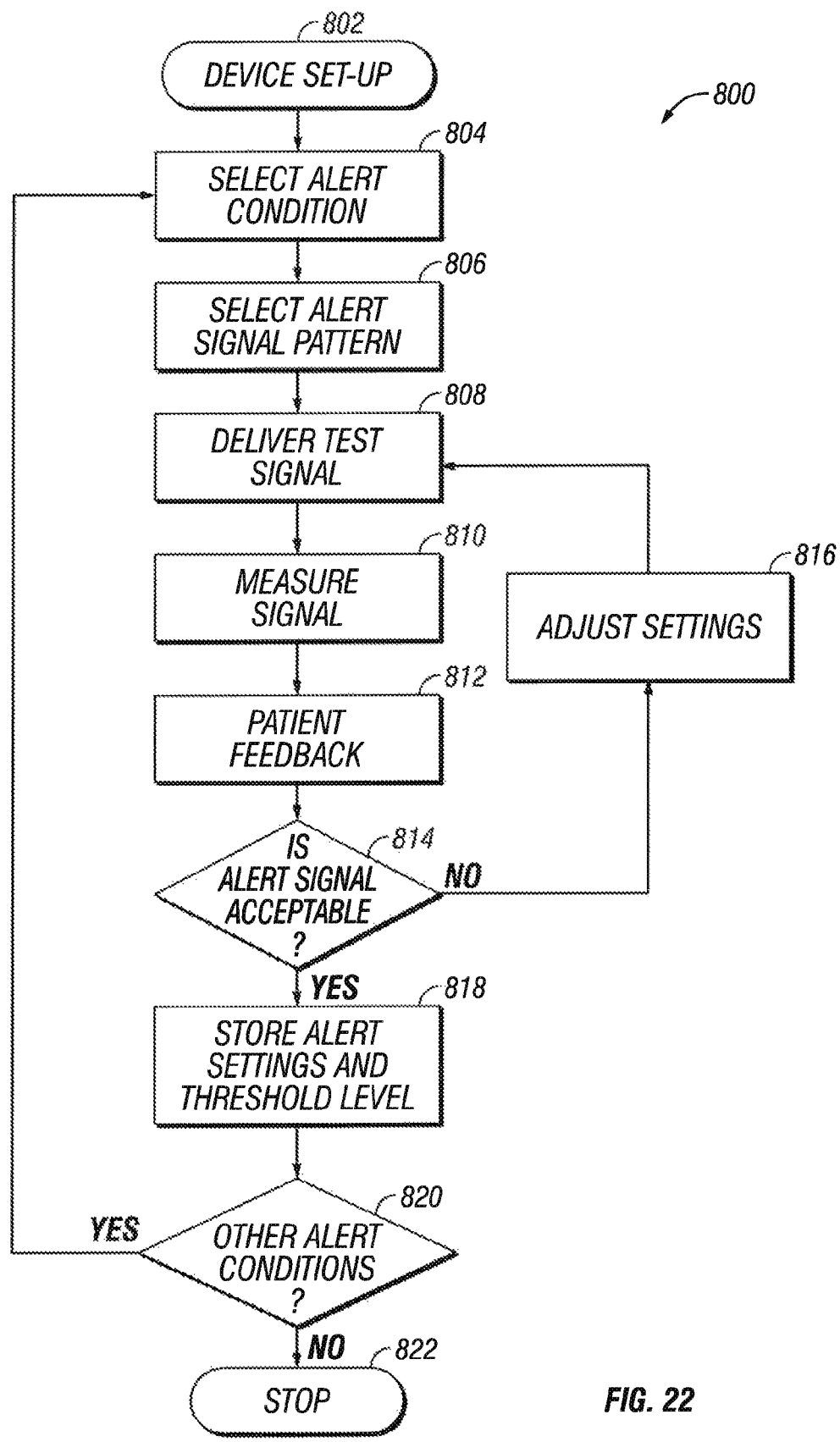
FIG. 22 is a flow chart illustrating one embodiment for a method of establishing control parameters for a monitoring device user or patient feedback or alert signal and a sensor signal threshold range for the feedback or alert signal.

FIG. 22 is a flow chart, illustrating one embodiment for a method of establishing control parameters for a monitoring device user or patient feedback or alert signal and a sensor signal threshold range for the feedback or alert signal. At block 802, a set-up procedure is initiated. In one embodiment, this can be achieved using an external programmer having a user interface. In another embodiment, information from the telemetry system database 18 that has been collected is utilized, along with any user or patient input. The process shown in flow chart 800 may be performed at any time. In one embodiment, it is done at the time the user or patient is connected to monitoring device 10. In another embodiment, it is done at a time subsequent the initial connection of the user or patient to the monitoring device 10. The process allows the establishment alert conditions and corresponding feedback or alert signals tailored to a particular monitoring device user or patient's needs. An alert condition is selected at block 804, which may be any of the parameters listed above, that receive input from a sensor 14. Alert conditions may be predefined or customized for a monitoring device user or patient.

At block 806, a feedback or alert signal pattern for the alert is selected from a person or from telemetry system database 18, and the like, which may be a default pattern for a selected alert condition or customized using any combination signals from sensors 14. Various parameters controlling the alert signal may be programmable.

Optionally, at block 808 a test signal is delivered to the monitoring device user or patient according to a selected sensor signal value. In one embodiment, the sensor signal is measured during the test signal at block 810, which may include measurements of both signal magnitude and frequency characteristics. At block 812, the patient/user may optionally provide input to establish whether the test signal is adequately perceivable and distinct from any other feedback or alert signals that have already been established. User or patient feedback may be received by a user interface included in a monitoring device 10, home monitor, device programmer, or other external device in communication with the telemetry system 32. User or patient feedback may be received by a variety of different ways known in the art when the signal is acceptable or using a signal transmitted by telemetry system 32 or monitoring device 10. A feedback or alert signal may be unacceptable to the monitoring device user or patient.

If the signal is not acceptable to the monitoring device user or patient, or not adequately measured by a sensor 14 to facilitate closed-loop feedback of the signal, as determined at block 814, one or more feedback or alert signal control parameters is adjusted at block 816, and the process at blocks 808 through 814 repeats until an acceptable feedback or alert signal is established. The feedback or alert signal settings and the sensor signal characteristic(s) associated with the acceptable feedback or alert signal are stored at block 818 to establish a threshold range of the magnitude and/or frequency characteristics of the sensor signal for the given feedback or alert signal.

If additional alert conditions can be detected by the telemetry system 32, as determined at block 820, a unique feedback or alert signal pattern can be selected for the next alert condition by returning to block 804 and repeating the process shown in blocks 804 through 818. Each alert condition may be assigned a unique monitoring device user or patient feedback or alert signal that is established by storing expected sensor signal characteristics with corresponding feedback or alert signal parameters. The monitoring device user or patient can provide feedback such that each feedback or alert signal is easily perceived, recognized and distinguished from other feedback or alert signals.

For each acceptable feedback or alert signal, a sensor threshold level is established, which may include both a magnitude component and a frequency component. The stored sensor signal thresholds allow the feedback or alert signal to be adjusted as needed during an actual monitoring device user or patient alert to most closely match the magnitude and/or frequency characteristics of the established feedback or alert signal. The monitoring device user or patient can be "trained" to recognize different feedback or alert signal patterns, intensities (strength or duration of the muscle response), and/or locations and their correspondence to different alert conditions.

Once all sensor-based threshold characteristics have been stored for all alert conditions, the process is terminated at block 822. The stored sensor signal data can then be used in a closed-loop feedback method for controlling feedback or alert signal stimulation parameters during normal operation of the telemetry system 32 as described in conjunction with FIG. 21.

As illustrated in FIG. 21, one or more analysis tools 724 at the telemetry system 32 the user information and produces analysis information that is sent to the telemetry system 32. The one or more analysis tools 724 can be part of or separate from the database 18.

The database includes base standards for at least one of user, activities, behaviors, habit information and health information that is indicative of a healthy lifestyle of activities, behaviors, habit information, exercise programs and health condition. The user information received from the monitoring device 10 is analyzed relative to the base standards in the database. In one embodiment, the base standards in operation are updatable. The update information includes updated base standards.

As set forth above, the monitoring device 10 generates data indicative of various physiological parameters of an individual, as set forth above, including but not limited to, the individual's heart rate, pulse rate, beat-to-beat heart variability, EKG or ECG, respiration rate, skin temperature, core body temperature, heat flow off the body, galvanic skin response or GSR, EMG, EEG, EOG, blood pressure, body fat, hydration level, activity level, oxygen consumption, glucose or blood sugar level, body position, pressure on muscles or bones, and UV radiation absorption. In certain cases, the data indicative of the various physiological parameters is the signal or signals themselves generated by the one or more sensors 14 and in certain other cases the data is calculated by telemetry system 32. Methods for generating data indicative of various physiological parameters and sensors to be used therefor are well known. Table 1 provides several examples of such well known methods and shows the parameter in question, the method used, the sensor device used, and the signal that is generated. Table 1 also provides an indication as to whether further processing based on the generated signal is required to generate the data.

TABLE 1

| Parameter | Method | Sensor | Signal | Processing |
|---|---|---|---|---|
| Heart Rate | EKG | 2 Electrodes | DC Voltage | Yes |
| Pulse Rate | BVP | LED Emitter and Optical Sensor | Change in Resistance | Yes |
| Beat-to-Beat Variability | Heart Rate | 2 Electrodes | DC Voltage | Yes |
| EKG | Skin surface potentials | 3-10 electrodes | DC Voltage | No |
| Respiration Rate | Chest Volume change | Strain Gauge | Change in Resistance | Yes |
| Skin Temperature | Surface temperature probe | Thermistors | Change in Resistance | Yes |
| Core Temperature | Esophageal or rectal probe | Thermistors | Change in Resistance | Yes |
| Heat Flow | Heat Flux | Thermopile | DC Voltage | Yes |
| Galvanic Skin Response | Skin Conductance | 2 Electrodes | Change in Resistance | No |
| EMG | Skin surface potentials | 3 electrodes | DC Voltage | No |
| EEG | Skin surface potentials | Multiple electrodes | DC Voltage | Yes |
| EOG | Eye Movement | Thin film piezoelectric sensors | DC Voltage | Yes |
| Blood Pressure | Non-invasive Korotkuff sounds | Electronic sphygromarometer | Change in Resistance | Yes |
| Body Fat | Body impedance | 2 active electrodes | Change in Resistance | Yes |
| Activity in Interpreted G shocks per minute | Body movement | Accelerometer | DC Voltage, capacitance changes | Yes |
| Oxygen Consumption | Oxygen update | Electro-chemical | DC Voltage Change | Yes |
| Glucose Level | Non-invasive | Electro-chemical | DC Voltage Change | Yes |
| Body position (e.g. supine, erect, sitting) | N/A | Mercury switch | DC Voltage Change | Yes |
| Muscle pressure | N/A | Thin film piezoelectric sensors | DC Voltage Change | Yes |
| UV Radiation Absorption | N/A | UV Sensitive photo cells | DC Voltage Change | Yes |

The types of data listed in Table 1 are intended to be examples of the types of data that can be generated by monitoring device 10. It is to be understood that other types of data relating to other parameters can be generated by sensor device 10 without departing from the scope of the present invention.

Telemetry system 32 can be programmed to summarize and analyze the data. For example, processor 18 or 34 can be programmed to calculate an average, minimum or maximum heart rate or respiration rate over a defined period of time, such as ten minutes. Monitoring device 10 may be able to derive information relating to an individual's physiological state based on the data indicative of one or more physiological parameters. Processor 18 or 34 can be programmed to derive such information using known methods based on the data indicative of one or more physiological parameters. Table 2 provides examples of the type of information that can be derived, and indicates some of the types of data that can be used therefor.

TABLE 2

| Derived Information | Data Used |
|---|---|
| Ovulation | Skin temperature, core temperature, oxygen consumption |
| | Beat-to-beat variability, heart rate, pulse rate, respiration rate, skin temperature, core temperature, heat flow, galvanic skin response, EMG, EEG, EOG, blood pressure, oxygen consumption |
| Sleep onset/wake | Beat-to-beat variability, heart rate, pulse rate, respiration rate, skin temperature, core temperature, heat flow, galvanic skin response, EMG, EEG, EOG, blood pressure, oxygen consumption |
| Calories burned | Heart rate, pulse rate, respiration rate, heat flow, activity, oxygen consumption |
| Basal metabolic rate | Heart rate, pulse rate, respiration rate, heat flow, activity, oxygen consumption |
| Basal temperature | Skin temperature, core temperature |
| Activity level | Heart rate, pulse rate, respiration rate, heat flow, activity, oxygen consumption |
| Stress level | EKG, beat-to-beat variability, heart rate, pulse rate, respiration rate, skin temperature, heat flow, galvanic skin response, EMG, EEG, blood pressure, activity, oxygen consumption |
| Maximum oxygen consumption rate | EKG, heart rate, pulse rate, respiration rate, heat flow, blood pressure, activity, oxygen consumption |

TABLE 2-continued

| Derived Information | Data Used |
| --- | --- |
| Rise time or the time it takes to rise from a resting rate to 85% of a target maximum | Heart rate, pulse rate, heat flow, oxygen consumption |
| Time in zone or the time heart rate was above 85% of a target maximum | Heart rate, pulse rate, heat flow, oxygen consumption |
| Recovery time or the time it takes heart rate to return to a resting rate after heart rate was above 85% of a target maximum | Heart rate, pulse rate, heat flow, oxygen consumption |

Additionally, monitoring device 10 with telemetry system 32 may also generate data indicative of various contextual parameters relating to the environment surrounding the individual. For example, monitoring device 10 can generate data indicative of the air quality, sound level/quality, light quality or ambient temperature near the individual, or even the global positioning of the individual. Sensor device 10 may include one or more sensors for generating signals in response to contextual characteristics relating to the environment surrounding the individual, the signals ultimately being used to generate the type of data described above. Such sensors are well known, as are methods for generating contextual parametric data such as air quality, sound level/quality, ambient temperature and global positioning.

In addition to using monitoring device 10 to automatically collect physiological data relating to an individual user, a kiosk could be adapted to collect such data by, for example, weighing the individual, providing a sensing device similar to monitoring device 10 on which an individual places his or her hand or another part of his or her body, or by scanning the individual's body using, for example, laser technology or an iStat blood analyzer. The kiosk would be provided with processing capability as described herein and access to the relevant electronic network, and would thus be adapted to send the collected data to the telemetry system 32. A desktop sensing device, again similar to monitoring device 10, on which an individual places his or her hand or another part of his or her body, may also be provided. For example, such a desktop sensing device could be a blood pressure monitor in which an individual places his or her arm.

Furthermore, in addition to collecting data by automatically sensing such data in the manners described above, individuals can also manually provide data relating to various life activities that is ultimately transferred to and stored at telemetry system 32 An individual user can access a web site maintained by monitoring system 32 and can directly input information relating to life activities by entering text freely, by responding to questions posed by the web site, or by clicking through dialog boxes provided by the web site. Telemetry system 32 can also be adapted to periodically send electronic mail messages containing questions designed to elicit information relating to life activities to monitoring device 10, a mobile device, PC or to some other device that can receive electronic mail. The individual would then provide data relating to life activities to telemetry system 32 by responding to the appropriate electronic mail message with the relevant data. Telemetry system 32 may also be adapted to place a telephone call to an individual user in which certain questions would be posed to the individual user. The user could respond to the questions by entering information using a telephone keypad, or by voice, in which case conventional voice recognition technology would be used by telemetry system 32 to receive and process the response. The telephone call may also be initiated by the user, in which case the user could speak to a person directly or enter information using the keypad or by voice/voice recognition technology. Monitoring system 32 may also be given access to a source of information controlled by the user, for example the user's electronic calendar such as that provided with the Outlook® calendaring system sold by Microsoft Corporation of Redmond, Wash., from which it could automatically collect information. The data relating to life activities may relate to the eating, sleep, exercise, mind centering or relaxation, and/or daily living habits, patterns and/or activities of the individual. Thus, sample questions may include: What did you have for lunch today? What time did you go to sleep last night? What time did you wake up this morning? How long did you run on the treadmill today?

Feedback may also be provided to a user directly through monitoring device 10 in a visual form, for example through an LED or LCD or by constructing sensor device 10, at least in part, of a thermochromatic plastic, in the form of an acoustic signal or in the form of tactile feedback such as vibration. Such feedback may be a reminder or an alert to eat a meal or take medication or a supplement such as a vitamin, to engage in an activity such as exercise or meditation, or to drink water when a state of dehydration is detected. Additionally, a reminder or alert can be issued in the event that a particular physiological parameter such as ovulation has been detected, a level of calories burned during a workout has been achieved or a high heart rate or respiration rate has been encountered.

As will be apparent to those of skill in the art, it may be possible to "download" data from monitoring system 32 to sensor device 10. The flow of data in such a download process would be substantially the reverse of that described above with respect to the upload of data monitoring device 10. Thus, it is possible that the firmware monitoring device 10 can be updated or altered remotely, i.e., new firmware added, and the like It is also contemplated that a user will input additional data during a session, for example, information relating to the user's eating or sleeping habits.

Data collected by monitoring device 10 can be periodically uploaded to telemetry system 32

Third parties such as insurance companies or research institutions may be given access, possibly for a fee, to certain of the information stored in monitoring system 32.

When an individual user first becomes a registered user or member of telemetry system, that user can complete a detailed survey. The purposes of the survey are to: identify unique characteristics/circumstances for each user that they might need to address in order to maximize the likelihood that they will implement and maintain a healthy lifestyle as suggested by telemetry system 32; gather baseline data which will be used to set initial goals for the individual user and facilitate the calculation and display of certain graphical data output such as the Health Index pistons; identify unique user characteristics and circumstances that will help telemetry system 32 customize the type of content provided to the user; and identify unique user characteristics and circumstances that can guide the user to address as possible barriers to a healthy lifestyle through the problem-solving function monitoring system.

The specific information to be surveyed may include: key individual temperamental characteristics, including activity level, regularity of eating, sleeping, and bowel habits, initial response to situations, adaptability, persistence, threshold of responsiveness, intensity of reaction, and quality of mood; the user's level of independent functioning, i.e., self-organization and management, socialization, memory, and academic achievement skills; the user's ability to focus and sustain attention, including the user's level of arousal, cognitive tempo, ability to filter distractions, vigilance, and self-monitoring; the user's current health status including current weight, height, and blood pressure, most recent general physician visit, gynecological exam, and other applicable physician/healthcare contacts, current medications and supplements, allergies, and a review of current symptoms and/or health-related behaviors; the user's past health history, i.e., illnesses/surgeries, family history, and social stress events, such as divorce or loss of a job, that have required adjustment by the individual; the user's beliefs, values and opinions about health priorities, their ability to alter their behavior and, what might contribute to stress in their life, and how they manage it; the user's degree of self-awareness, empathy, empowerment, and self-esteem, and the user's current daily routines for eating, sleeping, exercise, relaxation and completing activities of daily living; and the user's perception of the temperamental characteristics of two key persons in their life, for example, their spouse, a friend, a co-worker, or their boss, and whether there are clashes present in their relationships that might interfere with a healthy lifestyle or contribute to stress.

Figure 23:
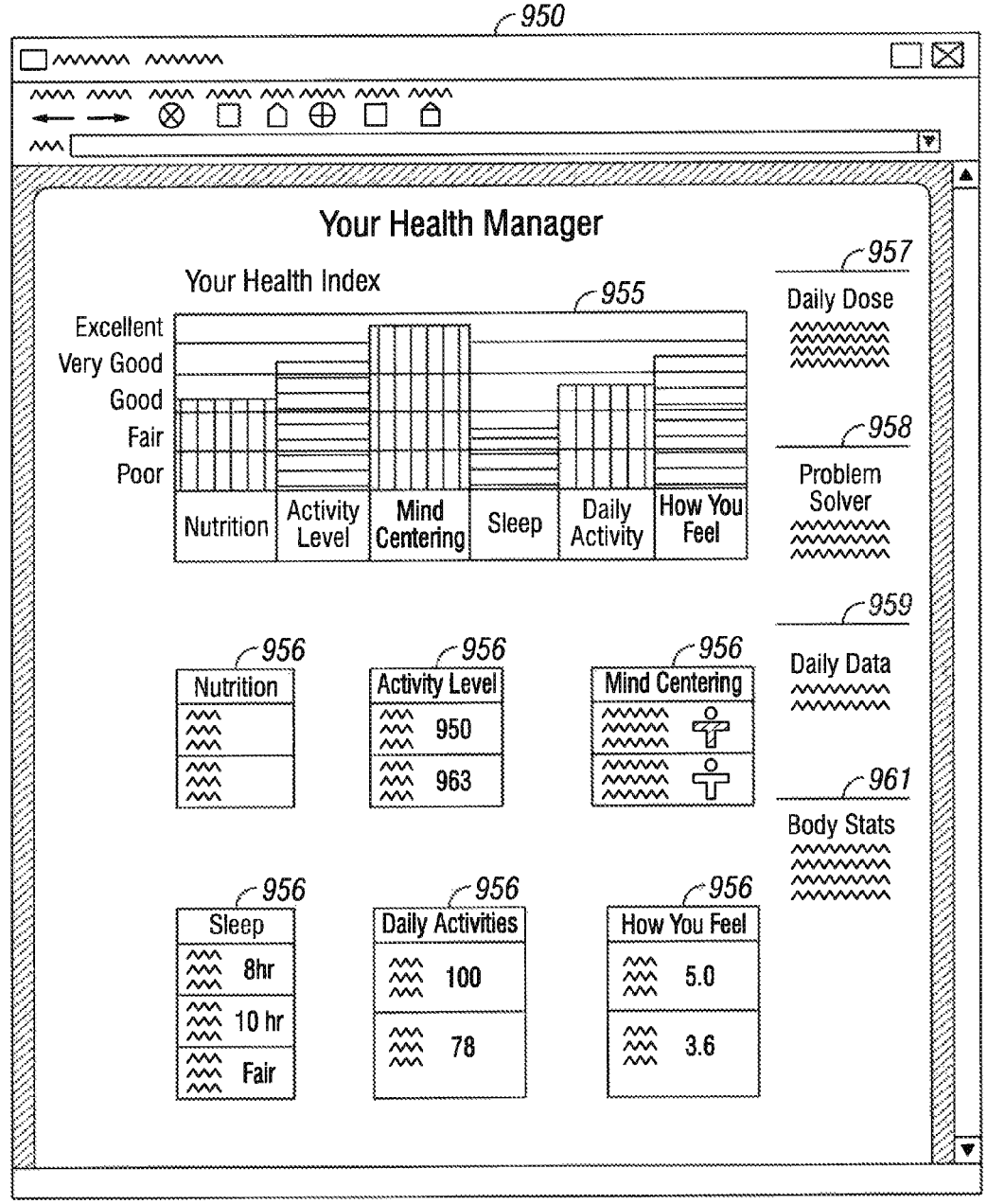
FIG. 23 is a representation of an embodiment of the Health Manager web page according to an aspect of the present invention.

Each member user can access, through a home web page of telemetry system 32, to a series of web pages customized for that user, referred to as the Health Manager. The opening Health Manager web page 950 is shown in FIG. 23. The Health Manager web pages are the main workspace area for the member user. The Health Manager web pages comprise a utility through which telemetry system 32 provides various types and forms of data, commonly referred to as analytical status data, to the user that is generated from the data it collects or generates, namely one or more of: the data indicative of various physiological parameters generated by monitoring device 10; the data derived from the data indicative of various physiological parameters; the data indicative of various contextual parameters generated by monitoring device 10; and the data input by the user. Analytical status data is characterized by the application of certain utilities or algorithms to convert one or more of the data indicative of various physiological parameters generated by monitoring device 10, the data derived from the data indicative of various physiological parameters, the data indicative of various contextual parameters generated by monitoring device 10, and the data input by the user into calculated health, wellness and lifestyle indicators. For example, based on data input by the user relating to the foods he or she has eaten, things such as calories and amounts of proteins, fats, carbohydrates, and certain vitamins can be calculated. As another example, skin temperature, heart rate, respiration rate, heat flow and/or GSR can be used to provide an indicator to the user of his or her stress level over a desired time period. As still another example, skin temperature, heat flow, beat-to-beat heart variability, heart rate, pulse rate, respiration rate, core temperature, galvanic skin response, EMG, EEG, EOG, blood pressure, oxygen consumption, ambient sound and body movement or motion as detected by a device such as an accelerometer can be used to provide indicators to the user of his or her sleep patterns over a desired time period.

Located on the opening Health Manager web page 950 is Health Index 955. Health Index 955 is a graphical utility used to measure and provide feedback to member users regarding their performance and the degree to which they have succeeded in reaching a healthy daily routine suggested by monitoring system 32. Health Index 955 thus provides an indication for the member user to track his or her progress. Health Index 955 includes six categories relating to the user's health and lifestyle: Nutrition, Activity Level, Mind Centering, Sleep, Daily Activities and How You Feel. The Nutrition category relates to what, when and how much a person eats and drinks. The Activity Level category relates to how much a person moves around. The Mind Centering category relates to the quality and quantity of time a person spends engaging in some activity that allows the body to achieve a state of profound relaxation while the mind becomes highly alert and focused. The Sleep category relates to the quality and quantity of a person's sleep. The Daily Activities category relates to the daily responsibilities and health risks people encounter. Finally, the How You Feel category relates to the general perception that a person has about how they feel on a particular day. Each category has an associated level indicator or piston that indicates, preferably on a scale ranging from poor to excellent, how the user is performing with respect to that category.

When each member user completes the initial survey described above, a profile is generated that provides the user with a summary of his or her relevant characteristics and life circumstances. A plan and/or set of goals are provided in the form of a suggested healthy daily routine. The suggested healthy daily routine may include any combination of specific suggestions for incorporating proper nutrition, exercise, and mind centering, sleep, and selected activities of daily living in the user's life. Prototype schedules may be offered as guides for how these suggested activities can be incorporated into the user's life. The user may periodically retake the survey, and based on the results, the items discussed above will be adjusted accordingly.

The Nutrition category is calculated from both data input by the user and sensed by monitoring device 10. The data input by the user comprises the time and duration of breakfast, lunch, dinner and any snacks, and the foods eaten, the supplements such as vitamins that are taken, and the water and other liquids consumed during a relevant, pre-selected time period. Based upon this data and on stored data relating to known properties of various foods, monitoring system 32 calculates well known nutritional food values such as calories and amounts of proteins, fats, carbohydrates, vitamins, etc., consumed.

The Nutrition Health Index piston level is preferably determined with respect to the following suggested healthy daily routine: eat at least three meals; eat a varied diet consisting of 6-11 servings of bread, pasta, cereal, and rice, 2-4 servings fruit, 3-5 servings of vegetables, 2-3 servings of fish, meat, poultry, dry beans, eggs, and nuts, and 2-3 servings of milk, yogurt and cheese; and drink 8 or more 8 ounce glasses of water. This routine may be adjusted based on information about the user, such as sex, age, height and/or weight. Certain nutritional targets may also be set by the user or for the user, relating to daily calories, protein, fiber, fat, carbohydrates, and/or water consumption and percentages of total consumption. Parameters utilized in the calculation of the relevant piston level include the number of meals per day, the number of glasses of water, and the types and amounts of food eaten each day as input by the user.

Figure 24:
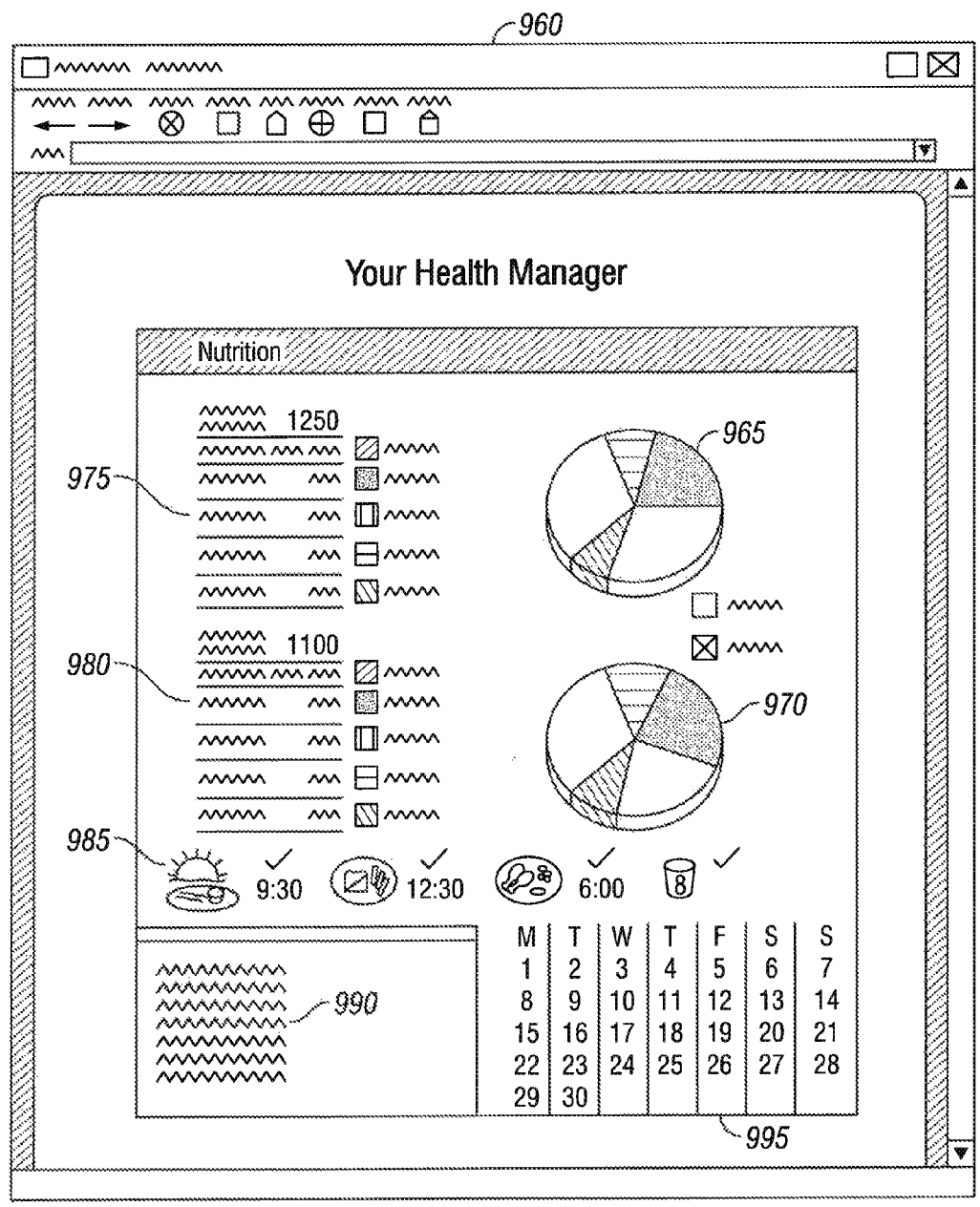
FIG. 24 is a representation of an embodiment of the nutrition web page according to an aspect of the present invention.

Nutritional information is presented to the user through nutrition web page 960 as shown in FIG. 24. The preferred nutritional web page 960 includes nutritional fact charts 965 and 970 which illustrate actual and target nutritional facts, respectively as pie charts, and nutritional intake charts 975 and 980 which show total actual nutritional intake and target nutritional intake, respectively as pie charts. Nutritional fact charts 965 and 970 preferably show a percentage breakdown of items such as carbohydrates, protein and fat, and nutritional intake charts 975 and 980 are preferably broken down to show components such as total and target calories, fat, carbohydrates, protein, and vitamins. Web page 960 also includes meal and water consumption tracking 985 with time entries, hyperlinks 990 which allow the user to directly access nutrition-related news items and articles, suggestions for refining or improving daily routine with respect to nutrition and affiliate advertising elsewhere on the network, and calendar 995 for choosing between views having variable and selectable time periods. The items shown at 990 may be selected and customized based on information learned about the individual in the survey and on their performance as measured by the Health Index.

The Activity Level category of Health Index 955 is designed to help users monitor how and when they move around during the day and utilizes both data input by the user and data sensed by monitoring device 10. The data input by the user may include details regarding the user's daily activities, for example the fact that the user worked at a desk from 8 a.m. to 5 p.m. and then took an aerobics class from 6 p.m. to 7 p.m. Relevant data sensed by monitoring device 10 may include heart rate, movement as sensed by a device such as an accelerometer, heat flow, respiration rate, calories burned, GSR and hydration level, which may be derived by monitoring device 10 or telemetry system 32. Calories burned may be calculated in a variety of manners, including: the multiplication of the type of exercise input by the user by the duration of exercise input by the user; sensed motion multiplied by time of motion multiplied by a filter constant; or sensed heat flux multiplied by time multiplied by a filter constant.

The Activity Level Health Index piston level is preferably determined with respect to a suggested healthy daily routine that includes: exercising aerobically for a pre-set time period, preferably 20 minutes, or engaging in a vigorous lifestyle activity for a pre-set time period, preferably one hour, and burning at least a minimum target number of calories, preferably 205 calories, through the aerobic exercise and/or lifestyle activity. The minimum target number of calories may be set according to information about the user, such as sex, age, height and/or weight. Parameters utilized in the calculation of the relevant piston level include the amount of time spent exercising aerobically or engaging in a vigorous lifestyle activity as input by the user and/or sensed by monitoring device 10, and the number of calories burned above pre-calculated energy expenditure parameters.

Figure 25:
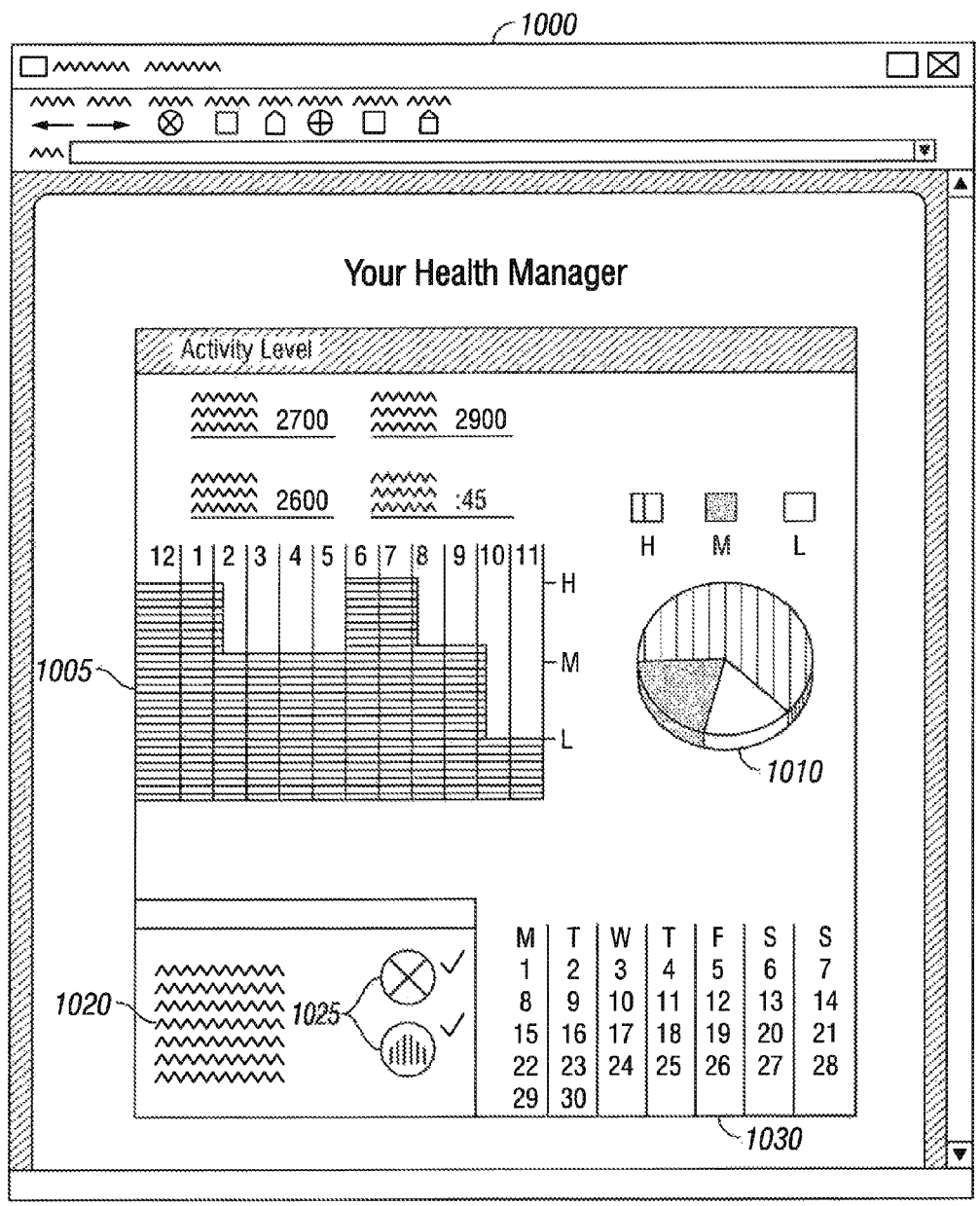
FIG. 25 is a representation of an embodiment of the activity level web page according to an aspect of the present invention.

Information regarding the individual user's movement is presented to the user through activity level web page 1000 shown in FIG. 25, which may include activity graph 1005 in the form of a bar graph, for monitoring the individual user's activities in one of three categories: high, medium and low intensity with respect to a pre-selected unit of time. Activity percentage chart 1010, in the form or a pie chart, may also be provided for showing the percentage of a pre-selected time period, such as one day, that the user spent in each category. Activity level web page 1000 may also include calorie section 1015 for displaying items such as total calories burned, daily target calories burned, total caloric intake, and duration of aerobic activity. Finally, activity level web page 1000 may include at least one hyperlink 1020 to allow a user to directly access relevant news items and articles, suggestions for refining or improving daily routine with respect to activity level and affiliate advertising elsewhere on the network. Activity level web page 1000 may be viewed in a variety of formats, and may include user-selectable graphs and charts such as a bar graph, pie chart, or both, as selectable by Activity level check boxes 1025. Activity level calendar 1030 is provided for selecting among views having variable and selectable time periods. The items shown at 1020 may be selected and customized based on information learned about the individual in the survey and on their performance as measured by the Health Index.

The Mind Centering category of Health Index 955 is designed to help users monitor the parameters relating to time spent engaging in certain activities which allow the body to achieve a state of profound relaxation while the mind becomes focused, and is based upon both data input by the user and data sensed by the monitoring device 10. In particular, a user may input the beginning and end times of relaxation activities such as yoga or meditation. The quality of those activities as determined by the depth of a mind centering event can be measured by monitoring parameters including skin temperature, heart rate, respiration rate, and heat flow as sensed by monitoring device 10. Percent change in GSR as derived either by monitoring device 10 or monitoring system 32 may also be utilized.

The Mind Centering Health Index piston level is preferably calculated with respect to a suggested healthy daily routine that includes participating each day in an activity that allows the body to achieve profound relaxation while the mind stays highly focused for at least fifteen minutes. Parameters utilized in the calculation of the relevant piston level include the amount of time spent in a mind centering activity, and the percent change in skin temperature, heart rate, respiration rate, heat flow or GSR as sensed by monitoring device 10 compared to a baseline which is an indication of the depth or quality of the mind centering activity.

Figure 26:
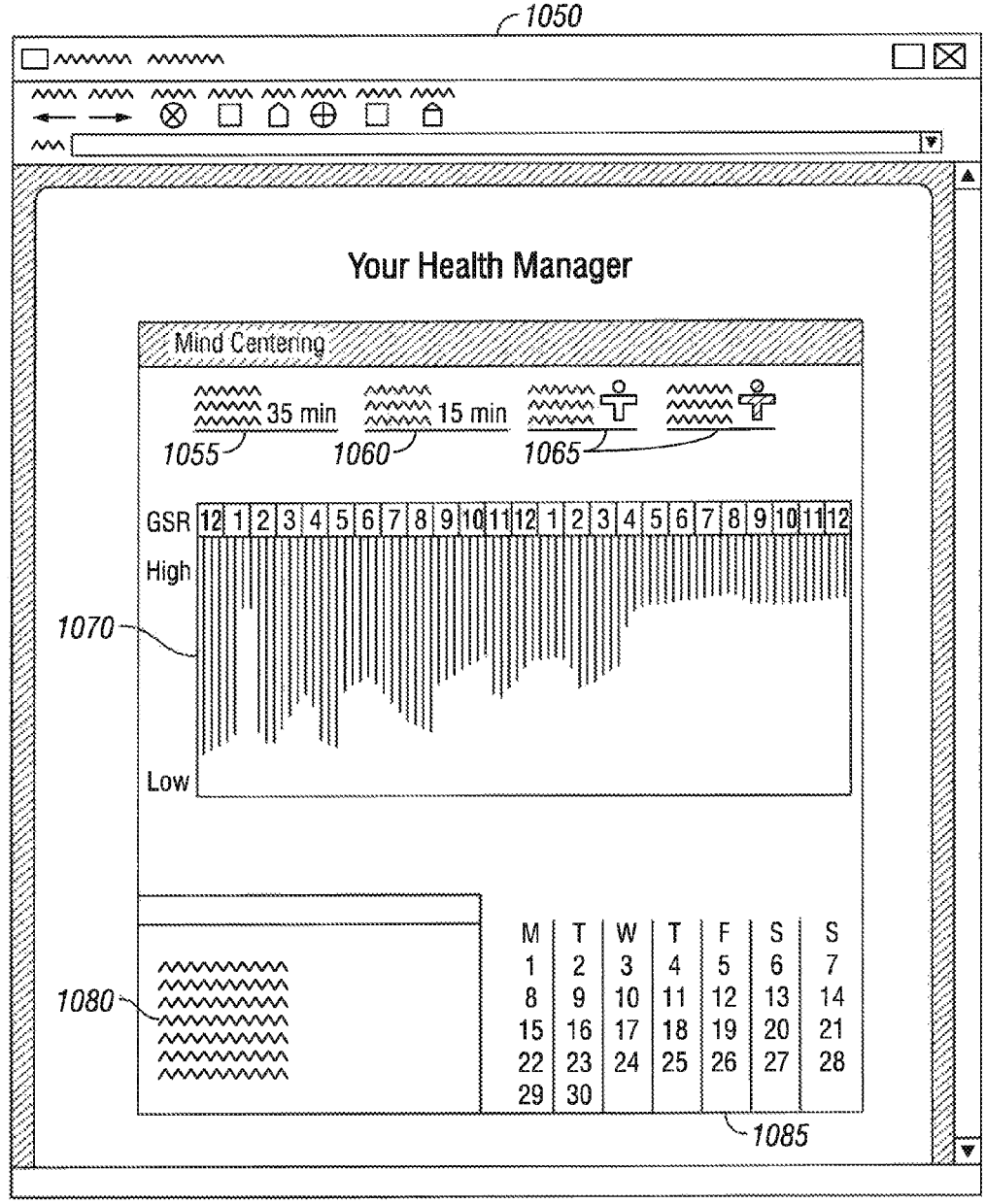
FIG. 26 is a representation of an embodiment of the mind centering web page according to an aspect of the present invention.

Information regarding the time spent on self-reflection and relaxation is presented to the user through mind centering web page 1050 shown in FIG. 26. For each mind centering activity, referred to as a session, the preferred mind centering web page 1050 includes the time spent during the session, shown at 1055, the target time, shown at 1060, comparison section 1065 showing target and actual depth of mind centering, or focus, and a histogram 1070 that shows the overall level of stress derived from such things as skin temperature, heart rate, respiration rate, heat flow and/or GSR. In comparison section 1065, the human figure outline showing target focus is solid, and the human figure outline showing actual focus ranges from fuzzy to solid depending on the level of focus. The preferred mind centering web page may also include an indication of the total time spent on mind centering activities, shown at 1075, hyperlinks 1080 which allow the user to directly access relevant news items and articles, suggestions for refining or improving daily routine with respect to mind centering and affiliate advertising, and a calendar 1085 for choosing among views having variable and selectable time periods. The items shown at 1080 may be selected and customized based on information learned about the individual in the survey and on their performance as measured by the Health Index.

The Sleep category of Health Index 955 is designed to help users monitor their sleep patterns and the quality of their sleep. It is intended to help users learn about the importance of sleep in their healthy lifestyle and the relationship of sleep to circadian rhythms, being the normal daily variations in body functions. The Sleep category is based upon both data input by the user and data sensed by monitoring device 10. The data input by the user for each relevant time interval includes the times the user went to sleep and woke up and a rating of the quality of sleep. The data from monitoring device 10 that is relevant includes skin temperature, heat flow, beat-to-beat heart variability, heart rate, pulse rate, respiration rate, core temperature, galvanic skin response, EMG, EEG, EOG, blood pressure, and oxygen consumption. Also relevant is ambient sound and body movement or motion as detected by a device such as an accelerometer. This data can then be used to calculate or derive sleep onset and wake time, sleep interruptions, and the quality and depth of sleep.

The Sleep Health Index piston level is determined with respect to a healthy daily routine including getting a minimum amount, preferably eight hours, of sleep each night and having a predictable bed time and wake time. The specific parameters which determine the piston level calculation include the number of hours of sleep per night and the bed time and wake time as sensed by monitoring device 10 or as input by the user, and the quality of the sleep as rated by the user or derived from other data.

Figure 27:
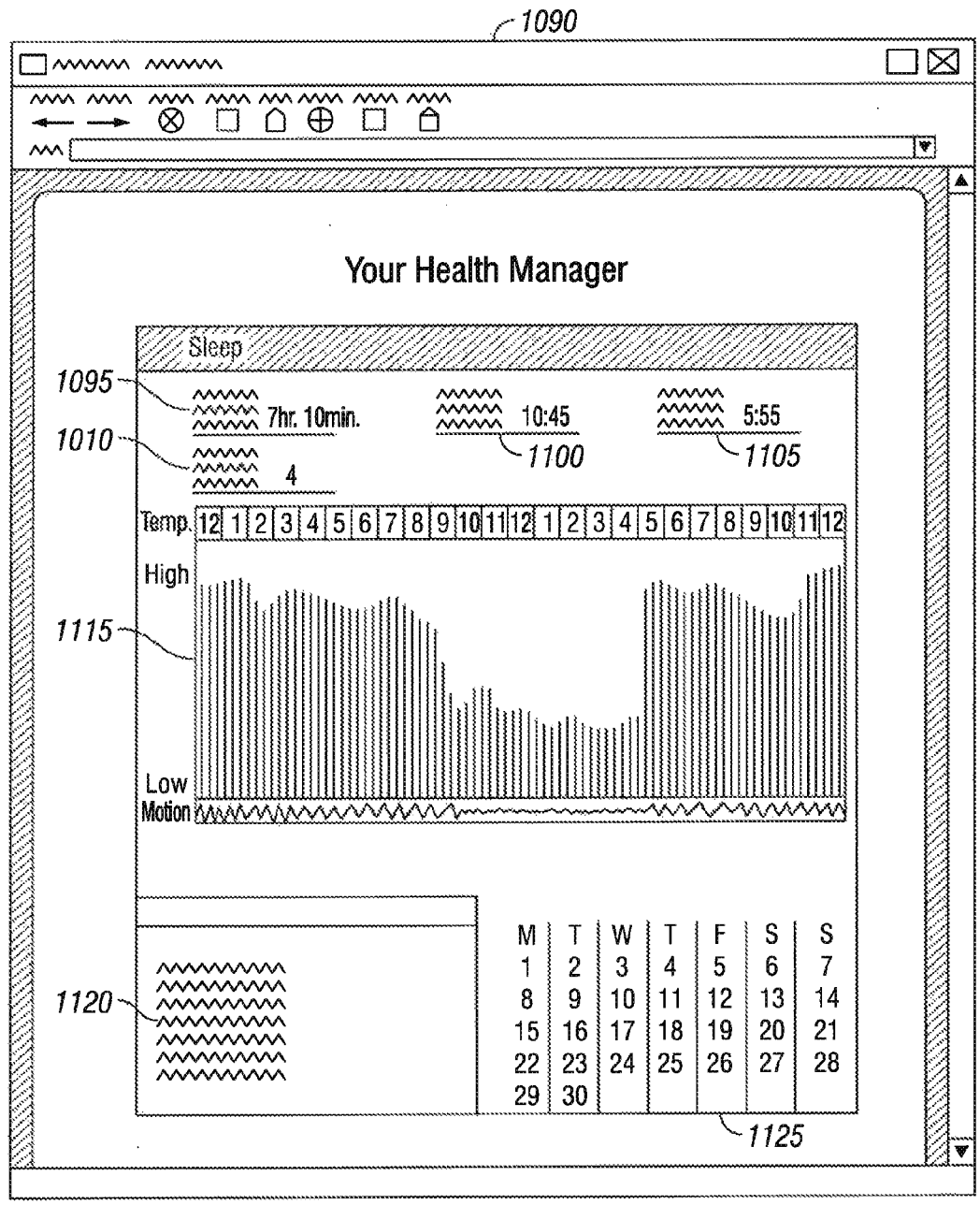
FIG. 27 is a representation of an embodiment of the sleep web page according to an aspect of the present invention.

Information regarding sleep is presented to the user through sleep web page 1090 shown in FIG. 27. Sleep web page 1090 includes a sleep duration indicator 1095, based on either data from monitoring device 10 or on data input by the user, together with user sleep time indicator 1100 and wake time indicator 1105. A quality of sleep rating 1110 input by the user may also be utilized and displayed. If more than a one day time interval is being displayed on sleep web page 1090, then sleep duration indicator 1095 is calculated and displayed as a cumulative value, and sleep time indicator 1100, wake time indicator 1105 and quality of sleep rating 1110 are calculated and illustrated as averages. Sleep web page 1090 also includes a user-selectable sleep graph 1115 which calculates and displays one sleep related parameter over a preselected time interval. For illustrative purposes, FIG. 27 shows heat flow over a one-day period, which tends to be lower during sleeping hours and higher during waking hours. From this information, a person's biorhythms can be derived. Sleep graph 1115 may also include a graphical representation of data from an accelerometer incorporated in monitoring device 10 which monitors the movement of the body. The sleep web page 1090 may also include hyperlinks 1120 which allow the user to directly access sleep related news items and articles, suggestions for refining or improving daily routine with respect to sleep and affiliate advertising available elsewhere on the network, and a sleep calendar 1125 for choosing a relevant time interval. The items shown at 1120 may be selected and customized based on information learned about the individual in the survey and on their performance as measured by the Health Index.

The Activities of Daily Living category of Health Index 955 is designed to help users monitor certain health and safety related activities and risks and is based entirely on data input by the user. The Activities of Daily Living category is divided into four sub-categories: personal hygiene, which allows the user to monitor activities such as brushing and flossing his or her teeth and showering; health maintenance, that tracks whether the user is taking prescribed medication or supplements and allows the user to monitor tobacco and alcohol consumption and automobile safety such as seat belt use; personal time, that allows the user to monitor time spent socially with family and friends, leisure, and mind centering activities; and responsibilities, that allows the user to monitor certain work and financial activities such as paying bills and household chores.

The Activities of Daily Living Health Index piston level is preferably determined with respect to the healthy daily routine described below. With respect to personal hygiene, the routine requires that the users shower or bathe each day, brush and floss teeth each day, and maintain regular bowel habits. With respect to health maintenance, the routine requires that the user take medications and vitamins and/or supplements, use a seat belt, refrain from smoking, drink moderately, and monitor health each day with the Health Manager. With respect to personal time, the routine requires the users to spend at least one hour of quality time each day with family and/or friends, restrict work time to a maximum of nine hours a day, spend some time on leisure or play activity each day, and engage in a mind stimulating activity. With respect to responsibilities, the routine requires the users to do household chores, pay bills, be on time for work, and keep appointments. The piston level is calculated based on the degree to which the user completes a list of daily activities as determined by information input by the user.

Figure 28:
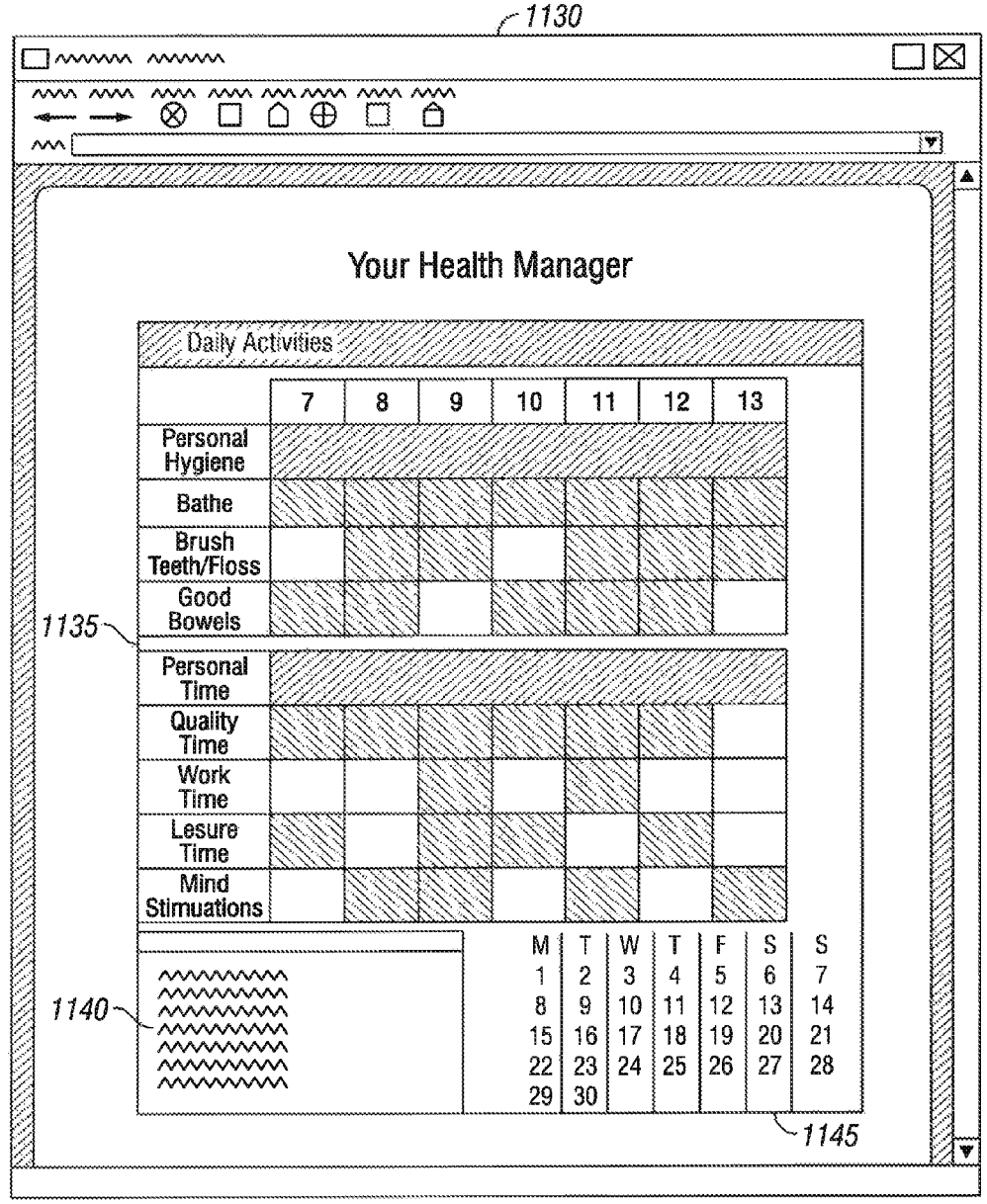
FIG. 28 is a representation of an embodiment of the daily activities web page according to an aspect of the present invention.

Information relating to these activities is presented to the user through daily activities web page 1130 shown in FIG. 28. In preferred daily activities web page 1130, activities chart 1135, selectable for one or more of the sub-categories, shows whether the user has done what is required by the daily routine. A colored or shaded box indicates that the user has done the required activity, and an empty, non-colored or shaded box indicates that the user has not done the activity. Activities chart 1135 can be created and viewed in selectable time intervals. For illustrative purposes, FIG. 28 shows the personal hygiene and personal time sub-categories for a particular week. In addition, daily activities web page 1130 may include daily activity hyperlinks 1140 which allow the user to directly access relevant news items and articles, suggestions for improving or refining daily routine with respect to activities of daily living and affiliate advertising, and a daily activities calendar 1145 for selecting a relevant time interval. The items shown at 1140 may be selected and customized based on information learned about the individual in the survey and on their performance as measured by the Health Index.

The How You Feel category of Health Index 955 is designed to allow users to monitor their perception of how they felt on a particular day, and is based on information, essentially a subjective rating, that is input directly by the user. A user provides a rating, preferably on a scale of 1 to 5, with respect to the following nine subject areas: mental sharpness; emotional and psychological wellbeing; energy level; ability to cope with life stresses; appearance; physical wellbeing; self-control; motivation; and comfort in relating to others. Those ratings are averaged and used to calculate the relevant piston level.

Figure 11:
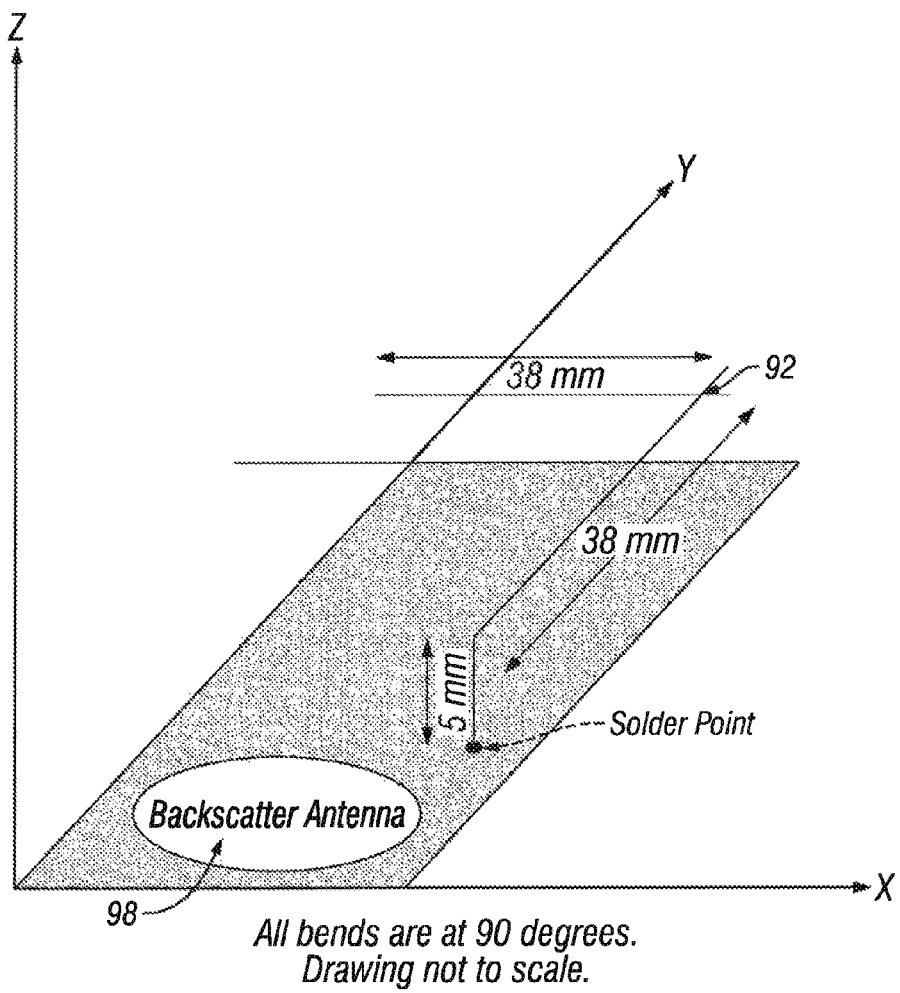
FIG. 11 is a diagram of the active RF and RF backscatter antennas.
Figure 29:
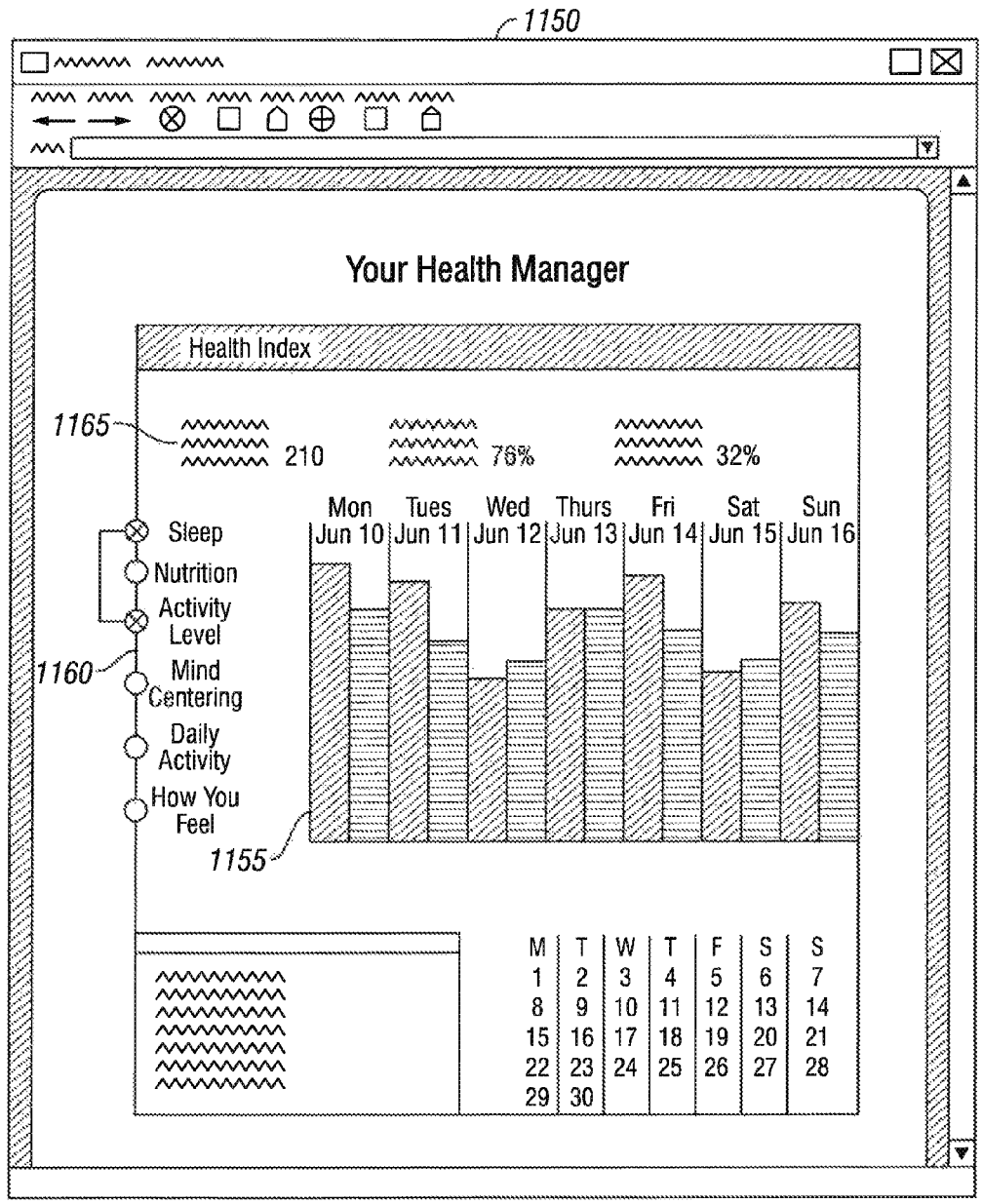
FIG. 29 is a representation of an embodiment of the Health Index web page according to an aspect of the present invention.

Referring to FIG. 29, Health Index web page 1150 is shown. Health Index web page 1150 enables users to view the performance of their Health Index over a user selectable time interval including any number of consecutive or non-consecutive days. Using Health Index selector buttons 1160, the user can select to view the Health Index piston levels for one category, or can view a side-by-side comparison of the Health Index piston levels for two or more categories. For example, a user might want to just turn on Sleep to see if their overall sleep rating improved over the previous month, much in the same way they view the performance of their favorite stock. Alternatively, Sleep and Activity Level might be simultaneously displayed in order to compare and evaluate Sleep ratings with corresponding Activity Level ratings to determine if any day-today correlations exist. Nutrition ratings might be displayed with How You Feel for a pre-selected time interval to determine if any correlation exists between daily eating habits and how they felt during that interval. For illustrative purposes, FIG. 11 illustrates a comparison of Sleep and Activity Level piston levels for the week of June 10 through June 16. Health Index web page 1150 also includes tracking calculator 1165 that displays access information and statistics such as the total number of days the user has logged in and used the Health Manager, the percentage of days the user has used the Health Manager since becoming a subscriber, and percentage of time the user has used the monitoring device 10 to gather data.

Referring again to FIG. 23, opening Health Manager web page 950 may include a plurality of user selectable category summaries 956a through 956f, one corresponding to each of the Health Index 955 categories. Each category summary 956a through 956f presents a pre-selected filtered subset of the data associated with the corresponding category. Nutrition category summary 956a displays daily target and actual caloric intake. Activity Level category summary 956b displays daily target and actual calories burned. Mind Centering category summary 956c displays target and actual depth of mind centering or focus. Sleep category summary 956d displays target sleep, actual sleep, and a sleep quality rating. Daily Activities category summary 956e displays a target and actual score based on the percentage of suggested daily activities that are completed. The How You Feel category summary 956f shows a target and actual rating for the day.

Opening Health Manager web page 950 also may include Daily Dose section 957 which provides, on a daily time interval basis, information to the user, including, but not limited to, hyperlinks to news items and articles, commentary and reminders to the user based on tendencies, such as poor nutritional habits, determined from the initial survey. The commentary for Daily Dose 957 may, for example, be a factual statement that drinking 8 glasses of water a day can reduce the risk of colon cancer by as much as 32%, accompanied by a suggestion to keep a cup of water by your computer or on your desk at work and refill often. Opening Health Manager web page 950 also may include a Problem Solver section 958 that actively evaluates the user's performance in each of the categories of Health Index 955 and presents suggestions for improvement. For example, if the system detects that a user's Sleep levels have been low, which suggest that the user has been having trouble sleeping, Problem Solver 958 can provide suggestions for way to improve sleep. Problem Solver 958 also may include the capability of user questions regarding improvements in performance. Opening Health Manager web page 950 may also include a Daily Data section 959 that launches an input dialog box. The input dialog box facilitates input by the user of the various data required by the Health Manager. As is known in the art, data entry may be in the form of selection from pre-defined lists or general free form text input. Finally, opening Health Manager web page 950 may include Body Stats section 961 which may provide information regarding the user's height, weight, body measurements, body mass index or BMI, and vital signs such as heart rate, blood pressure or any of the identified physiological parameters.

The foregoing description of various embodiments of the claimed subject matter has been provided for the purposes of illustration and description. It is not intended to be exhaustive or to limit the claimed subject matter to the precise forms disclosed. Many modifications and variations will be apparent to the practitioner skilled in the art. Particularly, while the concept "component" is used in the embodiments of the systems and methods described above, it will be evident that such concept can be interchangeably used with equivalent concepts such as, class, method, type, interface, module, object model, and other suitable concepts. Embodiments were chosen and described in order to best describe the principles of the invention and its practical application, thereby enabling others skilled in the relevant art to understand the claimed subject matter, the various embodiments and with various modifications that are suited to the particular use contemplated.

What is claimed is:

1. A method for obtaining monitored information about an individual and provide the individual with feedback, comprising:
   detecting or measuring information about the individual using a monitoring device that includes a microphone, an RF transmitter and sensors to determine air quality, sound level/quality, light quality and ambient temperature near the individual, the RF transmitter serving as a communication system;
   an accelerometer configured to detect the individual's movement information, the accelerometer and the monitoring system configured to assist to determine the individual's sleep information and sleep behavior information, the microphone configured to record an individual's movement sounds detected by the accelerometer, the accelerometer configured to cause the microphone to stop recording the individual's movement sounds when the movement sounds are not directed to a sleep related parameter; and
   communicating between the monitoring device and a telemetry system, the telemetry system having a database that includes base individual information of the individual's sleep information and sleep behavior information from the monitoring device and the accelerometer
   accessing an individual's profile stored in the database, the telemetry system in operation selecting records of sleep information and sleep behavior information data of one or more individual's, the telemetry system configured to receive the individual's movement and monitoring device, with the telemetry system or the monitoring system analyzing the individual's movement information and the monitoring device information to calculate or derive sleep onset and wake time, sleep interruptions, and the quality and depth of sleep; and
   providing feedback to the user regarding one or more of the individual's sleep onset and wake time, sleep interruptions, and the quality and depth of sleep.

2. The method of claim 1, further comprising:
using one or more analysis tools at the telemetry system.

3. The method of claim 2, further comprising:
providing feedback to the individual using a feedback system or subsystem at the telemetry system.

4. The method of claim 2, further comprising:
comparing the individual's sleep information or sleep related information from the monitoring device or accelerometer to information in the database using the one or more analysis tool.

5. The method of claim 4, further comprising:
applying threshold values that are included in the database.

6. The method of claim 5, further comprising:
comparing the user information from the monitoring device or accelerometer to threshold values using the one or more analysis tools.

7. The method of claim 6, further comprising:
using an alert at the monitoring device.

8. The method of claim 7, further comprising:
activating the alert when an individual information exceeds a threshold value.

9. The method of claim 8, further comprising:
activating the alert only when the individual is awake.

10. The method of claim 7, wherein the alert is an audio or visual alert.

11. The method of claim 10, further comprising:
providing at least one of a display and an audio device at the monitoring system.

12. The method of either claim 3, further comprising:
providing the feedback in graphical form.

13. The method of claim 3, further comprising:
generating one or more web pages that contain feedback.

14. A method for obtaining monitored information about an individual and provide the individual with feedback, comprising:
- detecting or measuring information about the individual using a monitoring device that includes a microphone, an RF transmitter and sensors to determine air quality, sound level/quality, light quality and ambient temperature near the individual;
- an accelerometer configured to detect the individual's movement information, the accelerometer and the monitoring system configured to assist to determine the individual's sleep information and sleep behavior information, the microphone configured to record an individual's movement sounds detected by the accelerometer, the accelerometer configured to cause the microphone to stop recording the individual's movement sounds when the movement sounds are not directed to a sleep related parameter;
- communicating between the monitoring device and a telemetry system, the telemetry system having a database that includes individual information of the individual's sleep information and sleep behavior information from the monitoring device and the accelerometer indicative of the individual's sleep information and sleep behavior and information regarding a degree to which an individual's sleep information and sleep behavior compares with the individual's sleep information and sleep behavior with information stored in a database about the individual; and
- providing feedback to the user regarding one or more of the individual's sleep onset and wake time, sleep interruptions, and the quality and depth of sleep.

15. The method of claim 14, further comprising:
applying one or more analysis tools at the telemetry system.

16. The method of claim 15, further comprising:
providing feedback to the individual using a feedback system or subsystem at the telemetry system.

17. The method of claim 15, further comprising:
comparing the individual information from the monitoring device to the base individual information in the database.

18. The method of claim 15, further comprising:
including threshold values relative to the individual.

19. The method of claim 15, further comprising:
comparing the individual information from the monitoring device to the threshold values.

20. The method of claim 14, further comprising:
providing an alert at the monitoring device.

21. The method of claim 20, further comprising:
activating the alert when an individual information exceeds a threshold value.

22. The method of claim 21, further comprising:
activating the alert only when the individual is awake.

23. The method of claim 20, wherein the alert is an audio or visual alert.

24. The method of claim 14, wherein the monitoring system includes at least one of a display and an audio device.

25. The method of either claim 15, further comprising:
providing feedback in graphical form.

26. The method of claim 15, further comprising:
generating one or more web pages containing feedback.

* * * * *